US012110492B2

(12) United States Patent
Carlson et al.

(10) Patent No.: US 12,110,492 B2
(45) Date of Patent: Oct. 8, 2024

(54) RNAI AGENTS FOR INHIBITING EXPRESSION OF COMPLEMENT COMPONENT C3 (C3), PHARMACEUTICAL COMPOSITIONS THEREOF, AND METHODS OF USE

(71) Applicant: Arrowhead Pharmaceuticals, Inc., Pasadena, CA (US)

(72) Inventors: Jeffrey Carlson, Madison, WI (US); Yichen Wang, San Diego, CA (US); Tao Pei, Middleton, WI (US); James C. Hamilton, Arcadia, CA (US); Hamid Moradi, Laguna Hills, CA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 18/495,278

(22) Filed: Oct. 26, 2023

(65) Prior Publication Data

US 2024/0167035 A1 May 23, 2024

Related U.S. Application Data

(60) Provisional application No. 63/493,564, filed on Mar. 31, 2023, provisional application No. 63/486,944, filed on Feb. 24, 2023, provisional application No. 63/381,200, filed on Oct. 27, 2022.

(51) Int. Cl.
*C07H 21/04* (2006.01)
*C12N 15/113* (2010.01)

(52) U.S. Cl.
CPC ........ *C12N 15/113* (2013.01); *C12N 2310/14* (2013.01); *C12N 2310/321* (2013.01); *C12N 2310/351* (2013.01)

(58) Field of Classification Search
CPC .......................... C12N 15/113; C12N 2310/14
See application file for complete search history.

(56) References Cited

U.S. PATENT DOCUMENTS

| | | | |
|---|---|---|---|
| 7,582,746 B2 | 9/2009 | Khvorova et al. | |
| 10,465,194 B2 | 11/2019 | Borodovsky et al. | |
| 2007/0178068 A1 | 8/2007 | Reich et al. | |
| 2008/0090997 A1 | 4/2008 | Khvorova et al. | |
| 2014/0154783 A1 | 6/2014 | Rossomando et al. | |
| 2020/0282012 A1 | 9/2020 | Francois | |
| 2023/0272382 A1* | 8/2023 | Keating | C12N 15/113 514/44 A |

FOREIGN PATENT DOCUMENTS

| | | |
|---|---|---|
| WO | 2007064846 A2 | 6/2007 |
| WO | 2009031721 A1 | 3/2009 |
| WO | 2015089368 A1 | 6/2015 |
| WO | 2018075373 A1 | 4/2018 |
| WO | 2019089922 A1 | 5/2019 |
| WO | 2020104669 A1 | 5/2020 |
| WO | 2021037941 A1 | 3/2021 |
| WO | 2021081026 A1 | 4/2021 |
| WO | 2021163654 A1 | 8/2021 |
| WO | 2021178607 A1 | 9/2021 |
| WO | 2023044370 A2 | 3/2023 |
| WO | 2023186056 A1 | 10/2023 |

OTHER PUBLICATIONS

Zanchi et al. (The Journal of Immunology, 2022, 208, 1772-1781).*
Gupta et al. (PLOS ONE, 2014, 9, 4, e95478, pp. 1-9).*
Ornellas et al. (IBJU, vol. 38 (6): 739-749, 2012).*
Natoli et al.; "Retinal Macrophages Synthesize C3 and Activate Complement in AMD and in Models of Focal Retinal Degeneration"; Invest Ophthalmol Vis Sci. Jun. 1, 2017;58(7):2977-2990. doi: 10.1167/iovs.17-21672. PMID: 28605809.
Zanchi et al.; "Therapeutic Small Interfering RNA Targeting Complement C3 in a Mouse Model of C3 Glomerulopathy"; J Immunol. Apr. 1, 2022;208(7):1772-1781. doi: 0.4049/jimmunol.2100730. Epub Mar. 11, 2022. PMID: 35277417.
Zheng et al.; "Preventing renal ischemia-reperfusion injury using small interfering RNA by targeting complement 3 gene"; Am J Transplant. Sep. 2006;6(9):2099-108. doi: 10.1111/j.1600-6143. 2006.01427.x. Epub Jun. 22, 2006. PMID: 16796725.
Product Information Sheet; "Silencer® Select Pre-designed (Inventoried) siRNA Product Information Sheet"; Ambion, Life Technologies Corporation; 2010.
Basiri B. et al.; "Introducing an In Vitro Liver Stability Assay Capable of Predicting the In Vivo Pharmacodynamic Efficacy of siRNAs for IVIVC"; Mol Ther Nucleic Acids. Sep. 4, 2020;21:725-736. doi: 10.1016/j.omtn.2020.07.012. Epub Jul. 10, 2020. PMID: 32771924; PMCID: PMC7415771.
Friedrich et al.; "Therapeutic siRNA: State-of-the-Art and Future Perspectives"; BioDrugs. Sep. 2022; 36(5):549-571. doi: 10.1007/s40259-022-00549-3. Epub Aug. 23, 2022. PMID: 35997897; PMCID: PMC9396607.
Jackson et al.; "Expression profiling reveals off-target gene regulation by RNAi"; Nat Biotechnol. Jun. 2003;21(6):635-7. doi: 10.1038/nbt831. Epub May 18, 2003. PMID: 12754523.

(Continued)

*Primary Examiner* — Amy Rose Hudson
(74) *Attorney, Agent, or Firm* — Robert M. Teigen; Paul Vandervelde; Meibo Chen

(57) ABSTRACT

The present disclosure relates to RNAi agents, e.g., double stranded RNAi agents or siRNAs, able to inhibit Complement Component C3 (C3) gene expression. Also disclosed are pharmaceutical compositions that include C3 RNAi agents and methods of use thereof. The C3 RNAi agents disclosed herein may be conjugated to targeting ligands, including ligands that comprise N-acetyl-galactosanine, to facilitate the delivery to hepatocyte cells. Delivery of the C3 RNAi agents in vivo provides for inhibition of C3 gene expression. The RNAi agents can be used in methods of treatment of diseases, disorders, or symptoms mediated in part by C3 gene expression, including IgA nephropathy, C3 glomerulopathy, paroxysmal nocturnal hemoglobinuria, and/or other complement-mediated renal diseases.

14 Claims, 19 Drawing Sheets

Specification includes a Sequence Listing.

(56) References Cited

OTHER PUBLICATIONS

Kamola et al.; "The siRNA Non-seed Region and Its Target Sequences Are Auxiliary Determinants of Off-Target Effects"; PLoS Comput Biol. Dec. 11, 2015;11(12):e1004656. doi: 10.1371/journal.pcbi.1004656. PMID: 26657993; PMCID: PMC4676691.

Nair JK et al.; "Impact of enhanced metabolic stability on pharmacokinetics and pharmacodynamics of GalNAc-siRNA conjugates"; Nucleic Acids Res. Nov. 2, 2017;45(19):10969-10977. doi: 10.1093/nar/gkx818. PMID: 28981809; PMCID: PMC5737438.

Naito et al.; "siRNA Design Software for a Target Gene-Specific RNA Interference"; Front Genet. Jun. 11, 2012;3:102. doi: 10.3389/fgene.2012.00102. PMID: 22701467; PMCID: PMC3371628.

Pascut et al.; "Silencing efficacy prediction: a retrospective study on target mRNA features"; Biosci Rep. Mar. 31, 2015;35(2):e00185. doi: 10.1042/BSR20140147. PMID: 25702798; PMCID: PMC4381284.

Bartoszewski et al.; "Editorial focus: understanding off-target effects as the key to successful RNAi therapy"; Cell Mol Biol Lett. Dec. 9, 2019;24:69. doi: 10.1186/s11658-019-0196-3. PMID: 31867046; PMCID: PMC6902517.

Davis et al.; "2'-O-Methyl at 20-mer Guide Strand 3' Termini May Negatively Affect Target Silencing Activity of Fully Chemically Modified siRNA"; Mol Ther Nucleic Acids. Sep. 4, 2020;21:266-277. doi: 10.1016/j.omtn.2020.05.010. Epub May 15, 2020. PMID: 32610253; PMCID: PMC7327867.

\* cited by examiner

AD09546

| NAG37s invAb | s | a | c | c | o | c | o | u | o | a | c | o | u | o | Cf | o | Uf | o | Gf | o | u | o | u | o | c | o | g | o | a | o | a | s invAb |
|---|---|---|---|---|---|---|---|---|---|---|---|---|---|---|---|---|---|---|---|---|---|---|---|---|---|---|---|---|---|---|---|---|

Sense Strand (5' → 3')    (AM12489-SS) (SEQ ID NO:14)

| | u | s | g | o | Gf | o | Gf | o | a | o | Uf | o | g | o | Af | o | g | o | Af | o | Af | o | a | o | a | o | a | o | c | o | a | o | a | o | g | o | Cf | s | u | Uf | s | u |
|---|---|---|---|---|---|---|---|---|---|---|---|---|---|---|---|---|---|---|---|---|---|---|---|---|---|---|---|---|---|---|---|---|---|---|---|---|---|---|---|---|---|

Antisense Strand (3' ← 5')    (AM13561-AS) (SEQ ID NO:13)

FIG. 18

RNAI AGENTS FOR INHIBITING EXPRESSION OF COMPLEMENT COMPONENT C3 (C3), PHARMACEUTICAL COMPOSITIONS THEREOF, AND METHODS OF USE

CROSS REFERENCE TO RELATED APPLICATIONS

This application claims the benefit of priority of U.S. Provisional Patent Application Ser. No. 63/381,200, filed on Oct. 27, 2022, U.S. Provisional Patent Application Ser. No. 63/486,944, filed on Feb. 24, 2023, and U.S. Provisional Patent Application Ser. No. 63/493,564, filed on Mar. 31, 2023, the contents of each of which are incorporated herein by reference in their entirety.

SEQUENCE LISTING

This application contains a Sequence Listing which has been submitted in XML format and is hereby incorporated by reference in its entirety. The XML copy is named 30698-WO1_SeqListing.xml, was created on Oct. 25, 2023, and is 49 kb in size.

FIELD OF THE INVENTION

The present disclosure relates to RNA interference (RNAi) agents, e.g., double stranded RNAi agents or interfering RNA molecules, for inhibition of Complement Component C3 (C3) gene expression, pharmaceutical compositions that include C3 RNAi agents, and methods of use thereof for the treatment of C3-related diseases and disorders, including complement-mediated renal diseases (CMRDs) such as IgA nephropathy (IgAN) and C3 glomerulopathy (C3G).

BACKGROUND

The complement cascade is a crucial part of the innate immune system and is known to consist of three distinct pathways: the alternative pathway, the classical pathway, and the lectin pathway. Each of the three major pathways of complement activity can play an important role in the pathogenesis of various diseases. Some of the main functions of the complement system include orchestrating opsonization, facilitating cytotoxic destruction and formulating membrane attack complexes, and releasing peptides that promote the inflammatory response. An overview of the complement system focusing on relevant targets for therapeutic inhibition is described, for example, in Garred et. al., Pharmacol. Rev. 73:792-827, April 2021 (see, e.g., FIG. 1 therein). One of the identified complement system targets, complement component C3, is believed to be involved in the pathogenesis of certain diseases, including but are not limited to paroxysmal nocturnal hemoglobinuria (PNH) and complement-mediated renal diseases (CMRDs), such as IgA nephropathy (IgAN) and C3 glomerulopathy (C3G).

Currently, there are either very limited or no treatment options for various diseases associated with dysregulated complement activity. For both IgAN and C3G, there are no approved medications available in the United States. For other complement-related diseases like PNH where treatments are commercially available, substantial unmet medical need remains for many patients due to limitations of the approved therapeutics and their respective mechanisms of action. For example, monoclonal antibodies eculizumab and ravulizumab are inhibitors of Complement Component C5 that are approved for the treatment of PNH, but require a 2- to 3-hour intravenous infusion every 2 weeks to 2 months, and they do not block all of the effector pathways of complement activation because they act more distally in the cascade (at C5, rather than C3). Further, pegcetacoplan, a therapeutic peptide designed to inhibit C3, requires administration of approximately 1 gram of drug in 20 milliliters to be administered by a subcutaneous infusion pump where the infusion occurs over the course of one hour and must be administered twice each week.

In recent clinical trials, both pegcetacoplan and factor B inhibitor iptacopan were shown to be superior to C5 inhibition alone (by eculizumab) in improving hemoglobin and clinical and hematologic outcomes in patients with PNH (Hillmen, N Engl J Med. 2021, 384(11):1028-37; Peffault de Latour, Blood 2022, 140(Supplement 2):LBA-2; Risitano, Lancet Haematol. 2021, 8(5):e344-e354). These studies, along with the evolving understanding of the importance of the role of C3 and the alternative pathway of complement in conditions such as PNH, C3G, and IgAN, provide a strong rationale for targeting the proximal alternative complement pathway, and C3 in particular, as a therapeutic strategy for these conditions.

Thus, there remains a need for a highly active, durable, and safe therapeutic capable of inhibiting C3 and the complement cascade more proximally. While various publications have proposed interfering RNA molecules for targeting C3, prior to the present disclosure none has shown the elusive combination of sufficient activity at inhibiting gene expression to provide a therapeutic benefit, a suitable safety profile to be viable as a therapeutic in humans, and suitable durability to require in-frequent administration to address compliance issues for certain patients that have trouble with any existing approved therapies.

SUMMARY

Disclosed herein are RNAi agents for inhibiting expression of a C3 gene, comprising:
  an antisense strand wherein nucleotides 1-21 of the antisense strand comprise nucleotides 1-21 of one of the antisense strand sequences of Table 2, and
  a sense strand comprising a nucleotide sequence that is at least partially complementary to the antisense strand,
  wherein all or substantially all of the nucleotides of the antisense strand and/or the sense strand are modified nucleotides, and wherein the RNAi agent is linked to a targeting ligand that comprises N-acetyl-galactosamine.

In some embodiments, the sense strand comprises a nucleotide sequence of at least 15 contiguous nucleotides differing by 0 or 1 nucleotides from 15 contiguous nucleotides of any one of the sense strand sequences of Table 2, Table 4, Table 5C, Table 7B, or Table 8, and wherein the sense strand has a region of at least 85% complementarity over the 15 contiguous nucleotides to the antisense strand.

In some embodiments, at least one nucleotide of the RNAi agent includes a modified internucleoside linkage.

In some embodiments, the modified nucleotides of the C3 RNAi agents disclosed herein are selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate containing nucleotide, cyclopropyl phosphonate containing nucleotide, and 3'-O-methyl nucleotide.

In other embodiments, all or substantially all of the modified nucleotides of the RNAi agents disclosed herein are 2'-O-methyl nucleotides, 2'-fluoro nucleotides, or combinations thereof.

In some embodiments, the antisense strand consists of, consists essentially of, or comprises the nucleotide sequence of any one of the modified antisense strand sequences of Table 3.

In some embodiments, the sense strand consists of, consists essentially of, or comprises the nucleotide sequence of any of the modified sense strand sequences of Table 4.

In some embodiments, the antisense strand comprises the nucleotide sequence of any one of the modified sequences of Table 3 and the sense strand comprises the nucleotide sequence of any one of the modified sequences of Table 4.

The RNAi agents disclosed herein are linked to a targeting ligand that comprises N-acetyl-galactosamine. In further embodiments, the targeting ligand is linked to the sense strand. In some embodiments, the targeting ligand is linked to the 5' terminal end of the sense strand.

In some embodiments, the sense strand is between 15 and 30 nucleotides in length, and the antisense strand is between 21 and 30 nucleotides in length. In other embodiments, the sense strand and the antisense strand are each between 21 and 27 nucleotides in length. In other embodiments, the sense strand and the antisense strand are each between 21 and 24 nucleotides in length. In still other embodiments, sense strand and the antisense strand are each 21 nucleotides in length.

In some embodiments, the RNAi agents have two blunt ends.

In some embodiments, the sense strand comprises one or two terminal caps. In other embodiments, the sense strand comprises one or two inverted abasic residues.

In some embodiments, the RNAi agents are comprised of a sense strand and an antisense strand that form a duplex sequence of the duplex structures shown in Table 5A, 5B, 5C, or 8.

In some embodiments, the sense strand further includes inverted abasic residues at the 3' terminal end of the nucleotide sequence, at the 5' end of the nucleotide sequence, or at both.

In further embodiments, the targeting ligand comprises or consists of.

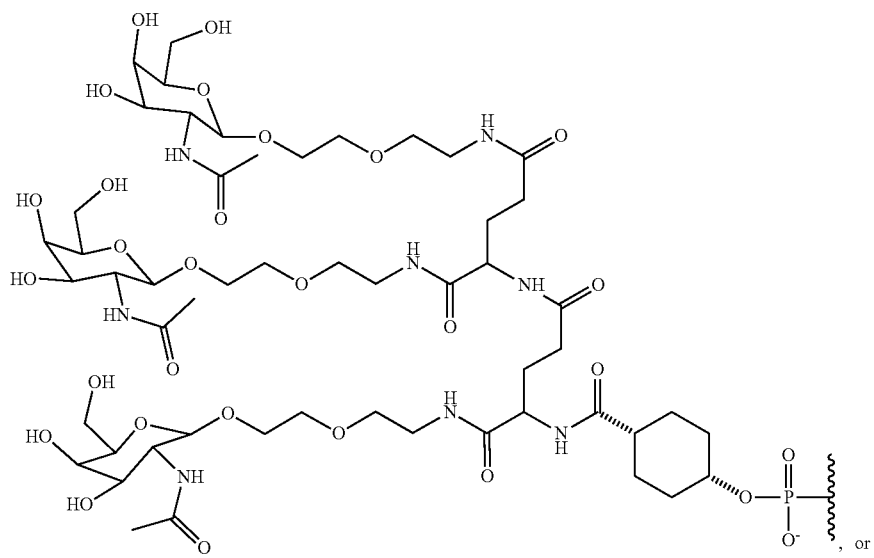

(NAG37)

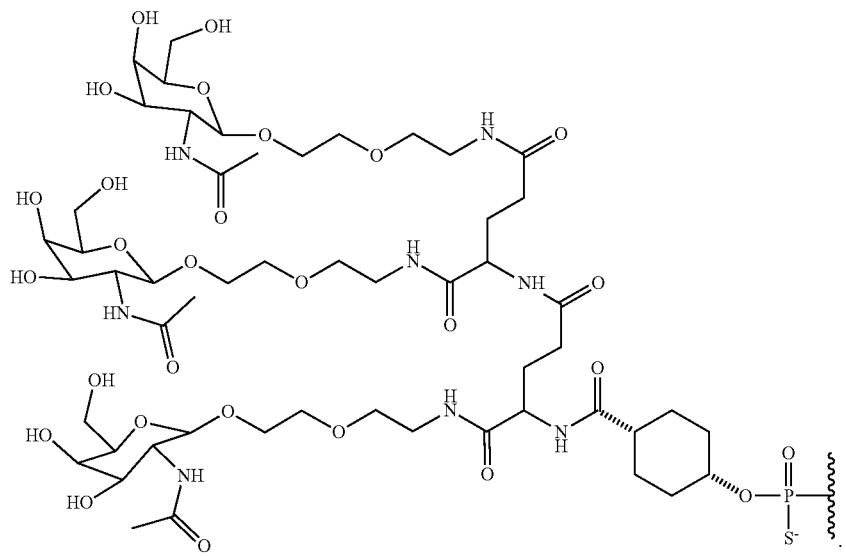

(NAG37s)

Also disclosed herein are compositions comprising the disclosed RNAi agents, wherein the compositions further comprise a pharmaceutically acceptable excipient.

Additionally, provided herein are methods for inhibiting expression of a C3 gene in a hepatocyte cell in a human subject in vivo, the methods comprising introducing into the subject an effective amount of the disclosed C3 RNAi agents or the disclosed compositions.

Further provided herein are methods of treating a C3-related disease, disorder, or symptom, the methods comprising administering to a human subject in need thereof a therapeutically effective amount of the disclosed compositions.

In some embodiments, the disease is IgA nephropathy, C3 glomerulopathy, and/or paroxysmal nocturnal hemoglobinuria.

In some embodiments, the RNAi agents are administered at a dose of about 0.05 mg/kg to about 5.0 mg/kg of body weight of the human subject. In some embodiments, the C3 RNAi agents disclosed herein are administered in a fixed dose of a single injection containing about 25 mg, 50 mg, about 100 mg, about 200 mg, about 300 mg, or about 400 mg of C3 RNAi Agent Drug Substance, as described in Table 8.

Also provided herein are usages of the disclosed RNAi agents or the disclosed compositions, for the treatment of a disease, disorder, or symptom that is associated with complement dysregulation.

Further provided herein are usages of the disclosed RNAi agents or the disclosed compositions, for the preparation of a pharmaceutical compositions for treating a disease, disorder, or symptom that is mediated at least in part by dysregulated complement activity, dysregulated C3 activity, or C3 gene expression.

BRIEF DESCRIPTION OF THE DRAWINGS

FIG. 18. Schematic diagram of the modified sense and antisense strands of the C3 RNAi agent having the structure of AD09546 (see, e.g., Tables 3, 4A, and 5C) having a tridentate N-acetyl-galactosamine targeting group at the 5' terminal end of the sense strand. The following abbreviations are used in FIG. 16: a, c, g, and u are 2'-O-methyl modified nucleotides; Af, Cf, Gf, and Uf are 2'-fluoro modified nucleotides; o is a phosphodiester linkage; s is a phosphorothioate linkage; invAb is an inverted abasic residue (see, e.g., Table 6), and NAG37s is a tridentate N-acetyl-galactosamine targeting ligand having the following chemical structure:

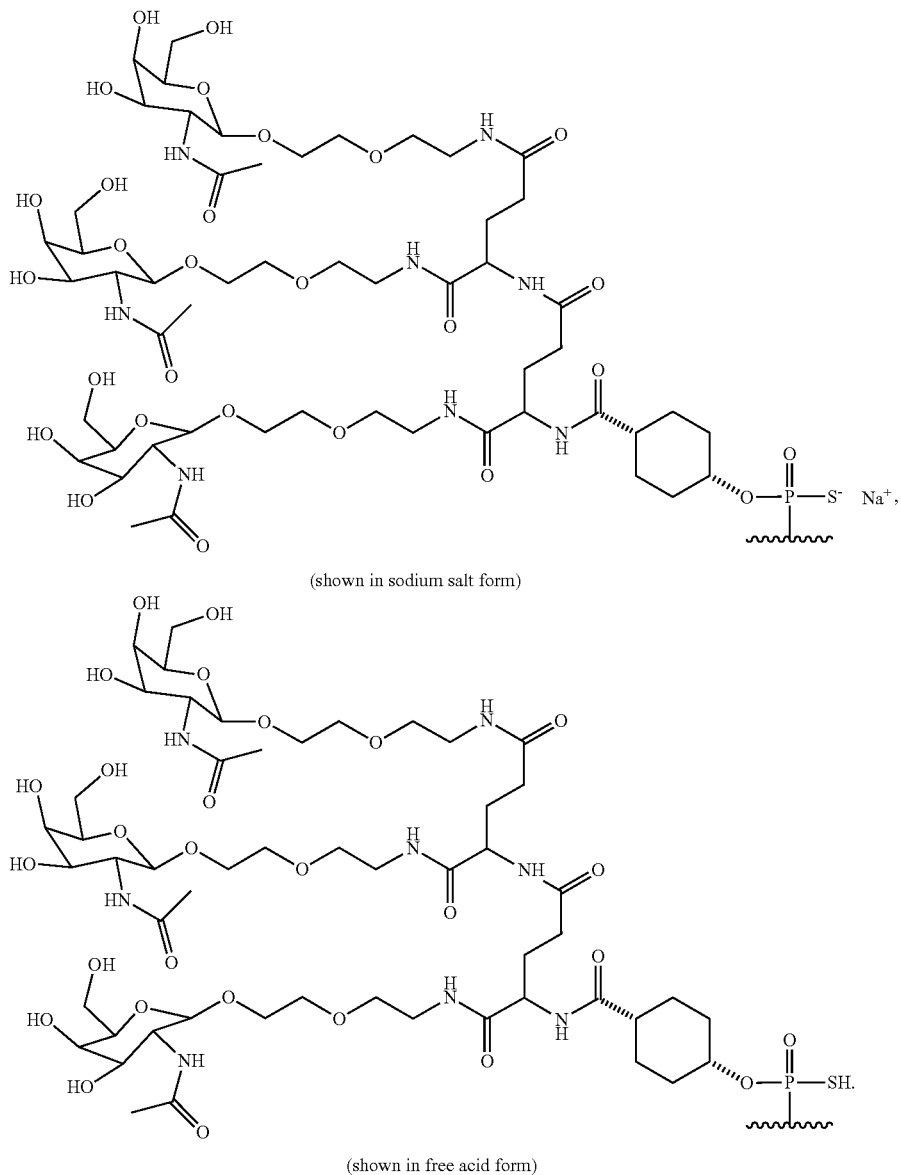

(shown in sodium salt form)

(shown in free acid form)

DETAILED DESCRIPTION

Figure 1:
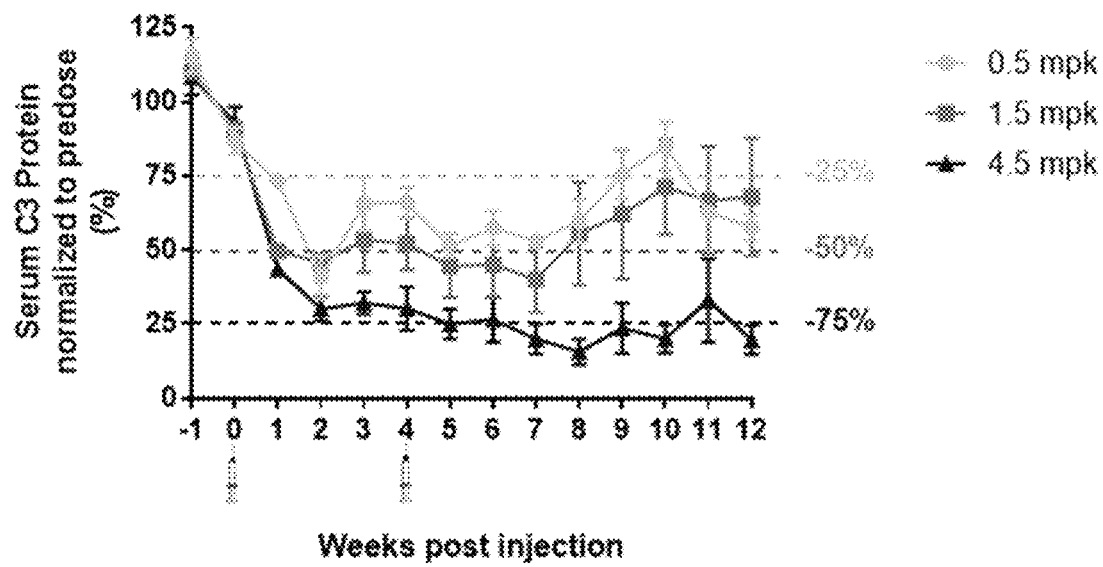
FIG. 1. Graph showing serum cynomolgus monkey C3 protein levels normalized to pre-dose, pursuant to the study described in Example 2.

The disclosed RNAi agents, compositions thereof, and methods of use may be understood more readily by reference to the following detailed description, which form a part of this disclosure. It is to be understood that the disclosure is not limited to what is specifically described and/or shown herein, and that the terminology used herein is for the purpose of describing particular embodiments by way of example only and is not intended to be limiting.

It is to be appreciated that while certain features of the disclosures included herein are, for clarity, described herein in the context of separate embodiments, they may also be provided in combination in a single embodiment. Conversely, various features of the disclosed methods that are, for brevity, described in the context of a single embodiment, may also be provided separately or in any subcombination.

Definitions

As used herein, an "RNAi agent" means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. C3 mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature. A nucleic acid molecule can comprise unmodified and/or modified nucleotides. A nucleotide sequence can comprise unmodified and/or modified nucleotides.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, the term "nucleotide" has the same meaning as commonly understood in the art. Thus, the term "nucleotide" as used herein, refers to a glycoside comprising a sugar moiety, a base moiety and a covalently linked group (linkage group), such as a phosphate or phosphorothioate internucleoside linkage group, and covers both naturally occurring nucleotides, such as DNA or RNA, and non-naturally occurring nucleotides comprising modified sugar and/or base moieties, which are also referred to as nucleotide analogs herein. Herein, a single nucleotide can be referred to as a monomer or unit.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or otherwise suitable in vivo or in vitro conditions)) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of an MUC5AC mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "individual", "patient" and "subject", are used interchangeably to refer to a member of any animal species including, but not limited to, birds, humans and other primates, and other mammals including commercially relevant mammals or animal models such as mice, rats, monkeys, cattle, pigs, horses, sheep, cats, and dogs. Preferably, the subject is a human.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol ⌇ as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art. Correspondingly, compounds described herein with labile protons or basic atoms should also be understood to represent salt forms of the corresponding compound. Compounds described herein may be in a free acid, free base, or salt form. Pharmaceutically acceptable salts of the compounds described herein should be understood to be within the scope of the invention.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Where a value is explicitly recited, it is to be understood that values which are about the same quantity or amount as the recited value are also within the scope of the disclosure. Where a combination is disclosed, each sub-combination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Other objects, features, aspects, and advantages of the invention will be apparent from the following detailed description, accompanying figures, and from the claims.

DETAILED DESCRIPTION

RNAi Agents

Described herein are RNAi agents for inhibiting expression of a C3 gene. Each C3 RNAi agent comprises a sense strand and an antisense strand. The sense strand can be 15 to 49 nucleotides in length. The antisense strand can be 21 to 49 nucleotides in length. The sense and antisense strands can be either the same length or they can be different lengths. In some embodiments, the sense and antisense strands are each independently 21 to 27 nucleotides in length. In some embodiments, both the sense and antisense strands are each 21-26 nucleotides in length. In some embodiments, the sense and antisense strands are each 21-24 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent antisense strands are each independently 21, 22, 23, 24, 25, 26, 27, 28, 29, or 30 nucleotides in length. In some embodiments, the RNAi agent sense strands are each independently 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. The sense and antisense strands are annealed to form a duplex, and in some embodiments, a double-stranded RNAi agent has a duplex length of about 15, 16, 17, 18, 19, 20, 21, 22, 23, 24, 25, 26, 27, 28, 29, or 30 nucleotides.

Examples of nucleotide sequences used in forming C3 RNAi agents are provided in Tables 2, 3, 4, 5C, 7A, 7B, and 8. Examples of RNAi agent duplexes, that include the sense strand and antisense strand sequences in Tables 2, 3, 4, 5C, 7A, and 7B, are shown in Tables 5A, 5B, 5C, and 8.

In some embodiments, the region of perfect, substantial, or partial complementarity between the sense strand and the antisense strand is 15-26 (e.g., 15, 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

A sense strand of the C3 RNAi agents described herein includes at least 15 consecutive nucleotides that have at least 85% identity to a core stretch sequence (also referred to herein as a "core stretch" or "core sequence") of the same number of nucleotides in a C3 mRNA. In some embodiments, a sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence of the same length (sometimes referred to, e.g., as a target sequence) present in the C3 mRNA target. In some embodiments, this sense strand core stretch is 15, 16, 17, 18, 19, 20, 21, 22, or 23 nucleotides in length. In some embodiments, this sense strand core stretch is 17 nucleotides in length. In some embodiments, this sense strand core stretch is 19 nucleotides in length. In some embodiments, this sense strand core stretch is 21 nucleotides in length.

An antisense strand of a C3 RNAi agent described herein includes at least 15 consecutive nucleotides that have at least 85% complementarity to a core stretch of the same number of nucleotides in a C3 mRNA and to a core stretch of the same number of nucleotides in the corresponding sense strand. In some embodiments, an antisense strand core stretch is 100% (perfectly) complementary or at least about 85% (substantially) complementary to a nucleotide sequence (e.g., target sequence) of the same length present in the C3 mRNA target. In some embodiments, this antisense strand core stretch is 15, 16, 17, 18, 19, 20, 21, 22, or 23 nucleotides in length. In some embodiments, this antisense strand core stretch is 21 nucleotides in length. In some embodiments, this antisense strand core stretch is 19 nucleotides in length. A sense strand core stretch sequence can be the same length as a corresponding antisense core sequence or it can be a different length.

The C3 RNAi agent sense and antisense strands anneal to form a duplex. A sense strand and an antisense strand of a C3 RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 15, at least 16, at least 17, at least 18, at least 19, at least 20, at least 21, at least 22, at least 23, at least 24, or at least 25 nucleotides that is at least 85% or 100% complementary to a corresponding 15, 16, 17, 18, 19, 20, 21, 22, 23, 24, or 25 nucleotide sequence of the antisense strand core stretch sequence (i.e., the sense and antisense core stretch sequences of a C3 RNAi agent have a region of at least 15, at least 16, at least 17, at least 18, at least 19, at least 20, at least 21, at least 22, at least 23, at least 24, or at least 25 nucleotides that is at least 85% base paired or 100% base paired.)

In some embodiments, the antisense strand of a C3 RNAi agent disclosed herein differs by 0, 1, 2, or 3 nucleotides from any of the antisense strand sequences in Table 2, Table 3, Table 5C, Table 7A, or Table 8. In some embodiments, the sense strand of a C3 RNAi agent disclosed herein differs by 0, 1, 2, or 3 nucleotides from any of the sense strand sequences in Table 2, Table 4, Table 5C, Table 7B, or Table 8.

In some embodiments, the sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the C3 mRNA. The sense strand additional nucleotides, if present, may or may not be identical to the corresponding sequence in the C3 mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, a C3 RNAi agent has an antisense strand having a 3' extension and a sense strand having a 5' extension. In some embodiments, the extension nucleotide(s) are unpaired and form an overhang. As used herein and in the art, an "overhang" refers to an extension of a stretch of one or more unpaired nucleotides located at a terminal end of either the sense strand or the antisense strand that does not form part of the hybridized or duplexed portion of an RNAi agent disclosed herein.

In some embodiments, a C3 RNAi agent comprises an antisense strand having a 3' extension of 1, 2, 3, 4, 5, or 6 nucleotides in length. In other embodiments, a C3 RNAi agent comprises an antisense strand having a 3' extension of 1, 2, or 3 nucleotides in length. In some embodiments, one or more of the antisense strand extension nucleotides comprise nucleotides that are complementary to the corresponding C3 mRNA sequence. In some embodiments, one or more of the antisense strand extension nucleotides comprise nucleotides that are not complementary to the corresponding C3 mRNA sequence.

In some embodiments, a C3 RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to or are the identical to nucleotides in the C3 mRNA sequence. In some embodiments, the 3' sense strand extension includes or consists of one of the following sequences, but is not limited to: T, UT, TT, UU, UUT, TTT, or TTTT (each listed 5' to 3').

A sense strand can have a 3' extension and/or a 5' extension. In some embodiments, a C3 RNAi agent comprises a sense strand having a 5' extension of 1, 2, 3, 4, 5, or 6 nucleotides in length. In some embodiments, one or more of the sense strand extension nucleotides comprise nucleotides that correspond to or are identical to nucleotides in the C3 mRNA sequence.

Examples of sequences used in forming C3 RNAi agents are provided in Tables 2, 3, 4, 5C, 7A, 7B, and 8. In some embodiments, a C3 RNAi agent antisense strand includes a sequence of any of the sequences in Tables 2, 3, 5C, 7A, or 8. In certain embodiments, a C3 RNAi agent antisense strand comprises or consists of any one of the modified sequences in Table 3. In some embodiments, a C3 RNAi agent antisense strand includes the sequence of nucleotides (from 5' end→3' end) 1-17, 2-15, 2-17, 1-18, 2-18, 1-19, 2-19, 1-20, 2-20, 1-21, or 2-21, of any of the sequences in Tables 2, 3, 5C, 7A, or 8. In some embodiments, a C3 RNAi agent sense strand includes the sequence of any of the sequences in Tables 2, 4, 5C, 7B, or 8. In some embodiments, a C3 RNAi agent sense strand includes the sequence of nucleotides (from 5' end→3' end) 1-18, 1-19, 1-20, 1-21, 2-19, 2-20, 2-21, 3-20, 3-21, or 4-21 of any of the sequences in Tables 2, 4, 5C, 7B, or 8. In certain embodiments, a C3 RNAi agent sense strand comprises or consists of a modified sequence of any one of the modified sequences in Table 4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

The C3 RNAi agents disclosed herein may also be comprised of one or more modified nucleotides. In some embodiments, substantially all of the nucleotides of the sense strand and substantially all of the nucleotides of the antisense strand of the C3 RNAi agent are modified nucleotides. The C3 RNAi agents disclosed herein may further be comprised of one or more modified internucleoside linkages, e.g., one or more phosphorothioate linkages. In some embodiments, a C3 RNAi agent contains one or more modified nucleotides and one or more modified internucleoside linkages. In some embodiments, a 2'-modified nucleotide is combined with modified internucleoside linkage.

In some embodiments, a C3 RNAi agent is prepared or provided as a salt, mixed salt, or a free-acid. In some embodiments, a C3 RNAi agent is prepared as a pharmaceutically acceptable salt. In some embodiments, a C3 RNAi agent is prepared as a pharmaceutically acceptable sodium salt. Such forms that are well known in the art are within the scope of the inventions disclosed herein.

Modified Nucleotides

Modified nucleotides, when used in various oligonucleotide constructs, can preserve activity of the compound in cells while at the same time increasing the serum stability of these compounds, and can also minimize the possibility of activating interferon activity in humans upon administering of the oligonucleotide construct.

In some embodiments, a C3 RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e., a nucleotide with a group other than a hydroxyl group at the 2' position of the five-membered sugar ring) include, but are not limited to, 2'-O-methyl nucleotides (also referred to herein or in the art as 2'-methoxy nucleotides), 2'-fluoro nucleotides (also referred to herein or in the art as 2'-deoxy-2'-fluoro nucleotides), 2'-deoxy nucleotides, 2'-methoxyethyl (2'-O-2-methoxylethyl) nucleotides (also referred herein or in the art as 2'-MOE nucleotides), 2'-amino nucleotides, and 2'-alkyl nucleotides. It is not necessary for all positions in a given compound to be uniformly modified. Conversely, more than one modification can be incorporated in a single C3 RNAi agent or even in a single nucleotide thereof. The C3 RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrinidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulflydryl, 8-thioalkyl, 8-hydroxyl and other 8-substituted adenines and guanines, 5-halo (e.g., 5-brono), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, the 5' and/or 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. In some embodiments, an abasic residue can be placed internally in a nucleotide sequence. In some embodiments, Ab or AbAb can be added to the 3' end of the antisense strand. In some embodiments, the 5' end of the sense strand can include one or more additional abasic residues (e.g., (Ab) or (AbAb)). In some embodiments, UUAb, UAb, or Ab are added to the 3' end of the sense strand. In some embodiments, an abasic (deoxyribose) residue can be replaced with a ribitol (abasic ribose) residue.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide. Chemical structures for certain modified nucleotides are set forth in Table 6 herein.

Modified Internucleoside Linkages

In some embodiments, one or more nucleotides of a C3 RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of a C3 RNAi agent can contain 1, 2, 3, 4, 5, or 6 phosphorothioate linkages, an antisense strand of a C3 RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of a C3 RNAi agent can contain 1, 2, 3, or 4 phosphorothioate linkages, an antisense strand of a C3 RNAi agent can contain 1, 2, 3, or 4 phosphorothioate linkages, or both the sense strand and the antisense strand independently can contain 1, 2, 3, or 4 phosphorothioate linkages.

In some embodiments, a C3 RNAi agent sense strand contains at least two phosphorothioate internucleoside linkages. In some embodiments, the phosphorothioate internucleoside linkages are between the nucleotides at positions 1-3 from the 3' end of the sense strand. In some embodiments, one phosphorothioate internucleoside linkage is at the 5' end of the sense strand nucleotide sequence, and another phosphorothioate linkage is at the 3' end of the sense strand nucleotide sequence. In some embodiments, two phosphorothioate internucleoside linkages are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, a C3 RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, a C3 RNAi agent contains at least three or four phosphorothioate internucleoside linkages in the antisense strand.

Capping Residues or Moieties

In some embodiments, the sense strand may include one or more capping residues or moieties, sometimes referred to in the art as a "cap," a "terminal cap," or a "capping residue." As used herein, a "capping residue" is a non-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some embodiments, inverted abasic residues (invAb) (also referred to in the art as "inverted abasic sites") are added as capping residues. (See, e.g., F. Czauderna, Nucleic Acids Res., 2003, 31(11), 2705-16; U.S. Pat. No. 5,998,203). Capping residues are generally known in the art, and include, for example, inverted abasic residues as well as carbon chains such as a terminal $C_3H_7$ (propyl), $C_6H_{13}$ (hexyl), or $C_{12}H_{25}$ (dodecyl) groups. In some embodiments, a capping residue is present at either the 5' terminal end, the 3' terminal end, or both the 5' and 3' terminal ends of the sense strand. In some embodiments, the 5' end and/or the 3' end of the sense strand may include more than one inverted abasic deoxyribose moiety as a capping residue.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s)), or other internucleoside linkages. In some embodiments, the inclusion of one or more inverted abasic residues at or near the terminal end or terminal ends of the sense strand of an RNAi agent may allow for enhanced activity or other desired properties of an RNAi agent. In some embodiments, an inverted abasic (deoxyribose) residue can be replaced with an inverted ribitol (abasic ribose) residue. In some embodiments, the 3' end of the antisense strand core stretch sequence, or the 3' end of the antisense strand sequence, may include an inverted abasic residue. The chemical structures for inverted abasic deoxyribose residues are shown in Table 6 below.

C3 RNAi Agents

The C3 RNAi agents disclosed herein are designed to target specific positions on a C3 gene (e.g., SEQ ID NO: 1).

```
       NM_000064.4 Homo sapiens complement C3, mRNA transcript
                         (SEQ ID NO: 1):

1  actcctcccc atcctctccc tctgtccctc tgtccctctg accctgcact gtcccagcac 61  catgggaccc acctcaggtc ccagcctgct gctcctgcta ctaacccacc tcccctggc 121  tctggggagt cccatgtact ctatcatcac ccccaacatc ttgcggctgg agagcgagga 181  gaccatggtg ctggaggccc acgacgcgca aggggatgtt ccagtcactg ttactgtcca 241  cgacttccca ggcaaaaaac tagtgctgtc cagtgagaag actgtgctga ccctgccac 301  caaccacatg ggcaacgtca ccttcacgat cccagccaac agggagttca agtcagaaaa 361  ggggcgcaac aagttcgtga ccgtgcaggc caccttcggg acccaagtgg tggagaaggt 421  ggtgctggtc agcctgcaga gcgggtacct cttcatccag acagacaaga ccatctacac 481  ccctggctcc acagttctct atcggatctt caccgtcaac cacaagctgc tacccgtggg 541  ccggacggtc atggtcaaca ttgagaaccc ggaaggcatc ccggtcaagc aggactcctt 601  gtcttctcag aaccagcttg gcgtcttgcc cttgtcttgg gacattccgg aactcgtcaa 661  catgggccag tggaagatcc gagcctacta tgaaaactca ccacagcagg tcttctccac 721  tgagtttgag gtgaaggagt acgtgctgcc cagtttcgag gtcatagtgg agcctacaga 781  gaaattctac tacatctata acgagaaggg cctggaggtc accatcaccg ccaggttcct 841  ctacgggaag aaagtggagg gaactgcctt tgtcatcttc gggatccagg atggcgaaca 901  gaggatttcc ctgcctgaat ccctcaagcg cattccgatt gaggatggct cgggggaggt 961  tgtgctgagc cggaaggtac tgctggacgg ggtgcagaac ccccgagcag aagacctggt 1021  ggggaagtct ttgtacgtgt ctgccaccgt catcttgcac tcaggcagtg acatggtgca 1081  ggcagagcgc agcgggatcc ccatcgtgac ctctccctac cagatccact tcaccaagac 1141  acccaagtac ttcaaaccag gaatgccctt tgacctcatg gtgttcgtga cgaaccctga 1201  tggctctcca gcctaccgag tccccgtggc agtccagggc gaggacactg tgcagtctct 1261  aacccaggga gatggcgtgg ccaaactcag catcaacaca caccccagcc agaagccctt 1321  gagcatcacg gtgcgcacga agaagcagga gctctcggag gcagagcagg ctaccaggac
```

NM_000064.4 *Homo sapiens* complement C3, mRNA transcript
(SEQ ID NO: 1):

```
1381 catgcaggct ctgccctaca gcaccgtggg caactccaac aattacctgc atctctcagt
1441 gctacgtaca gagctcagac ccggggagac cctcaacgtc aacttcctcc tgcgaatgga
1501 ccgcgcccac gaggccaaga tccgctacta cacctacctg atcatgaaca agggcaggct
1561 gttgaaggcg ggacgccagg tgcgagagcc cggccaggac ctggtggtgc tgccCctgtc
1621 catcaccacc gacttcatcc cttccttccg cctggtggcg tactacacgc tgatcggtgc
1681 cagcggccag agggaggtgg tggccgactc cgtgtgggtg gacgtcaagg actcctgcgt
1741 gggctcgctg gtggtaaaaa gcggccagtc agaagaccgg cagcctgtac ctgggcagca
1801 gatgaccctg aagatagagg gtgaccacgg ggcccgggtg gtactggtgg ccgtggacaa
1861 gggcgtgttc gtgctgaata agaagaacaa actgacgcag agtaagatct gggacgtggt
1921 ggagaaggca gacatcggct gcaccccggg cagtgggaag gattacgccg tgtcttctc
1981 cgacgcaggg ctgaccttca cgagcagcag tggccagcag accgcccaga ggcagaact
2041 tcagtgcccg cagccagccg cccgccgacg ccgttccgtg cagctcacgg agaagcgaat
2101 ggacaaagtc ggcaagtacc ccaaggagct gcgcaagtgc tgcgaggacg gcatgcggga
2161 gaaccccatg aggttctcgt gccagcgccg gacccgtttc atctccctgg gcgaggcgtg
2221 caagaaggtc ttcctggact gctgcaacta catcacagag ctgcggcggc agcacgcgcg
2281 ggccagccac ctgggcctgg ccaggagtaa cctggatgag gacatcattg cagaagagaa
2341 catcgtttcc cgaagtgagt cccagagag ctggctgtgg aacgttgagg acttgaaaga
2401 gccaccgaaa aatggaatct ctacgaagct catgaatata ttttgaaag actccatcac
2461 cacgtgggag attctggctg tgagcatgtc ggacaagaaa gggatctgtg tggcagaccc
2521 cttcgaggtc acagtaatgc aggacttctt catcgacctg cggctaccct actctgttgt
2581 tcgaaacgag caggtggaaa tccgagccgt tctctacaat taccggcaga accaagagct
2641 caaggtgagg gtggaactac tccacaatcc agccttctgc agcctggcca ccaccaagag
2701 gcgtcaccag cagacgctaa ccatcccccc caagtcctcg ttgtccgtt catatgtcat
2761 cgtgccgcta aagaccggcc tgcaggaagt ggaagtcaag gctgctgtct accatcattt
2821 catcagtgac ggtgtcagga agtccctgaa ggtcgtgccg gaaggaatca gaatgaacaa
2881 aactgtggct gttcgcaccc tggatccaga acgcctgggc cgtgaaggag tgcagaaaga
2941 ggacatccca cctgcagacc tcagtgacca agtcccggac accgagtctg agaccagaat
3001 tctcctgcaa gggacccag tggcccagat gacagaggat gccgtcgacg cggaacggct
3061 gaagcacctc attgtgaccc cctcgggctg cggggaacag aacatgatcg gcatgacgcc
3121 cacggtcatc gctgtgcatt acctggatga aacggagcag tgggagaagt tcggcctaga
3181 gaagcggcag ggggccttgg agctcatcaa gaagggtac acccagcagc tggccttcag
3241 acaacccagc tctgcctttg cggcttgtg aaacgggca cccagcacct ggctgaccgc
3301 ctacgtggtc aaggtcttct ctctggctgt caacctcatc gccatcgact cccaagtcct
3361 ctgcggggct gttaaatggc tgatcctgga gaagcagaag cccgacgggg tcttccagga
3421 ggatgcgccc gtgatacacc aagaaatgat tggtggatta cggaacaaca acgagaaaga
3481 catggccctc acggcctttg ttctcatctc gctgcaggag gctaaagata tttgcgagga
3541 gcaggtcaac agcctgccag gcagcatcac taaagcagga gacttccttg aagccaacta
3601 catgaaccta cagagatcct acactgtggc cattgctggc tatgctctgg cccagatggg
```

-continued

NM_000064.4 *Homo sapiens* complement C3, mRNA transcript
(SEQ ID NO: 1):

```
3661 caggctgaag gggcctcttc ttaacaaatt tctgaccaca gccaaagata agaaccgctg 3721 ggaggaccct ggtaagcagc tctacaacgt ggaggccaca tcctatgccc tcttggccct 3781 actgcagcta aaagactttg actttgtgcc tcccgtcgtg cgttggctca atgaacagag 3841 atactacggt ggtggctatg gctctaccca ggccaccttc atggtgttcc aagccttggc 3901 tcaataccaa aaggacgccc ctgaccacca ggaactgaac cttgatgtgt ccctccaact 3961 gcccagccgc agctccaaga tcacccacg tatccactgg aatctgcca gcctcctgcg 4021 atcagaagag accaaggaaa atgagggttt cacagtcaca gctgaaggaa aaggccaagg 4081 caccttgtcg gtggtgacaa tgtaccatgc taaggccaaa gatcaactca cctgtaataa 4141 attcgacctc aaggtcacca taaaccagc accggaaaca gaaaagaggc ctcaggatgc 4201 caagaacact atgatccttg agatctgtac caggtaccgg ggagaccagg atgccactat 4261 gtctatattg gacatatcca tgatgactgg ctttgctcca gacacagatg acctgaagca 4321 gctggccaat ggtgttgaca gatacatctc caagtatgag ctggacaaag ccttctccga 4381 taggaacacc ctcatcatct acctggacaa ggtctcacac tctgaggatg actgtctagc 4441 tttcaaagtt caccaatact ttaatgtaga gcttatccag cctggagcag tcaaggtcta 4501 cgcctattac aacctggagg aaagctgtac ccggttctac catccggaaa aggaggatgg 4561 aaagctgaac aagctctgcc gtgatgaact gtgccgctgt gctgaggaga attgcttcat 4621 acaaaagtcg gatgacaagg tcaccctgga agaacggctg gacaaggcct gtgagccagg 4681 agtggactat gtgtacaaga cccgactggt caaggttcag ctgtccaatg actttgacga 4741 gtacatcatg gccattgagc agaccatcaa gtcaggctcg gatgaggtgc aggttggaca 4801 gcagcgcacg ttcatcagcc ccatcaagtg cagagaagcc ctgaagctgg aggagaagaa 4861 acactacctc atgtggggtc tctcctccga tttctgggga gagaagccca acctcagcta 4921 catcatcggg aaggacactt gggtggagca ctggcccgag gaggacgaat gccaagacga 4981 agagaaccag aaacaatgcc aggacctegg cgccttcacc gagagcatgg ttgtctttgg 5041 gtgccccaac tgaccacacc cccattcccc cactccagat aaagcttcag ttatatctca 5101 cgtgtctgga gttctttgcc aagagggaga ggctgaaatc cccagccgcc tcacctgcag 5161 ctcagctcca tcctacttga aacctcacct gttcccaceg cattttctcc tggcgttcgc 5221 ctgctagtgt g
```

As defined herein, an antisense strand sequence is designed to target a C3 gene at a given position on the gene when the 5' terminal nucleobase of the antisense strand is aligned with a position that is 21 nucleotides downstream (towards the 3' end) from the position on the gene when base pairing to the gene. For example, as illustrated in Tables 1 and 2 herein, an antisense strand sequence designed to target a C3 gene at position 2566 requires that when base pairing to the gene, the 5' terminal nucleobase of the antisense strand is aligned with position 2586 of the C3 gene.

As provided herein, a C3 RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 15 consecutive nucleotides. For example, for a C3 RNAi agent disclosed herein that is designed to target position 2566 of a C3 gene, the 5' terminal nucleobase of the antisense strand of the of the C3 RNAi agent must be aligned with position 2586 of the gene; however, the 5' terminal nucleobase of the antisense strand may be, but is not required to be, complementary to position 2586 of a C3 gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 15 consecutive nucleotides. As shown by, among other things, the examples disclosed herein and as is well known in the art, the specific site of binding of the gene by the antisense strand of the C3 RNAi agent (e.g., whether the C3 RNAi agent is designed to target a C3 gene at position 2566 or at some other position) is important to the level of inhibition achieved by the C3 RNAi agent as well as the toxicity profile achieved by the molecule. (See, e.g., Kamola et al., *The siRNA Non-seed Region and Its Target Sequences are Auxiliary Determinants of Off-Target Effects*, PLOS Computational Biology, 11(12), FIG. 1 (2015)).

In some embodiments, the C3 RNAi agents disclosed herein target a C3 gene at or near the positions of the C3 gene sequence shown in Table 1. In some embodiments, the antisense strand of a C3 RNAi agent disclosed herein includes a core stretch sequence that is fully, substantially, or at least partially complementary to a target C3 21-mer sequence disclosed in Table 1.

TABLE 1

C3 21-mer mRNA Target Sequences (taken from homo sapiens complement C3, mRNA, GenBank NM_000064.4 (SEQ ID NO:1))

| SEQ ID No. | C3 21-mer Target Sequences (5' → 3') | Corresponding Positions of Sequence on SEQ ID NO: 1 | Targeted Gene Position (as referred to herein) |
|---|---|---|---|
| 2 | ACCCUACUCUGUUGUUCGAAA | 2566-2586 | 2566 |

In some embodiments, a C3 RNAi agent includes an antisense strand wherein position 21 of the antisense strand (5'→3') is capable of forming a base pair with position 1 of a 21-mer target sequence disclosed in Table 1. In some embodiments, a C3 RNAi agent includes an antisense strand wherein position 1 of the antisense strand (5'→3') is capable of forming a base pair with position 21 of the 21-mer target sequence disclosed in Table 1.

In some embodiments, a C3 RNAi agent includes an antisense strand wherein position 2 of the antisense strand (5'→3') is capable of forming a base pair with position 20 of the 21-mer target sequence disclosed in Table 1. In some embodiments, a C3 RNAi agent includes an antisense strand wherein positions 2 through 18 of the antisense strand (5'→3') are capable of forming base pairs with each of the respective complementary bases located at positions 18 through 2 of the 21-mer target sequence disclosed in Table 1.

For the RNAi agents disclosed herein, the nucleotide at position 1 of the antisense strand (from 5' end→3' end) can be perfectly complementary to the C3 gene, or can be non-complementary to the C3 gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, a C3 RNAi agent antisense strand comprises the sequence of nucleotides (from 5' end→3' end) 2-18, 2-19, 2-20, or 2-21 of any of the antisense strand sequences in Table 2, Table 3, Table 5C, Table 7A, or Table 8. In some embodiments, a C3 RNAi sense strand comprises the sequence of nucleotides (from 5' end→3' end) 3-21, 2-21, 1-21, 3-20, 2-20, 1-20, 3-19, 2-19, 1-19, 3-18, 2-18, or 1-18 of any of the sense strand sequences in Table 2, Table 4, Table 5C, Table 7B, or Table 8.

In some embodiments, a C3 RNAi agent antisense strand comprises the sequence of nucleotides (from 5' end→3' end) 2-18, 2-19, 2-20, or 2-21 of any of the antisense strand sequences of Table 2, Table 3, Table 5C, Table 7A, or Table 8. In some embodiments, a C3 RNAi sense strand comprises the sequence of nucleotides (from 5' end→3' end) 3-21, 2-21, 1-21, 3-20, 2-20, 1-20, 3-19, 2-19, 1-19, 3-18, 2-18, or 1-18 of any of the sense strand sequences of Table 2, Table 4, Table 5C, Table 7B, or Table 8.

In some embodiments, a C3 RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 3-21, 2-21, 1-21, 3-20, 2-20, 1-20, 3-19, 2-19, 1-19, 3-18, 2-18, or 1-18 of any of the sense strand sequences in Table 2 or Table 4.

In some embodiments, a C3 RNAi agent is comprised of (i) an antisense strand comprising the sequence of nucleotides (from 5' end→3' end) 2-18 or 2-19 of any of the antisense strand sequences of Table 2 or Table 3, and (ii) a sense strand comprising the sequence of nucleotides (from 5' end→3' end) 3-21, 2-21, 1-21, 3-20, 2-20, 1-20, 3-19, 2-19, 1-19, 3-18, 2-18, or 1-18 of any of the sense strand sequences of Table 2 or Table 4.

In some embodiments, the C3 RNAi agents include core 21-mer nucleotide sequences shown in the following Table 2.

C3 RNAi Agent Antisense Strand and Sense Strand Core Stretch Base Sequences

| SEQ ID No. | Antisense Strand Sequence (5' → 3') (Shown as an Umodified Nucleotide Sequence) | SEQ ID No. | Sense Strand Sequence (5' → 3') (Shown as an Umodified Nucleotide Sequence) | Corresponding Positions of Identified Sequence on SEQ ID NO: 1 | Targeted Gene Position |
|---|---|---|---|---|---|
| 3 | UUUCGAACAACAGAGUAGGGU | 8 | ACCCUACUCUGUUGUUCGAAA | 2566-2586 | 2566 |
| 4 | AUUCGAACAACAGAGUAGGGU | 9 | ACCCUACUCUGUUGUUCGAAU | 2566-2586 | 2566 |
| 5 | NUUCGAACAACAGAGUAGGGU | 10 | ACCCUACUCUGUUGUUCGAAN | 2566-2586 | 2566 |
| 6 | UUUCGAACAACAGAGUAGGGN | 11 | NCCCUACUCUGUUGUUCGAAA | 2566-2586 | 2566 |
| 7 | NUUCGAACAACAGAGUAGGGN | 12 | NCCCUACUCUGUUGUUCGAAN | 2566-2586 | 2566 |

(N = any nucleobase;)

The C3 RNAi agent sense strands and antisense strands that comprise or consist of the sequences in Table 2 can be modified nucleotides or unmodified nucleotides. In some embodiments, the C3 RNAi agents having the sense and antisense strand sequences that comprise or consist of the sequences in Table 2 are all or substantially all modified nucleotides.

In some embodiments, the antisense strand of a C3 RNAi agent disclosed herein differs by 0, 1, 2, or 3 nucleotides from any of the antisense strand sequences in Table 2. In some embodiments, the sense strand of a C3 RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified C3 RNAi agent antisense strands, as well as their underlying unmodified nucleobase sequences, are provided in Table 3. Certain modified C3 RNAi agent sense strands, as well as their underlying unmodified nucleobase sequences, are provided in Table 4. In forming C3 RNAi agents, each of the nucleotides in each of the underlying base sequences listed in Tables 3 and 4, as well as in Table 2, above, can be a modified nucleotide.

The C3 RNAi agents described herein are formed by annealing an antisense strand with a sense strand. A sense strand containing a sequence listed in Table 2 or Table 4, can be hybridized to any antisense strand containing a sequence listed in Table 2 or Table 3, provided the two sequences have a region of at least 85% complementarity over a contiguous 15, 16, 17, 18, 19, 20, or 21 nucleotide sequence.

In some embodiments, a C3 RNAi agent antisense strand comprises a nucleotide sequence of any of the sequences in Table 2 or Table 3.

In some embodiments, a C3 RNAi agent comprises or consists of a duplex having the nucleobase sequences of the sense strand and the antisense strand of any of the sequences in Table 2, Table 3 or Table 4. In some embodiments, a C3 RNAi agent comprises or consists of a duplex sequence prepared or provided as a sodium salt, mixed salt, or a free-acid.

Examples of antisense strands containing modified nucleotides are provided in Table 3 and Table 5C. Examples of sense strands containing modified nucleotides are provided in Table 4 and Table 5C.

As used in Tables 3, 4, 5C, 7A, 7B, and 8, the following notations are used to indicate modified nucleotides and linking groups:

A=adenosine-3'-phosphate;
C=cytidine-3'-phosphate;
G=guanosine-3'-phosphate;
U=uridine-3'-phosphate
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
u=2'-O-methyluridine-3'-phosphate
us=2'-O-methyluridine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Uf=2'-fluorouridine-3'-phosphate
Ufs=2'-fluorouridine-3'-phosphorothioate
(invAb)=inverted abasic deoxyribonucleotide, see Table 6
(invAb)s=inverted abasic deoxyribonucleotide-5'-phosphorothioate, see Table 6
cPrpa=5'-cyclopropyl phosphonate-2'-O-methyladenosine-3'-phosphate (see Table 6)
cPrpas=5'-cyclopropyl phosphonate-2'-O-methyladenosine-3'-phosphorothioate (see Table 6)
cPrpu=5'-cyclopropyl phosphonate-2'-O-methyluridine-3'-phosphate (see Table 6)
cPrpus=5'-cyclopropyl phosphonate-2'-O-methyluridine-3'-phosphorothioate (see Table 6)

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the embodiments disclosed herein, when viewing the respective strand 5'→3', the inverted abasic residues are inserted such that the 3' position of the deoxyribose is linked at the 3' end of the preceding monomer on the respective strand (see, e.g., Table 6). Moreover, as the person of ordinary skill would readily understand and appreciate, while the phosphorothioate chemical structures depicted herein typically show the anion on the sulfur atom, the inventions disclosed herein encompass all phosphorothioate tautomers and resonance structures (e.g., where the sulfur atom has a double-bond and the anion is on an oxygen atom). Unless expressly indicated otherwise herein, such understandings of the person of ordinary skill in the art are used when describing the C3 RNAi agents and compositions of C3 RNAi agents disclosed herein.

Certain examples of targeting ligands, targeting groups, and linking groups used with the C3 RNAi agents disclosed herein are provided below in Table 6. More specifically, targeting groups and linking groups (which together can form a targeting ligand) include (NAG37) and (NAG37)s, for which their chemical structures are provided below in Table 6. Each sense strand and/or antisense strand can have any targeting ligands, targeting groups, or linking groups listed herein, as well as other groups, conjugated to the 5' and/or 3' end of the sequence.

TABLE 3

C3 RNAi Agent Antisense Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM13561-AS | usUfsusCfgAfacaacAfgAfgUfaGfGfgsu | 13 | UUUCGAACAACAGAGUAGGGU | 3 |

TABLE 4A

C3 RNAi Agent Sense Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM12489-SS | (NAG37)s(invAb)sacccuacuCfUfGfuuguucgaaas(invAb) | 14 | ACCCUACUCUGUUGUUCGAAA | 8 |

TABLE 4B

C3 RNAi Agent Sense Strand Sequences (without targeting ligands or end caps)

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM12489-SS | acccuacuCfUfGfuuguucgaaa | 15 | ACCCUACUCUGUUGUUCGAAA | 8 |

The C3 RNAi agents described herein are formed by annealing an antisense strand with a sense strand. A sense strand containing a sequence listed in Table 2, Table 4, Table 5C, Table 7B, or Table 8 can be hybridized to any antisense strand containing a sequence listed in Table 2, Table 3, Table 5C, Table 7A, or Table 8 provided the two sequences have a region of at least 85% complementarity over a contiguous 15, 16, 17, 18, 19, 20, or 21 nucleotide sequence.

In some embodiments, the antisense strand of a C3 RNAi agent disclosed herein differs by 0, 1, 2, or 3 nucleotides from any of the antisense strand sequences in Table 3 or Table 5C. In some embodiments, the sense strand of a C3 RNAi agent disclosed herein differs by 0, 1, 2, or 3 nucleotides from any of the sense strand sequences in Table 4 or Table 5C.

In some embodiments, a C3 RNAi agent antisense strand comprises a nucleotide sequence of any of the sequences in Table 2, Table 3, or Table 5C. In some embodiments, a C3 RNAi agent antisense strand comprises the sequence of nucleotides (from 5' end→3' end) 1-17, 2-17, 1-18, 2-18, 1-19, 2-19, 1-20, 2-20, 1-21, or 2-21, of any of the sequences in Table 2, Table 3, or Table 5C. In certain embodiments, a C3 RNAi agent antisense strand comprises or consists of a modified sequence of any one of the modified sequences in Table 3 or Table 5C.

In some embodiments, a C3 RNAi agent sense strand comprises the nucleotide sequence of any of the sequences in Table 2, Table 4, or Table 5C. In some embodiments, a C3 RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, or 4-21, of any of the sequences in Table 2, Table 4, or Table 5C. In certain embodiments, a C3 RNAi agent sense strand comprises or consists of a modified sequence of any one of the modified sequences in Table 4 or Table 5C.

For the C3 RNAi agents disclosed herein, the nucleotide at position 1 of the antisense strand (from 5' end→3' end) can be perfectly complementary to a C3 gene, or can be non-complementary to a C3 gene. In some embodiments, the nucleotide at position 1 of the antisense strand (from 5' end→3' end) is a U, A, or dT (or a modified version thereof). In some embodiments, the nucleotide at position 1 of the antisense strand (from 5' end→3' end) forms an A:U or U:A base pair with the sense strand.

A sense strand containing a sequence listed in Table 2, Table 4, Table 5C, Table 7B, or Table 8 can be hybridized to any antisense strand containing a sequence listed in Table 2, Table 3, Table 5C, Table 7A, or Table 8 provided the two sequences have a region of at least 85% complementarity over a contiguous 15, 16, 17, 18, 19, 20, or 21 nucleotide sequence. In some embodiments, the C3 RNAi agent has a sense strand consisting of the modified sequence of any of the modified sequences in Table 4 or Table 5C, and an antisense strand consisting of the modified sequence of any of the modified sequences in Table 3 or Table 5C. Certain representative sequence pairings are exemplified by the Duplex ID Nos. shown in Tables 5A, 5B, 5C, and 8.

In some embodiments, a C3 RNAi agent comprises, consists of, or consists essentially of a duplex represented by any one of the Duplex ID Nos. presented herein. In some embodiments, a C3 RNAi agent comprises the sense strand and antisense strand nucleotide sequences of any of the duplexes represented by any of the Duplex ID Nos. presented herein. In some embodiments, a C3 RNAi agent comprises the sense strand and antisense strand nucleotide sequences of any of the duplexes represented by any of the Duplex ID Nos. presented herein and a targeting group and/or linking group wherein the targeting group and/or linking group is covalently linked (i.e., conjugated) to the sense strand or the antisense strand. In some embodiments, a C3 RNAi agent includes the sense strand and antisense strand modified nucleotide sequences of any of the Duplex ID Nos. presented herein. In some embodiments, a C3 RNAi agent comprises the sense strand and antisense strand modified nucleotide sequences of any of the Duplex ID Nos. presented herein and a targeting group and/or linking group, wherein the targeting group and/or linking group is covalently linked to the sense strand or the antisense strand.

In some embodiments, a C3 RNAi agent comprises an antisense strand and a sense strand having the nucleotide sequences of any of the antisense strand/sense strand duplexes of Table 2 or Tables 5A, 5B, and 5C, and further comprises a targeting group or targeting ligand. In some embodiments, a C3 RNAi agent comprises an antisense strand and a sense strand having the nucleotide sequences of any of the antisense strand and/or sense strand nucleotide sequences in Table 3 or Table 4.

In some embodiments, a C3 RNAi agent comprises an antisense strand and a sense strand having a modified nucleotide sequence of any of the antisense strand and/or sense strand nucleotide sequences of any of the duplexes Tables 5A, 5B, and 5C, and further comprises an asialoglycoprotein receptor ligand targeting group.

In some embodiments, a C3 RNAi agent comprises, consists of, or consists essentially of any of the duplexes of Tables 5A, 5B, and 5C.

TABLE 5A

C3 RNAi Agents Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD09546 | AM13561-AS | 13 | 3 | AM12489-SS | 14 | 8 |

TABLE 5B

C3 RNAi Agents Duplexes with Corresponding Sense and Antisense Strand ID Numbers Referencing Position Targeted on C3 Gene (SEQ ID NO: 1)

| Duplex ID | Antisense Strand ID | Sense Strand ID | Targeted C3 Gene Position (Of SEQ ID NO: 1) |
|---|---|---|---|
| AD09546 | AM13561-AS | AM12489-SS | 2566 |

TABLE 5C

C3 RNAi Agent Duplexes Showing Chemically Modified Antisense Strand and Sense Strand Sequences

| Duplex ID: | Modified Antisense Strand (5' → 3') | SEQ ID NO. | Modified Sense Strand (5' → 3') | SEQ ID NO. |
|---|---|---|---|---|
| AD09546 | usUfsusCfgAfacaacAfgAfgUfaGfGfgsu | 13 | (NAG37)s(invAb)sacccuacuCfUfGfuuguucgaaas(invAb) | 14 | strand and a sense strand having the nucleotide sequences of any of the antisense strand/sense strand duplexes of Table 2 or Tables 5A, 5B, and 5C, and further comprises an asialoglycoprotein receptor ligand targeting group.

A targeting group, with or without a linker, can be linked to the 5' or 3' end of any of the sense and/or antisense strands disclosed in Tables 2, 3, 4, or 5C. A linker, with or without a targeting group, can be attached to the 5' or 3' end of any of the sense and/or antisense strands disclosed in Tables 2, 3, 4, and 5C.

In some embodiments, a C3 RNAi agent comprises an antisense strand and a sense strand having the nucleotide sequences of any of the antisense strand/sense strand duplexes of Table 2 or Tables 5A, 5B and 5C, and further comprises a targeting ligand selected from the group consisting of: (NAG37) and (NAG37)s, each as defined in Table 6.

In some embodiments, a C3 RNAi agent comprises an antisense strand and a sense strand having the modified In some embodiments, a C3 RNAi agent is prepared or provided as a salt, mixed salt, or a free-acid. The RNAi agents described herein, upon delivery to a cell expressing a C3 gene, inhibit or knockdown expression of one or more C3 genes in vivo and/or in vitro.

Targeting Ligands or Groups, Linking Groups, and Delivery Vehicles

In some embodiments, a C3 RNAi agent is conjugated to one or more non-nucleotide groups including, but not limited to, a targeting group, a linking group, a targeting ligand, a delivery polymer, or a delivery vehicle. The non-nucleotide group can enhance targeting, delivery or attachment of the RNAi agent. Examples of targeting groups and linking groups are provided in Table 6. The non-nucleotide group can be covalently linked to the 3' and/or 5' end of either the sense strand and/or the antisense strand. In some embodiments, a C3 RNAi agent contains a non-nucleotide group linked to the 3' and/or 5' end of the sense strand. In some embodiments, a non-nucleotide group is linked to the 5' end of a C3 RNAi agent sense strand. A non-nucleotide group may be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules.

In some embodiments, a targeting group is linked to an RNAi agent using a linker, such as a PEG linker or one, two, or three abasic and/or ribitol (abasic ribose) residues, which can in some instances serve as linkers. In some embodiments, a targeting ligand comprises a galactose-derivative cluster.

The C3 RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

In some embodiments, a targeting group comprises an asialoglycoprotein receptor ligand. As used herein, an asialoglycoprotein receptor ligand is a ligand that contains a moiety having affinity for the asialoglycoprotein receptor. As noted herein, the asialoglycoprotein receptor is highly expressed on hepatocytes. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formylgalactosamine, N-acetyl-galactosamine, N-propionyl-galactosamine, N-n-butanoyl-galactosamine, and N-iso-butanoylgalactos-amine (see for example: S. T. Iobst and K. Drickamer, J. B. C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative, also referred to as monovalent or monodentate) or multimeric (e.g., having multiple galactose derivatives). The galactose derivative or galactose derivative cluster can be attached to the 3' or 5' end of the sense or antisense strand of the RNAi agent using methods known in the art.

The preparation of targeting ligands, such as galactose derivative clusters, is described in, for example, International Patent Application Publication No. WO 2018/044350 to Arrowhead Pharmaceuticals, Inc., and International Patent Application Publication No. WO 2017/156012 to Arrowhead Pharmaceuticals, Inc., the contents of both of which are incorporated by reference herein in their entirety.

As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or tri-valent galactose derivative). In some embodiments, the galactose derivative cluster comprises N-acetyl-galactosamine moieties. In some embodiments, the galactose derivative cluster comprises three N-acetyl-galactosamine moieties. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosamine moieties.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see, e.g., U.S. Pat. No. 5,885,968; Biessen et al. J. Med. Chem. 1995 Vol. 39 p. 1538-1546). In some embodiments, the PEG spacer is a $PEG_3$ spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

Embodiments of the present disclosure include pharmaceutical compositions for delivering a C3 RNAi agent to a liver cell in vivo. Such pharmaceutical compositions can include, for example, a C3 RNAi agent conjugated to a galactose derivative cluster. In some embodiments, the galactose derivative cluster is comprised of a galactose derivative trimer, which can be, for example, an N-acetyl-galactosamine trimer, or galactose derivative tetramer, which can be, for example, an N-acetyl-galactosamine tetramer.

A targeting ligand or targeting group can be linked to the 3' or 5' end of a sense strand or an antisense strand of a C3 RNAi agent disclosed herein.

Targeting ligands include, but are not limited to (NAG37) and (NAG37)s as defined in Table 6. Other targeting groups and targeting ligands, including galactose cluster targeting ligands, are known in the art.

In some embodiments, a linking group is conjugated to the RNAi agent. The linking group facilitates covalent linkage of the agent to a targeting group, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, can include, but are not limited to: reactive groups such a primary amines and alkynes, alkyl groups, abasic nucleotides, ribitol (abasic ribose), and/or PEG groups.

In some embodiments, a targeting group is linked internally to a nucleotide on the sense strand and/or the antisense strand of the RNAi agent. In some embodiments, a targeting group is linked to the RNAi agent via a linker.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage can optionally include a spacer that increases the distance between the two joined atoms. A spacer can further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, when two or more RNAi agents are included in a single composition, each of the RNAi agents may be linked to the same targeting group or two a different targeting groups (i.e., targeting groups having different chemical structure). In some embodiments, targeting groups are linked to the C3 RNAi agents disclosed herein without the use of an additional linker. In some embodiments, the targeting group itself is designed having a linker or other site to facilitate conjugation readily present. In some embodiments, when two or more C3 RNAi agents are included in a single molecule, each of the RNAi agents may utilize the same linker or different linkers (i.e., linkers having different chemical structures).

Any of the C3 RNAi agent nucleotide sequences listed in Tables 2, 3, 4, 5C, 7A, 7B, or 8 whether modified or unmodified, can contain 3' and/or 5' targeting group(s) or linking group(s). Any of the C3 RNAi agent sequences listed in Table 3 or 4, or are otherwise described herein, which contain a 3' or 5' targeting group or linking group, can alternatively contain no 3' or 5' targeting group or linking group, or can contain a different 3' or 5' targeting group or linking group including, but not limited to, those depicted in Table 6. Any of the C3 RNAi agent duplexes listed in Tables 5A, 5B, 5C, and 8, whether modified or unmodified, can further comprise a targeting group or linking group, including, but not limited to, those depicted in Table 6, and the targeting group or linking group can be attached to the 3' or 5' terminus of either the sense strand or the antisense strand of the C3 RNAi agent duplex.

Examples of targeting groups and linking groups (which when combined can form targeting ligands) are provided in Table 6. Table 4, Table 5C, and Table 8 provide certain embodiments of C3 RNAi agent sense strands having a targeting group or linking group linked to the 5' or 3' end.

TABLE 6

Structures Representing Various Modified Nucleotides, Targeting Ligands or Targeting Groups, Capping Residues, and Linking Groups

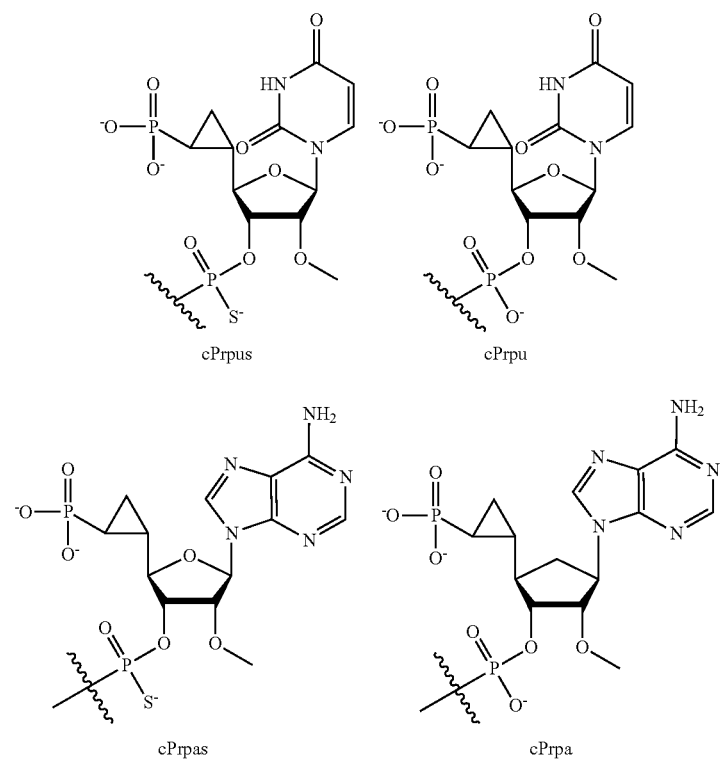

cPrpus     cPrpu cPrpas     cPrpa

TABLE 6-continued

Structures Representing Various Modified Nucleotides, Targeting Ligands or Targeting Groups, Capping Residues, and Linking Groups When positioned internally:
linkage towards 5' end

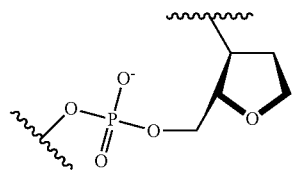

linkage towards 3' end (invAb)

When positioned internally:
linkage towards 5' end

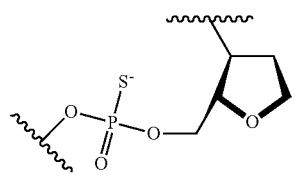

linkage towards 3' end (invAb)s

When positioned at the 3' terminal end:
linkage towards 5' end

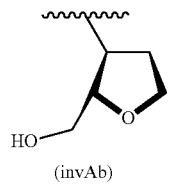

(invAb)

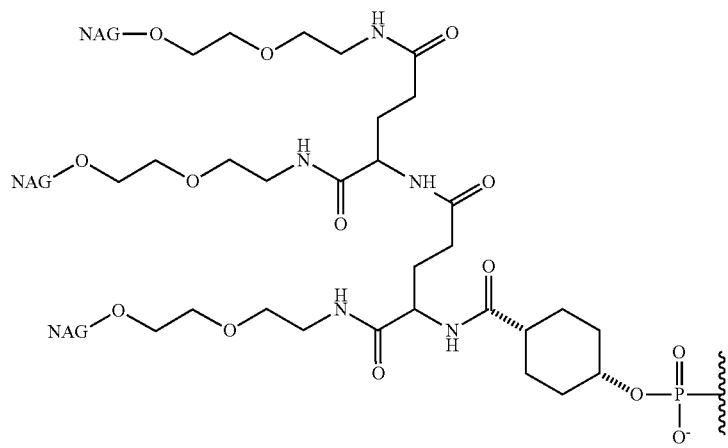

(NAG37)

TABLE 6-continued

Structures Representing Various Modified Nucleotides, Targeting Ligands or Targeting Groups, Capping Residues, and Linking Groups

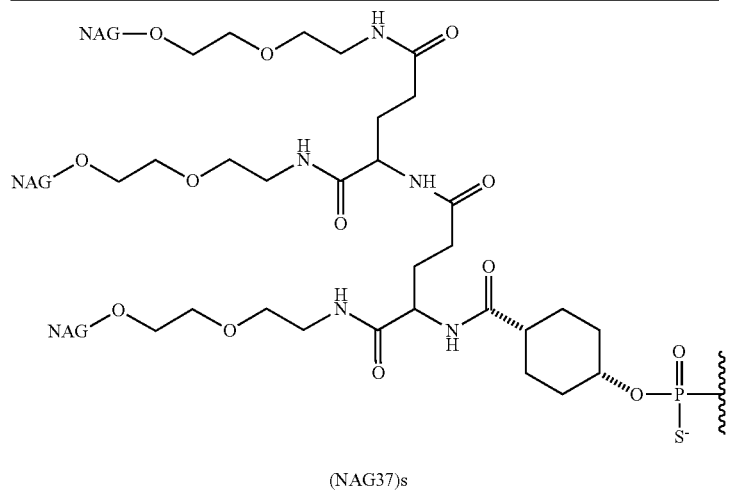

(NAG37)s

In each of the above structures in Table 6, NAG comprises an N-acetyl-galactosamine. In some embodiments, NAG as depicted in Table 6 above can comprise another galactose derivative that has affinity for the asialoglycoprotein receptor present on hepatocytes, as would be understood by a person of ordinary skill in the art to be attached in view of the structures above and description provided herein. Other linking groups known in the art may be used.

In some embodiments, a delivery vehicle can be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine. In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), hydrogels, cyclodextrins, biodegradable nanocapsules, and bioadhesive microspheres, proteinaceous vectors, or other delivery systems suitable for nucleic acid or oligonucleotide delivery as known and available in the art.

Pharmaceutical Compositions

The C3 RNAi agents disclosed herein can be prepared as pharmaceutical compositions or formulations (also referred to herein as "medicaments"). In some embodiments, pharmaceutical compositions include at least one C3 RNAi agent. These pharmaceutical compositions are particularly useful in the inhibition of the expression of the target mRNA in a target cell, a group of cells, a tissue, or an organism.

The pharmaceutical compositions can be used to treat a subject having a disease, disorder, or condition that would benefit from reduction in the level of the target C3 mRNA, or inhibition in expression of the target gene. The pharmaceutical compositions can be used to treat a subject at risk of developing a disease, disorder, symptom, or condition that would benefit from reduction of the level of the target mRNA or an inhibition in expression the target gene. In one embodiment, the method includes administering a C3 RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include a C3 RNAi agent, thereby forming a pharmaceutical formulation or medicament suitable for in vivo delivery to a subject, including a human.

The pharmaceutical compositions that include a C3 RNAi agent and methods disclosed herein decrease the level of the target mRNA in a cell, group of cells, group of cells, tissue, organ, or subject, including by administering to the subject a therapeutically effective amount of a herein described C3 RNAi agent, thereby inhibiting the expression or translation of C3 mRNA in the subject. In some embodiments, the subject has been previously identified as having a pathogenic upregulation of the target gene in hepatocytes. In some embodiments, the subject has been previously identified or diagnosed as having IgA nephropathy, C3 glomerulopathy, and/or paroxysmal nocturnal hemoglobinuria. In some embodiments, the subject has been suffering from symptoms associated with IgA nephropathy, C3 glomerulopathy, and/or paroxysmal nocturnal hemoglobinuria. In some embodiments, the subject would benefit from a reduction of C3 gene expression in the subject's liver.

In some embodiments, the described pharmaceutical compositions including a C3 RNAi agent are used for treating or managing clinical presentations associated with IgA nephropathy, C3 glomerulopathy, and/or paroxysmal nocturnal hemoglobinuria (PNH). Other diseases or conditions for which a C3 RNAi agent may be useful include lupus nephritis, primary membranous nephropathy (PMN), and/or autoimmune hemolytic anemia (AIHA)/cold agglutinin disease (CAD). In some embodiments, a therapeutically (including prophylactically) effective amount of one or more of pharmaceutical compositions is administered to a subject in need of such treatment. In some embodiments, administration of any of the disclosed C3 RNAi agents can be used to decrease the number, severity, and/or frequency of symptoms of a disease in a subject.

The described pharmaceutical compositions that include a C3 RNAi agent can be used to treat at least one symptom in a subject having a disease or disorder that would benefit from reduction or inhibition in expression of C3 mRNA and/or a reduction in C3 protein levels. Measuring C3 levels can be conducted in accordance with established methods known in the art.

In some embodiments, the subject is administered a therapeutically effective amount of one or more pharmaceutical compositions that include a C3 RNAi agent thereby treating the symptom. In other embodiments, the subject is administered a prophylactically effective amount of one or more C3 RNAi agents, thereby preventing or inhibiting the at least one symptom.

The route of administration is the path by which a C3 RNAi agent is brought into contact with the body. In general, methods of administering drugs and oligonucleotides and nucleic acids for treatment of a mammal are well known in the art and can be applied to administration of the compositions described herein. The C3 RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, the herein described pharmaceutical compositions are administered via subcutaneous injection.

The pharmaceutical compositions including a C3 RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

In some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., C3 RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® ELTM (BASF, Parsippany, NJ) or phosphate buffered saline (PBS). Suitable carriers should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

In some embodiments, pharmaceutical formulations that include the C3 RNAi agents disclosed herein suitable for subcutaneous administration can be prepared in an aqueous sodium phosphate buffer (e.g., the C3 RNAi agent formulated in 0.5 mM sodium phosphate monobasic, 0.5 mM sodium phosphate dibasic, in water). In some embodiments, pharmaceutical formulations that include the C3 RNAi agents disclosed herein suitable for subcutaneous administration can be prepared in water for injection (sterile water). C3 RNAi agents disclosed herein suitable for subcutaneous administration can be prepared in isotonic saline (0.9%).

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for oral administration of the C3 RNAi agents disclosed herein can also be prepared. In some embodiments, the C3 RNAi agents disclosed herein are administered orally. In some embodiments, the C3 RNAi agents disclosed herein are formulated in a capsule for oral administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The C3 RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, analgesics, antihistamines, or anti-inflammatory agents (e.g., acetaminophen, NSAIDs, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another C3 RNAi agent (e.g., a C3 RNAi agent that targets a different sequence within the C3 target). In other embodiments, the second therapeutic can be a small molecule drug, an antibody, an antibody fragment, or an aptamer.

In some embodiments, the described C3 RNAi agent(s) are optionally combined with one or more additional therapeutics. The C3 RNAi agent and additional therapeutic(s) can be administered in a single composition or they can be administered separately. In some embodiments, the one or more additional therapeutics is administered separately in separate dosage forms from the RNAi agent (e.g., the C3 RNAi agent is administered by subcutaneous injection, while the additional therapeutic involved in the method of treatment dosing regimen is administered orally). In some embodiments, the described C3 RNAi agent(s) are administered to a subject in need thereof via subcutaneous injection, and the one or more optional additional therapeutics are administered orally, which together provide for a treatment regimen for diseases and conditions associated with IgA nephropathy, C3 glomerulopathy, and/or paroxysmal nocturnal hemoglobinuria. In some embodiments, the described C3 RNAi agent(s) are administered to a subject in need thereof via subcutaneous injection, and the one or more optional additional therapeutics are administered via a separate subcutaneous injection. In some embodiments, the C3 RNAi agent and one or more additional therapeutics are combined into a single dosage form (e.g., a "cocktail" formulated into a single composition for subcutaneous injection). The C3 RNAi agents, with or without the one or more additional therapeutics, can be combined with one or more excipients to form pharmaceutical compositions.

Generally, an effective amount of a C3 RNAi agent will be in the range of from about 0.1 to about 100 mg/kg of body weight/dose, e.g., from about 1.0 to about 50 mg/kg of body weight/dose. In some embodiments, an effective amount of an active compound will be in the range of from about 0.25 to about 5 mg/kg of body weight per dose. In some embodiments, an effective amount of an active ingredient will be in the range of from about 0.5 to about 4 mg/kg of body weight per dose. In some embodiments, an effective amount of a C3 RNAi agent may be a fixed dose. In some embodiments, the fixed dose is in the range of from about 5 mg to about 1,000 mg of C3 RNAi agent. In some embodiments, the fixed does is in the range of 50 to 400 mg of C3 RNAi agent. Dosing may be weekly, bi-weekly, monthly, quarterly, or at any other interval depending on the dose of C3 RNAi agent administered, the activity level of the particular C3 RNAi agent, and the desired level of inhibition for the particular subject. The Examples herein show suitable levels for inhibition in certain animal species. The amount administered will depend on such variables as the overall health status of the patient or subject, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum.

For treatment of disease or for formation of a medicament or composition for treatment of a disease, the pharmaceutical compositions described herein including a C3 RNAi agent can be combined with an excipient or with a second therapeutic agent or treatment including, but not limited to: a second or other RNAi agent, a small molecule drug, an antibody, an antibody fragment, peptide and/or an aptamer.

The described C3 RNAi agents, when added to pharmaceutically acceptable excipients or adjuvants, can be packaged into kits, containers, packs, or dispensers. The pharmaceutical compositions described herein may be packaged in pre-filled syringes, pen injectors, autoinjectors, infusion bags/devices, or vials.

C3 RNAi Agent Drug Substances and Formulations

In some embodiments, the C3 RNAi agent disclosed herein has the nucleotide sequences of the C3 RNAi Drug Substance shown in Table 8, below. The nucleotide sequences of the C3 RNAi agent found in C3 RNAi Drug Substance include an antisense strand nucleotide sequence as set forth in the following Table 7A, and a sense strand nucleotide sequence as set forth in the following Table 7B.

TABLE 7A

C3 RNAi Agent Antisense Strand Sequence

| SEQ ID NO. | Antisense Sequence (Modified) (5' → 3') | SEQ ID NO. | Underlying Base Sequence (5' → 3') |
|---|---|---|---|
| 13 | usUfsusCfgAfacaacAfgAfgUfaGfGfgsu | 3 | UUUCGAACAACAGAGUAGGGU |

TABLE 7B

C3 RNAi Agent Sense Strand Nucleotide Sequence (shown as modified version without inverted abasic residues or NAG targeting group present in C3 RNAi Drug Substance)

| SEQ ID NO. | Sense Sequence (Modified) (5' → 3') | SEQ ID NO. | Underlying Base Sequence (5' → 3') |
|---|---|---|---|
| 15 | acccuacuCfUfGfuuguucgaaa | 8 | ACCCUACUCUGUUGUUCGAAA |

As used in Tables 7A, 7B, and 8 herein, the following notations are used to indicate modified nucleotides, targeting groups, and linking groups: A, C, G, and U represent adenosine, cytidine, guanosine, and uridine, respectively; a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; s represents a phosphorothioate linkage; (invAb) represents an inverted abasic deoxyribose residue (see Table 6); and (NAG37)s represents the following structure (depicted as both a sodium salt and free acid):

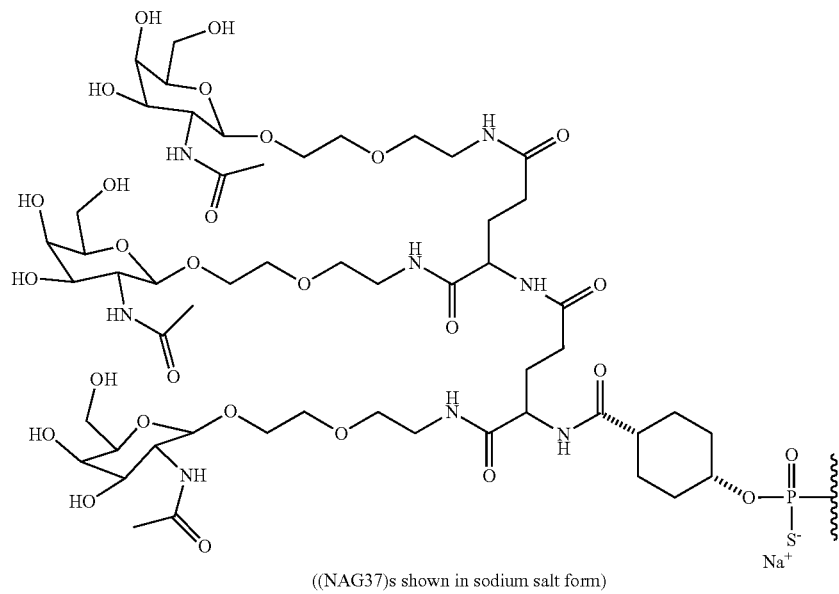

((NAG37)s shown in sodium salt form)

-continued

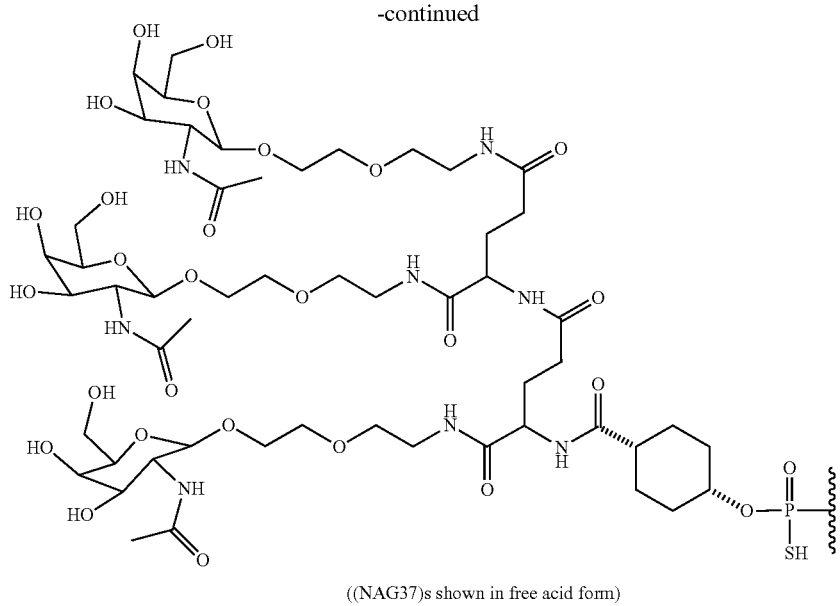

((NAG37)s shown in free acid form)

25

Each sense strand and/or antisense strand can have any targeting groups or linking groups listed above, as well as other targeting or linking groups, conjugated to the 5' and/or 3' end of the sequence.

The C3 RNAi agent antisense strand sequence is designed to target mRNA transcripts from a C3 gene in a human subject, thereby silencing translation of C3 protein using an RNA interference mechanism for human subjects with C3.

In some embodiments, the methods disclosed herein use the C3 RNAi Drug Substance set forth in the following Table 8:

TABLE 8

C3 RNAi Drug Substance
Sense and Antisense Strands (The sense and antisense strands are annealed to form a duplex):

| Sense Strand (Modified Sequence) (5' → 3'): | (NAG37)s(invAb)sacccuacu (SEQ ID NO: 14) CfUfGfuuguucgaaas(invAb) |
|---|---|
| Antisense Strand (Modified Sequence) (5' → 3'): | usUfsusCfgAfacaacAfgAfgU (SEQ ID NO: 13) faGfGfgsu |

TABLE 8.1

Properties of C3 RNAi Drug Substance Described in Table 8

| Chemical Formula: | $C_{493}H_{611}F_{11}Na_{43}N_{164}O_{311}P_{43}S_7$ (Na$^+$ form) $C_{493}H_{654}F_{11}N_{164}O_{311}P_{43}S_7$ (H$^+$ form) |
|---|---|
| Molecular Weight: | 16563.98 (Na$^+$ form) 15618.77 (H$^+$ form) |
| Physical Appearance: | White to Off-white Powder |
| Solubility | Soluble in water and the formulation buffer (0.5 mM sodium phosphate monobasic, 0.5 mM sodium phosphate dibasic) |

In some embodiments, the C3 RNAi Drug Substance is prepared or provided as a salt, mixed salt, or a free acid. In some embodiments, the form is a sodium salt.

In some embodiments, the C3 RNAi Drug Substance as provided in Table 8 is formulated with one or more pharmaceutically acceptable excipients to form a pharmaceutical composition suitable for administration to a human subject. In some embodiments, the C3 RNAi Drug Substance described in Table 8 is formulated at 200 mg/mL (free acid/salt free basis) in an aqueous sodium phosphate buffer (0.5 mM sodium phosphate monobasic, 0.5 mM sodium phosphate dibasic), which is suitable for subcutaneous administration in humans.

Methods of Treatment and Inhibition of Expression

The C3 RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from reduction and/or inhibition in expression of C3 mRNA and/or C3 protein levels, for example, a subject that has been diagnosed with or is suffering from symptoms related to IgA nephropathy, C3 glomerulopathy, and/or paroxysmal nocturnal hemoglobinuria.

In some embodiments, the subject is administered a therapeutically effective amount of any one or more C3 RNAi agents. Treatment of a subject can include therapeutic and/or prophylactic treatment. The subject is administered a therapeutically effective amount of any one or more C3 RNAi agents described herein. The subject may be an adult, adolescent, child, or infant. Administration of a pharmaceutical composition described herein can be to a human being or animal.

The C3 RNAi agents described herein can be used to treat at least one symptom or manifestation of disease in a subject having a C3-related disease or disorder, such as a disease or disorder that is mediated at least in part by dysregulated complement activity, dysregulated C3 activity, or C3 gene expression. In some embodiments, the C3 RNAi agents are used to treat or manage a clinical presentation of a subject with a disease or disorder that would benefit at least in part by a reduction in C3 mRNA or C3 protein levels. The subject is administered a therapeutically effective amount of one or more of the C3 RNAi agents or C3 RNAi agent-containing compositions described herein. In some embodiments, the methods disclosed herein comprise administering a composition comprising a C3 RNAi agent described herein to a subject to be treated. In some embodiments, the subject is administered a prophylactically effective amount of any one or more of the described C3 RNAi agents, thereby treating a subject by preventing or inhibiting at least one symptom or manifestation of disease.

In certain embodiments, the present disclosure provides methods for treatment of diseases, disorders, conditions, or pathological states mediated at least in part by C3 gene expression, dysregulation of the complement cascade, or dysregulated complement activity, in a patient in need thereof, wherein the methods include administering to the patient any of the C3 RNAi agents described herein.

In some embodiments, the gene expression level and/or mRNA level of a C3 gene in a subject to whom a described C3 RNAi agent is administered is reduced by at least about 30%, 35%, 40%, 45%, 50%, 55%, 60%, 65%, 70%, 75%, 80%, 85%, 95%, 96%, 97%, 98%, 99%, or greater than 99% relative to the subject prior to being administered the C3 RNAi agent or to a subject not receiving the C3 RNAi agent. The C3 mRNA level in the subject may be reduced in a cell, group of cells, and/or tissue of the subject. In some embodiments, the C3 gene expression is inhibited by at least about 30%, 35%, 40%, 45% 50%, 55%, 60%, 65%, or greater than 65% in hepatocytes relative to the subject prior to being administered the C3 RNAi agent or to a subject not receiving the C3 RNAi agent.

In some embodiments, the C3 protein level in a subject to whom a described C3 RNAi agent has been administered is reduced by at least about 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the C3 RNAi agent or to a subject not receiving the C3 RNAi agent. The protein level in the subject may be reduced in a cell, group of cells, tissue, blood, and/or other fluid of the subject.

A reduction in C3 mRNA levels and C3 protein levels can be assessed by any methods known in the art. As used herein, a reduction or decrease in C3 mRNA level and/or protein level are collectively referred to herein as a reduction or decrease in C3 or inhibiting or reducing the gene expression of C3. The Examples set forth herein illustrate known methods for assessing inhibition of C3 gene expression. The person of ordinary skill in the art would further know suitable methods for assessing inhibition of C3 gene expression in vivo and/or in vitro.

In some embodiments, disclosed herein are methods of treatment (including prophylactic or preventative treatment) of diseases, disorders, or symptoms caused by IgA nephropathy, C3 glomerulopathy, and/or paroxysmal nocturnal hemoglobinuria, wherein the methods include administering to a subject in need thereof a therapeutically effective amount of a C3 RNAi agent that includes an antisense strand that is at least partially complementary to the portion of the C3 mRNA having the sequence in Table 1. In some embodiments, disclosed herein are methods of treatment (including prophylactic or preventative treatment) of diseases, disorders, or symptoms caused by a complement-mediated renal disease (CMRD), wherein the methods include administering to a subject in need thereof a therapeutically effective amount of a C3 RNAi agent that includes an antisense strand that is at least partially complementary to the portion of the C3 mRNA having the sequence in Table 1. In some embodiments, disclosed herein are methods of treatment (including prophylactic or preventative treatment) of diseases or symptoms caused by IgA nephropathy, C3 glomerulopathy, and/or paroxysmal nocturnal hemoglobinuria, wherein the methods include administering to a subject in need thereof a therapeutically effective amount of a C3 RNAi agent that includes an antisense strand comprising the sequence of any of the sequences in Tables 2, 3, 5C, 7A, or 8, and a sense strand that comprises any of the sequences in Tables 2, 4, 5C, 7B, or 8 that is at least partially complementary to the antisense strand. In some embodiments, disclosed herein are methods of treatment (including prophylactic or preventative treatment) of diseases or symptoms caused by IgA nephropathy, C3 glomerulopathy, and/or paroxysmal nocturnal hemoglobinuria, wherein the methods include administering to a subject in need thereof a therapeutically effective amount of a C3 RNAi agent that includes a sense strand that comprises any of the sequences in Tables 2, 4, 5C, 7B, or 8 and an antisense strand comprising the sequence of any of the sequences in Tables 2, 3, 5C, 7A, or 8 that is at least partially complementary to the sense strand.

In some embodiments, disclosed herein are methods for inhibiting expression of a C3 gene in a cell, wherein the methods include administering to the cell a C3 RNAi agent that includes an antisense strand that is at least partially complementary to the portion of the C3 mRNA having the sequence in Table 1. In some embodiments, disclosed herein are methods of inhibiting expression of a C3 gene in a cell, wherein the methods include administering to a cell a C3 RNAi agent that includes an antisense strand comprising the sequence of any of the sequences in Tables 2, 3, 5C, 7A, or 8 and a sense strand that comprises any of the sequences in Tables 2, 4, 5C, 7B, or 8 that is at least partially complementary to the antisense strand. In some embodiments, disclosed herein are methods of inhibiting expression of a C3 gene in a cell, wherein the methods include administering a C3 RNAi agent that includes a sense strand that comprises any of the sequences in Tables 2, 4, 5C, 7B, or 8, and an antisense strand that includes the sequence of any of the sequences in Tables 2, 3, 5C, 7A, or 8 that is at least partially complementary to the sense strand.

The use of C3 RNAi agents provides methods for therapeutic (including prophylactic) treatment of diseases/disorders associated with complement dysregulation, including but not limited to IgA nephropathy, C3 glomerulopathy, paroxysmal nocturnal hemoglobinuria, and/or elevated C3 gene expression. The described C3 RNAi agents mediate RNA interference to inhibit the expression of one or more genes necessary for production of C3 protein. C3 RNAi agents can also be used to treat or prevent various diseases, disorders, or conditions, including IgA nephropathy, C3 glomerulopathy, and/or paroxysmal nocturnal hemoglobinuria. Furthermore, compositions for delivery of C3 RNAi agents to liver cells, and specifically to hepatocytes, in vivo, are described.

Cells, Tissues, Organs, and Non-Human Organisms

Cells, tissues, organs, and non-human organisms that include at least one of the C3 RNAi agents described herein are contemplated. The cell, tissue, organ, or non-human organism is made by delivering the RNAi agent to the cell, tissue, organ or non-human organism.

Embodiments

The following non-limiting embodiments illustrate the invention described herein.

Embodiment 1. An RNAi agent for inhibiting expression of a C3 gene, comprising:
an antisense strand wherein nucleotides 1-21 of the antisense strand comprise nucleotides 1-21 of the antisense strand sequences of Table 2, Table 3, Table 5C, Table 7A, or Table 8; and
a sense strand comprising a nucleotide sequence that is at least partially complementary to the antisense strand, wherein all or substantially all of the nucleotides of the antisense strand and/or the sense strand are modified nucleotides, and the RNAi agent is linked to a targeting ligand that comprises N-acetyl-galactosamine.

Embodiment 2. The RNAi agent for inhibiting expression of a C3 gene, wherein the sense strand comprises a nucleotide sequence of at least 15 contiguous nucleotides differing by 0 or 1 nucleotides from 15 contiguous nucleotides of any one of the sense strand sequences of Table 2, Table 4, Table 5C, Table 7B, or Table 8, and wherein the sense strand has a region of at least 85% complementarity over at least 15 contiguous nucleotides to the antisense strand.

Embodiment 3. The RNAi agent of any one of embodiments 1-2, wherein at least one nucleotide of the RNAi agent includes a modified internucleoside linkage.

Embodiment 4. The RNAi agent of any one of embodiments 1-3, wherein the modified nucleotides are independently selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate-containing nucleotide, cyclopropyl phosphonate-containing nucleotide, and 3'-O-methyl nucleotide.

Embodiment 5. The RNAi agent of embodiment 4, wherein all or substantially all of the modified nucleotides are 2'-O-methyl nucleotides, 2'-fluoro nucleotides, or combinations thereof.

Embodiment 6. The RNAi agent of any one of embodiments 1-5, wherein the antisense strand consists of or consists essentially of the nucleotide sequence of any one of the modified antisense strand sequences of Table 3, Table 5C, Table 7A, or Table 8.

Embodiment 7. The RNAi agent of any one of embodiments 1-6, wherein the sense strand consists of, consists essentially of, or comprises the nucleotide sequence of any of the modified sense strand sequences of Table 4, Table 5C, Table 7B, or Table 8.

Embodiment 8. The RNAi agent of embodiment 1, wherein the antisense strand comprises the nucleotide sequence of any one of the modified sequences of Table 3, Table 5C, Table 7A, or Table 8, and the sense strand comprises the nucleotide sequence of any one of the modified sequences of Table 4, Table 5C, Table 7B, or Table 8.

Embodiment 9. The RNAi agent of any one of embodiments 1-8, wherein the targeting ligand comprises:

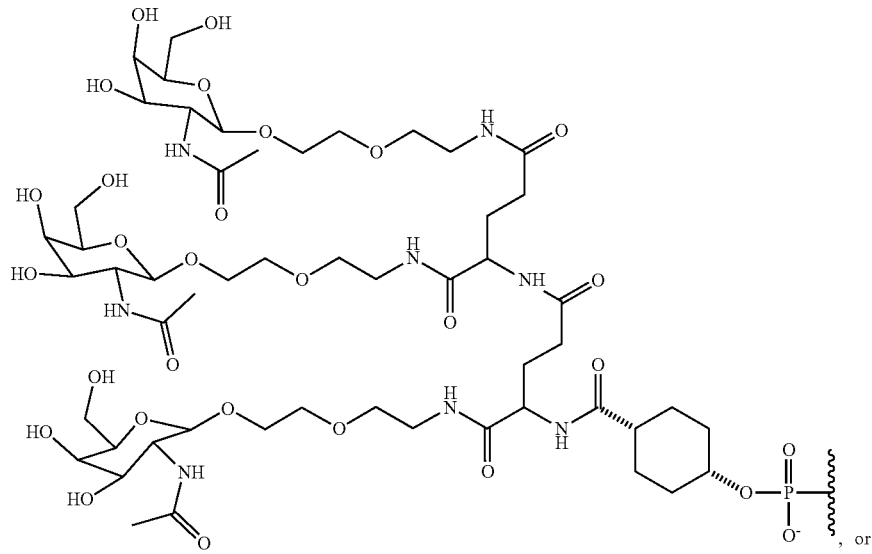
, or

-continued

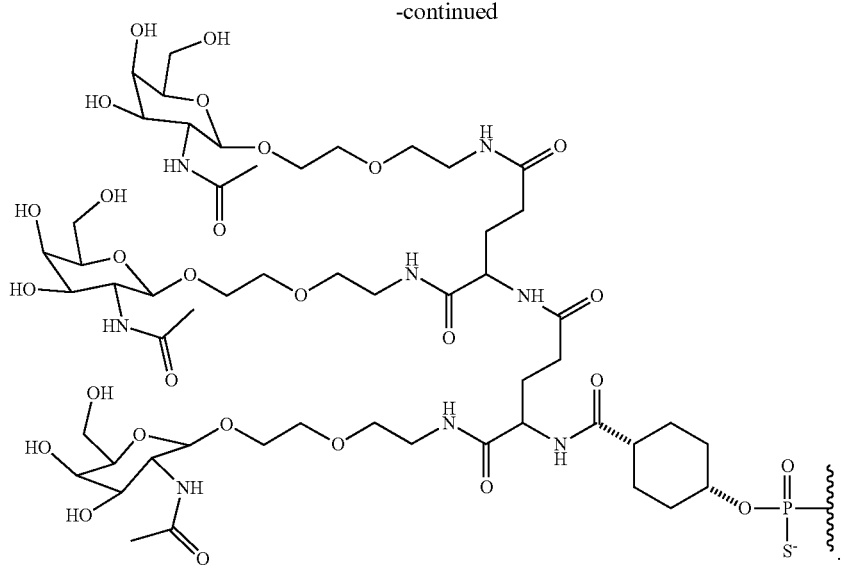

Embodiment 10. The RNAi agent of any one of embodiments 1-9, wherein the targeting ligand is linked to the sense strand.

Embodiment 11. The RNAi agent of embodiment 10, wherein the targeting ligand is linked to the 5' terminal end of the sense strand.

Embodiment 12. The RNAi agent of any one of embodiments 1-11, wherein the sense strand is between 15 and 30 nucleotides in length, and the antisense strand is between 21 and 30 nucleotides in length.

Embodiment 13. The RNAi agent of embodiment 12, wherein the sense strand and the antisense strand are each between 21 and 27 nucleotides in length.

Embodiment 14. The RNAi agent of embodiment 13, wherein the sense strand and the antisense strand are each between 21 and 24 nucleotides in length.

Embodiment 15. The RNAi agent of embodiment 14, wherein the sense strand and the antisense strand are each 21 nucleotides in length.

Embodiment 16. The RNAi agent of any one of embodiments 1-15, wherein the RNAi agent has two blunt ends.

Embodiment 17. The RNAi agent of any one of embodiments 1-16, wherein the sense strand comprises one or two terminal caps.

Embodiment 18. The RNAi agent of any one of embodiments 1-17, wherein the sense strand comprises one or two inverted abasic residues.

Embodiment 19. The RNAi agent of embodiment 1, wherein the RNAi agent is comprised of a sense strand and an antisense strand that form a duplex sequence of any of the duplexes set forth in Table 5A, 5B, 5C, or 8.

Embodiment 20. The RNAi agent of any of embodiments 1-19, wherein the RNAi agent is a pharmaceutically acceptable salt.

Embodiment 21. The RNAi agent of embodiment 20, wherein the RNAi agent is a sodium salt.

Embodiment 22. A composition comprising the RNAi agent of any one of embodiments 1-21, wherein the composition comprises a pharmaceutically acceptable excipient.

Embodiment 23. The composition of embodiment 22, wherein the pharmaceutically acceptable excipient is a sodium phosphate buffer.

Embodiment 24. The composition of embodiment 22, wherein the pharmaceutically acceptable excipient is isotonic saline or water for injection.

Embodiment 25. A method for inhibiting expression of a C3 gene in a hepatocyte cell, the method comprising introducing into the cell an effective amount of an RNAi agent of any one of embodiments 1-21 or the composition of any one of embodiments 22-24.

Embodiment 26. The method of embodiment 25, wherein C3 mRNA is reduced by at least about 50% in the hepatocyte cell.

Embodiment 27. The method of any one of embodiments 25-26, wherein C3 protein is reduced by at least about 50% in the hepatocyte cell.

Embodiment 28. A method for inhibiting expression of a C3 gene in a subject, the method comprising administering to the subject an effective amount of an RNAi agent of any one of embodiments 1-21 or the composition of any one of embodiments 22-24.

Embodiment 29. The method of embodiment 28, wherein the subject is a human subject.

Embodiment 30. The method of embodiment 28 or 29, wherein C3 mRNA is reduced by at least about 50% in the subject.

Embodiment 31. The method of any one of embodiments 28-30, wherein C3 protein is reduced by at least about 50% in the subject.

Embodiment 32. A method of treating a C3-related disease, disorder, symptom, or other manifestation of disease, the method comprising administering to a human subject in need thereof a therapeutically effective amount of the composition of any one of embodiments 22-24.

Embodiment 33. The method of embodiment 32, wherein the disease is IgA nephropathy (IgAN), C3 glomerulopathy (C3G), paroxysmal nocturnal hemoglobinuria (PNH), lupus nephritis, primary membranous nephropathy (PMN), autoimmune hemolytic anemia/cold agglutinin disease (AIHA/CAD), and/or another type of complement-mediated renal disease.

Embodiment 34. The method of any one of embodiments 25-33, wherein the level of serum C3 protein is decreased in the subject.

Embodiment 35. The method of any one of embodiments 25-34, wherein the alternative complement pathway hemolytic activity (AH50) is reduced in the subject by at least about 50%.

Embodiment 36. The method of embodiment 35, wherein the AH50 is reduced by at least approximately 75%.

Embodiment 37. The method of embodiment 36, wherein the AH50 is reduced by approximately 90% or greater.

Embodiment 38. The method of any one of embodiments 25-37, wherein the RNAi agent is administered to a human subject at a dose of about 0.05 mg/kg to about 5.0 mg/kg of body weight of the human subject.

Embodiment 39. The method of any one of embodiments 25-37, wherein the RNAi agent is administered to a human subject at a dose of about 25 mg, about 50 mg, about 100 mg, about 200 mg, about 250 mg, about 300 mg, about 350 mg, or about 400 mg.

Embodiment 40. The method of embodiment 39, wherein the RNAi agent is administered to a human subject at a dose of about 100 mg, about 200 mg, or about 400 mg.

Embodiment 41. The RNAi agent of any one of embodiments 1-21 or the composition according to any one of embodiments 22-24, for use in the treatment of a disease, disorder, or symptom that is mediated at least in part by dysregulated complement activity, dysregulated C3 activity, or C3 gene expression.

Embodiment 42. The RNAi agent or composition according to embodiment 41, wherein the disease is IgA nephropathy (IgAN), C3 glomerulopathy (C3G), paroxysmal nocturnal hemoglobinuria (PNH), lupus nephritis, primary membranous nephropathy (PMN), autoimmune hemolytic anemia/cold agglutinin disease (AIHA/CAD), and/or another type of complement-mediated renal disease.

Embodiment 43. The RNAi agent of any one of embodiments 1-21 or the composition according to any one of embodiments 22-24, for use in the preparation of a pharmaceutical composition for treating a disease, disorder, or symptom that is mediated at least in part by dysregulated complement activity, dysregulated C3 activity, or C3 gene expression.

Embodiment 44. The RNAi agent or composition according to any one of embodiments 41 to 43, wherein the RNAi agent is administered to a human subject at a dose of about 0.05 mg/kg to about 5.0 mg/kg of body weight of the human subject.

The above provided embodiments and items are now illustrated with the following, non-limiting examples.

EXAMPLES

Example 1. Synthesis of C3 RNAi Agents

C3 RNAi agent duplexes shown in Tables 5A, 5B, 5C, and 8 above, were synthesized in accordance with the following general procedures:

A. Synthesis.

The sense and antisense strands of the RNAi agents were synthesized according to phosphoramidite technology on solid phase used in oligonucleotide synthesis. Such standard synthesis is generally known in the art. Depending on the scale, a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). The monomer positioned at the 3' end of the respective strand was attached to the solid support as a starting point for synthesis. All 2'-modified RNA phosphoramidites were purchased from Thermo Fisher Scientific (Milwaukee, WI, USA) or Hongene Biotech (Shanghai, PRC). The 2'-O-methyl phosphoramidites included the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl amidites. 5'-(4,4'-Dimethoxytrityl)-2',3'-seco-uridine, 2'-benzoyl-3'-[(2-cyanoethyl)-(N,N-diisopropyl)]-phosphoramidite was also purchased from Thermo Fisher Scientific or Hongene Biotech. 5'-dimethoxytrityl-2'-O-methyl-inosine-3'-O-(2-cyanoethyl-N,N-diisopropylamino) phosphoramidites were purchased from Glen Research (Virginia) or Hongene Biotech. The cyclopropyl phosphonate phosphoramidites were synthesized in accordance with International Patent Application Publication No. WO 2017/214112 (see also Altenhofer et. al., Chem. Communications (Royal Soc. Chem.), 57(55):6808-6811 (July 2021)). The inverted abasic (3'-O-dimethoxytrityl-2'-deoxyribose-5'-O-(2-cyanoethyl-N,N-diisopropylamino) phosphoramidites were purchased from ChemGenes (Wilmington, MA, USA) or SAFC (St Louis, MO, USA). 5'-O-dimethoxytrityl-$N^2$,$N^6$-(phenoxyacetate)-2'-O-methyl-diaminopurine-3'-O-(2-cyanoethyl-N,N-diisopropylamino) phosphoramidites were obtained from ChemGenes or Hongene Biotech.

Targeting ligand-containing phosphoramidites were dissolved in anhydrous dichloromethane or anhydrous acetonitrile (50 mM), while all other amidites were dissolved in anhydrous acetonitrile (50 mM), or anhydrous dimethylformamide and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 12 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, MA, USA) in anhydrous Acetonitrile was employed. Each of the C3 RNAi agent duplexes synthesized and tested in the following Examples utilized N-acetyl-galactosamine as "NAG" in the targeting ligand chemical structures represented in Table 6. (NAG37) and (NAG37)s targeting ligand phosphoramidite compounds can be synthesized in accordance with International Patent Application Publication No. WO 2018/044350 to Arrowhead Pharmaceuticals, Inc.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of filtered DI water or 100 mM ammonium bicarbonate, pH 6.7 and 20% Acetonitrile.

D. Annealing.

Complementary strands were mixed by combining equimolar RNA solutions (sense and antisense) in 1×Phosphate-Buffered Saline (Corning, Cellgro) to form the RNAi agents. Some RNAi agents were lyophilized and stored at −15 to −25° C. Duplex concentration was determined by measuring the solution absorbance on a UV-Vis spectrometer in 1×Phosphate-Buffered Saline. The solution absorbance at 260 nm was then multiplied by a conversion factor and the dilution factor to determine the duplex concentration. The conversion factor used was either 0.050 mg/(mL-cm) or was calculated from an experimentally determined extinction coefficient.

Example 2. In Vivo Testing of C3 RNAi Agents in Cynomolgus Monkeys

C3 RNAi agent AD09546 was evaluated in cynomolgus monkeys (cynos). On days 1 and 29, three male cynos for each group (n=3) were administered a subcutaneous injection of 0.3 mL/kg (approximately 1.5 mL volume, depending on animal mass) containing either 0.5 mg/kg (mpk), 1.5 mg/kg, or 4.5 mg/kg of the C3 RNAi agent, formulated in isotonic saline.

TABLE 9

Targeted Positions and Dosing Groups of Example 2

| Group | Targeted Gene Position (within SEQ ID NO: 1) | RNAi Agent and Dose | Dosing Regimen (on days 1 and 29) |
| --- | --- | --- | --- |
| 1 | 2566 | 0.5 mg/kg AD09546 | Two subcutaneous injections |
| 2 | 2566 | 1.5 mg/kg AD09546 | Two subcutaneous injections |
| 3 | 2566 | 4.5 mg/kg AD09546 | Two subcutaneous injections |

The C3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, 6, 7A, 7B, and 8 for specific modifications and structure information related to the C3 RNAi agents, including (NAG37)s ligand). The C3 RNAi agents included nucleotide sequences that were designed to inhibit expression of a human C3 gene at position 2566. (See, e.g., SEQ ID NO:1).

On days −7 (pre-dose), 1 (pre-dose), 8, 15, 22, 29, 36, 43, 50, 57, 64, 71, 78, and 85 serum was collected. FIG. 1 shows serum cynomolgus monkey C3 protein normalized to predose levels, with each serum collection date measured by week (e.g., in FIG. 1, week 0 is day 1, week 4 is day 29, and week 12 is day 85).

Additionally, hemolysis activity was assessed. Hemolysis activity is sensitive to the reduction, absence, and/or inactivity of key components of the complement system. As noted, there are three pathways of complement activation: the alternative pathway, the classical pathway, and the lectin pathway. As all three activation pathways of the complement system require engagement of C3 to cause tissue injury in vivo (see, e.g., Thurman, J. & Holers, V. M., J. Immunol. Feb. 1, 2006, 176(3) 1305-1310), the activation of the alternative pathway of complement (AP) was measured to assess the effect of C3 knockdown to the complement system. The AP requires only $Mg^{2+}$ ions, whereas the classical and lectin pathways require both $Ca^{2+}$ and $Mg^{2+}$. This difference was used to assay only the AP in the presence of classical and lectin pathway proteins. Rabbit erythrocytes, which are known to spontaneously activate AP in most mammalian species, was applied in conducting the assay.

Figure 2:
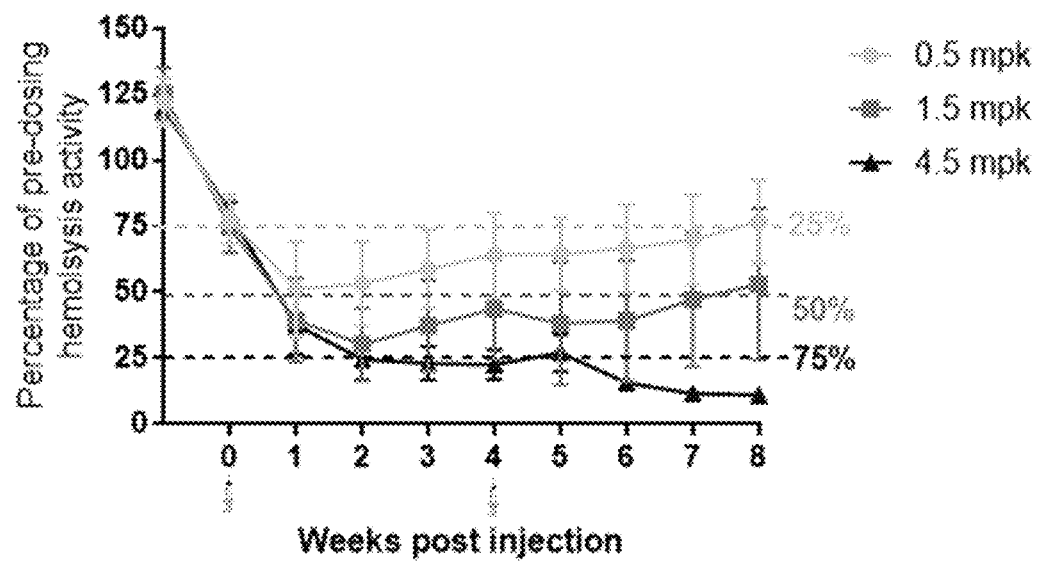
FIG. 2. Graph showing percentage of pre-dosing hemolysis activity in cynomolgus monkeys, pursuant to the study described in Example 2.

To perform the hemolysis activity assay, 10 µL of cynomolgus monkey serum was first diluted in 10 µL of GVB buffer (Catalog number B103, Complement Technology, Inc), and was then further diluted with another 50 µL of the same buffer. To that was added 5 uL of 0.1M MgEGTA (Catalog number B106, Complement Technology, Inc) and 25 µL of rabbit erythrocytes (Catalog number B302, Complement Technology, Inc). Thus, the mixture used a 10× dilution of each collected serum sample (10% of final serum concentration; total volume 100 µL at this step, $1.25×10^7$ rabbit erythrocytes). The lysis of rabbit erythrocytes was evaluated after 15 min incubation with the serum at 37° C. At the end of the reaction, 100 µL of cold GVBE (Catalog number B104, Complement Technology, Inc) was added to stop the reaction (final volume=200 µL). Maximum lysis was determined by the identical number of rabbit erythrocytes completely lysed with 2% Tween 20 with 60 min incubation at 37° C. The supernatant of each reaction was transferred to a new ELISA plate and read at 412 nm. The hemolysis activity was determined using the following equation: (reading-background)/(max hemolysis reading-background)×100%. FIG. 2 shows the percentage of pre-dosing hemolysis activity (AP) through week 8 (day 57). For each individual animal, the percentage of remaining hemolysis activity of samples collected from at all the time points in this study were normalized by the average hemolysis levels of Day −7 and Day 1 from the same corresponding animal.

As shown in FIGS. 1 and 2, maximum serum C3 reductions of approximately 84.3% was obtained with associated reduction in hemolytic activity. Further, a long duration of effect was seen, supporting that dosing every three months or every six months with AD09546 may be possible.

Additionally, the collected serum samples were assessed for C3a. Complement C3a is made of 75 amino acid residues and released from complement C3 on activation of complement system to stimulate immune systems (Yoshikawa, Handbook of Biologically Active Peptides, Second Edition, 2013, Chapter 214: 1570-1576). Therefore, serum C3a levels are an indicator of complement C3-related activity. Serum C3a levels were quantified via ELISA using BD OptEIA Human C3a ELISA Kit (Cat #: 550499, BD Biosciences). Standard assay procedure was followed as provided by BD Biosciences. For sample dilutions, 500× and 2000× dilutions were prepared.

Figure 5:
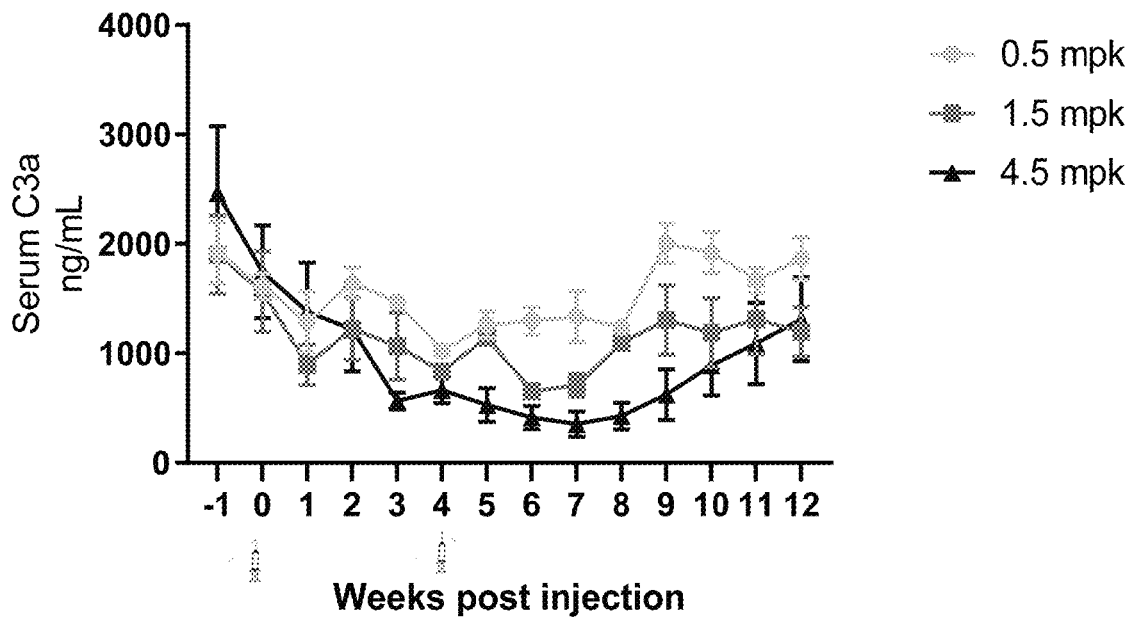
FIG. 5. Graph showing the absolute serum cynomolgus monkey C3a protein levels, pursuant to the study described in Example 2.
Figure 6:
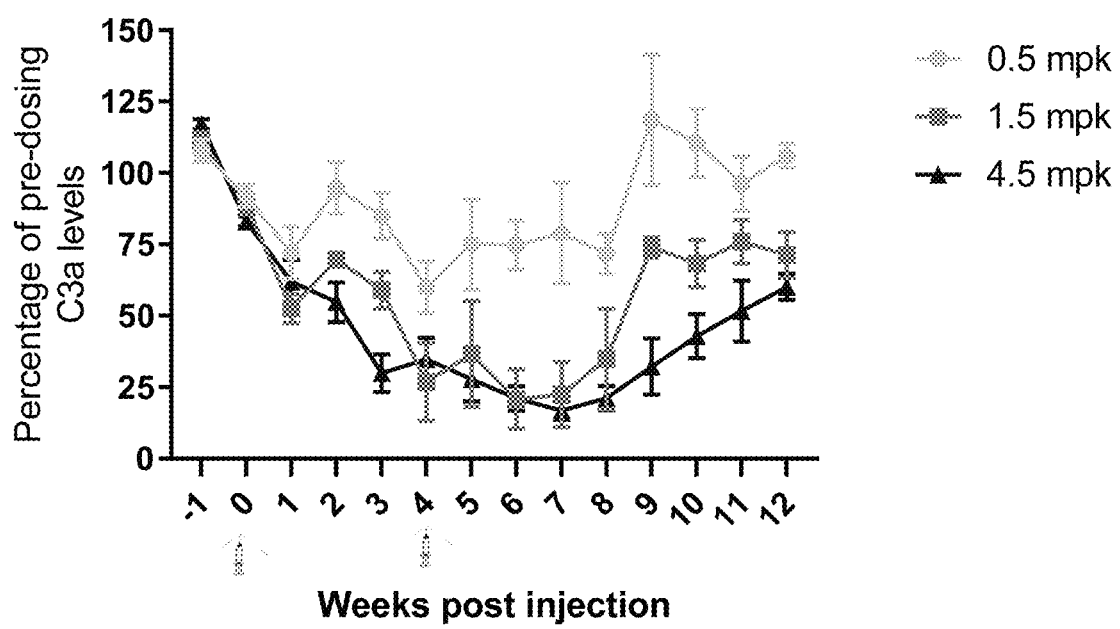
FIG. 6. Graph showing percentage of pre-dosing C3a protein levels in cynomolgus monkeys, pursuant to the study described in Example 2.
Figure 7:
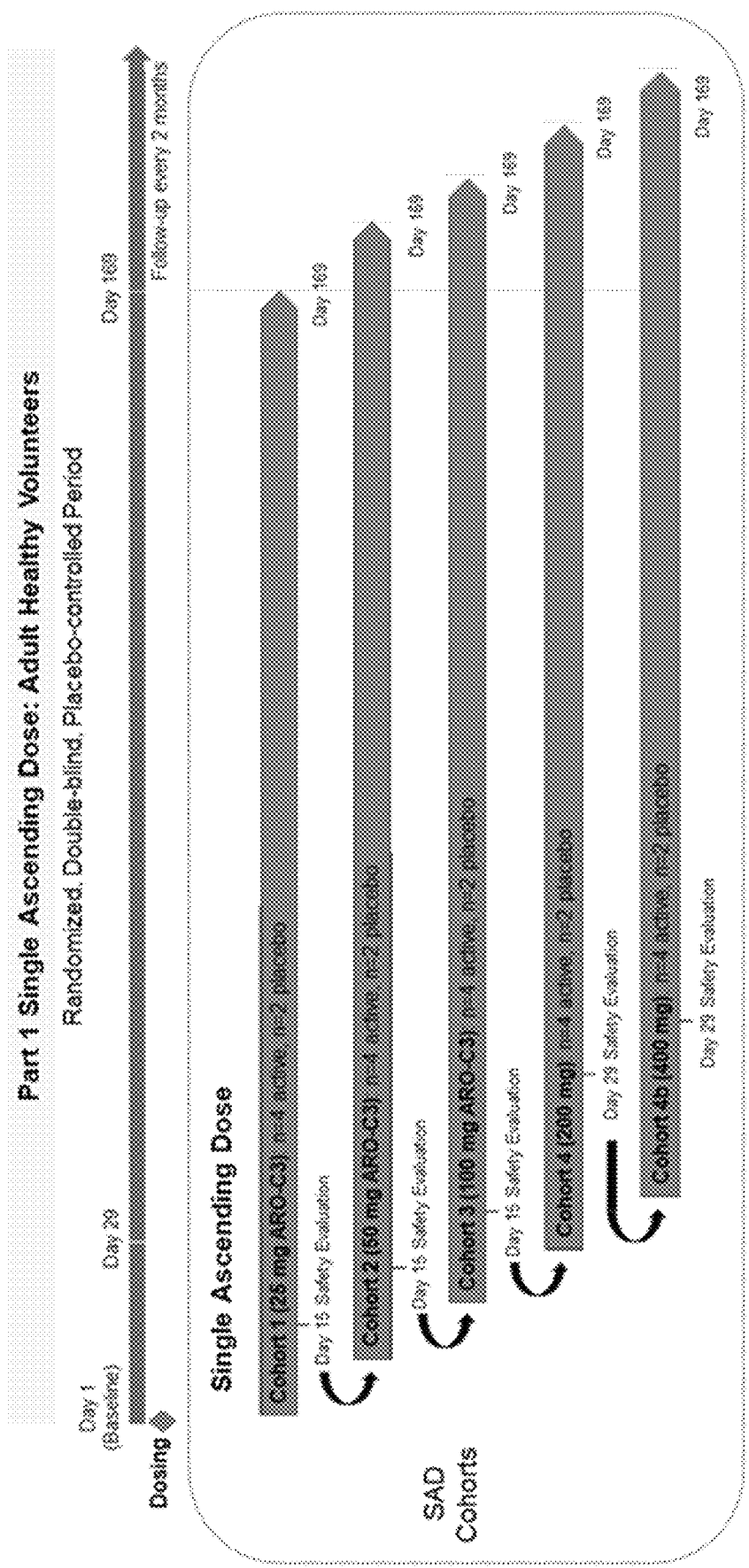
FIG. 7. Updated clinical trial study design and dose escalation schedule for the single ascending dose (SAD) Normal Health Volunteer (NHV) portion (Part 1) of the Phase I/II clinical study described in Example 3. "ARO-C3" refers to the Formulated C3 RNAi Drug Substance.
Figure 8:
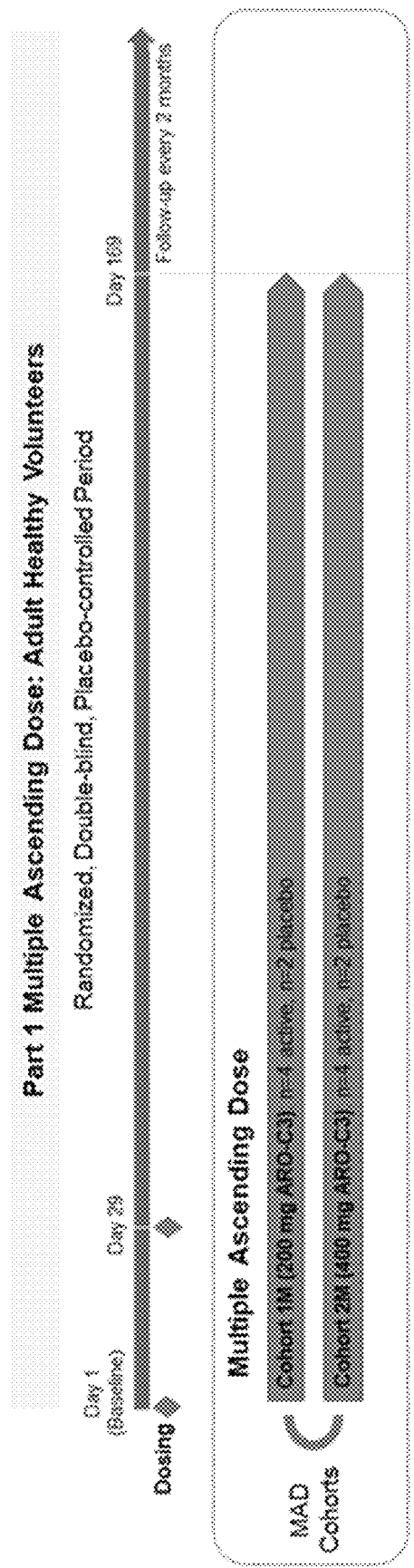
FIG. 8. Updated clinical trial study design and dose escalation schedule for the multiple ascending dose (MAD) NHV portion (Part 1) of the Phase I/II clinical study described in Example 3. "ARO-C3" refers to the Formulated C3 RNAi Drug Substance.
Figure 9:
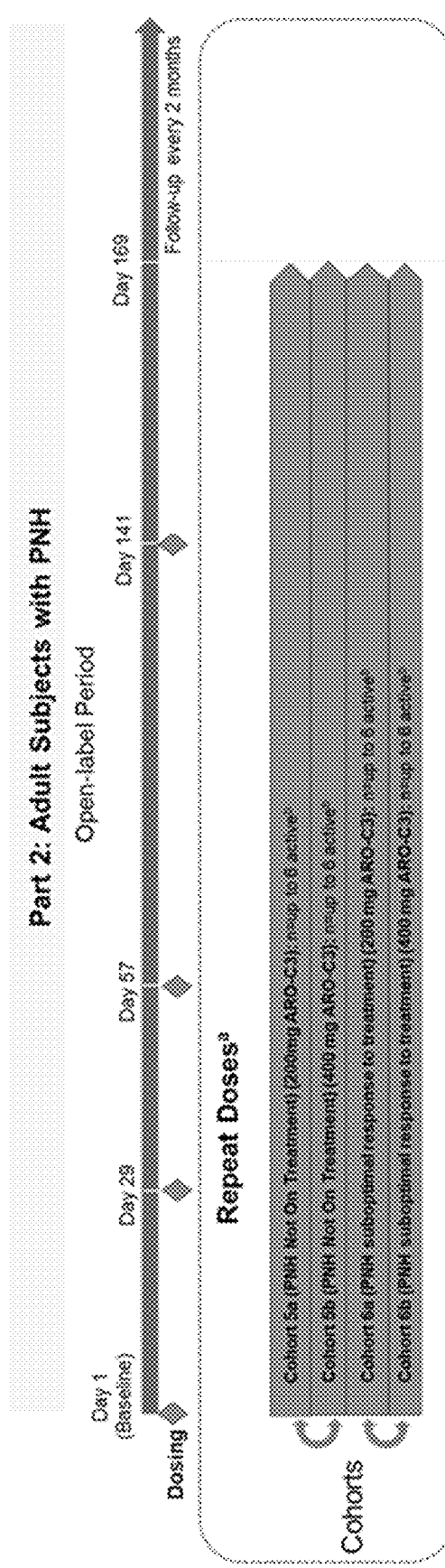
FIG. 9. Updated clinical trial study design and dose escalation schedule for the PNH Patient Cohorts (Part 2) of the Phase I/II clinical study described in Example 3. "ARO-C3" refers to the Formulated C3 RNAi Drug Substance.
Figure 10:
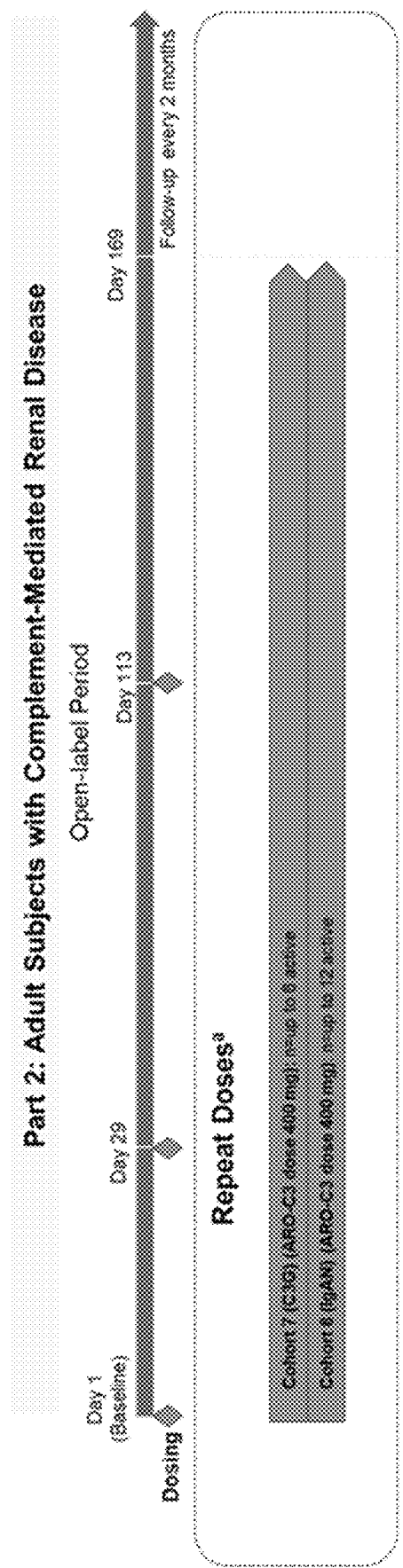
FIG. 10. Updated clinical trial study design and dose escalation schedule for the C3G and IgAN Patient Cohorts (Part 2) of the Phase I/II clinical study (Part 2) described in Example 3. "ARO-C3" refers to the Formulated C3 RNAi Drug Substance.

FIG. 5 shows the absolute C3a levels over time. FIG. 6 shows the relative C3a levels as percentage of pre-dose C3a levels. As shown in FIG. 6, maximum serum C3a reductions of approximately 85% was obtained with associated C3-related activity, at 7 weeks post injection with 4.5 mg/kg of RNAi agent AD09546.

Example 3. Phase I/IIa Clinical Trial of C3 RNAi Drug Substance in Healthy Human Volunteers and Adult Subjects IgA Nephropathy (IgAN) and C3 Glomerulopathy (C3G)

Figure 3:
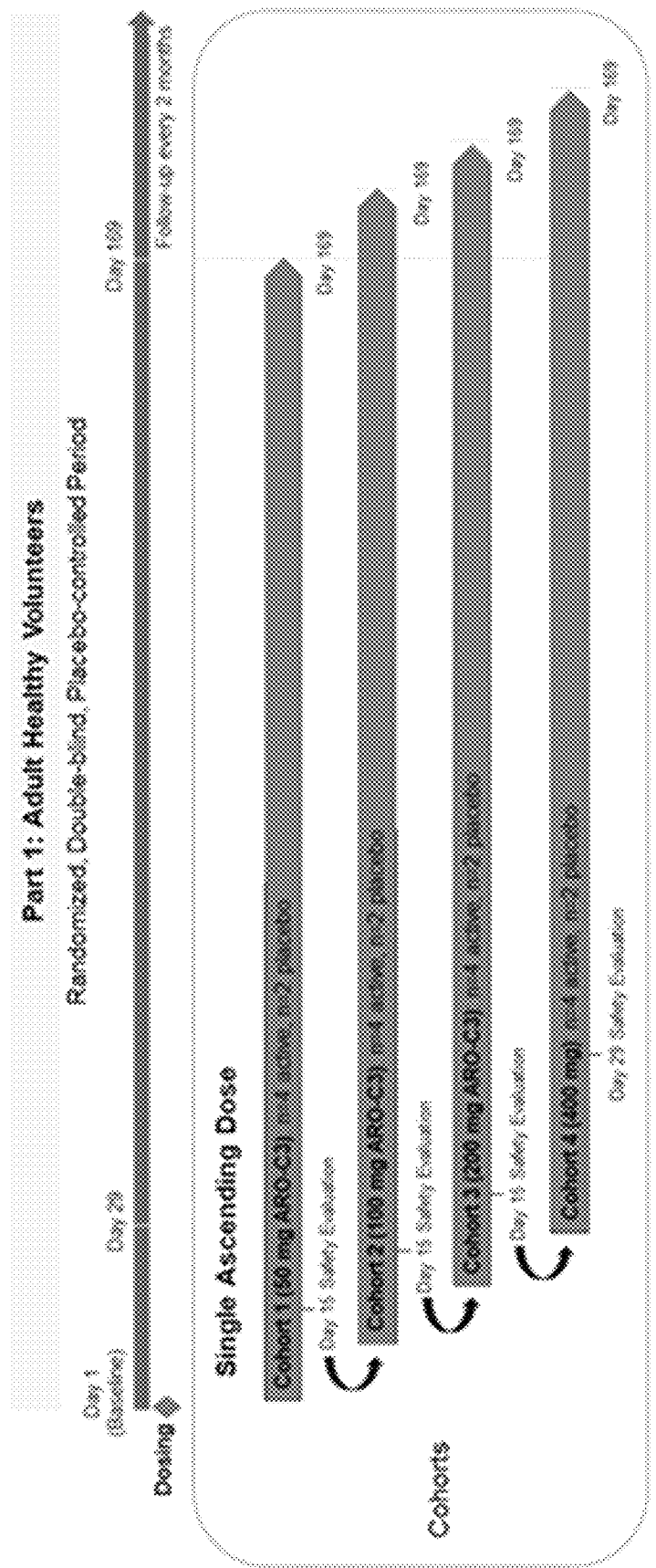
FIG. 3. Preliminary clinical trial study design and dose escalation schedule for the Normal Health Volunteer portion (Part 1) of the Phase I/II clinical study described in Example 3. "ARO-C3" refers to the Formulated C3 RNAi Drug Substance.
Figure 4:
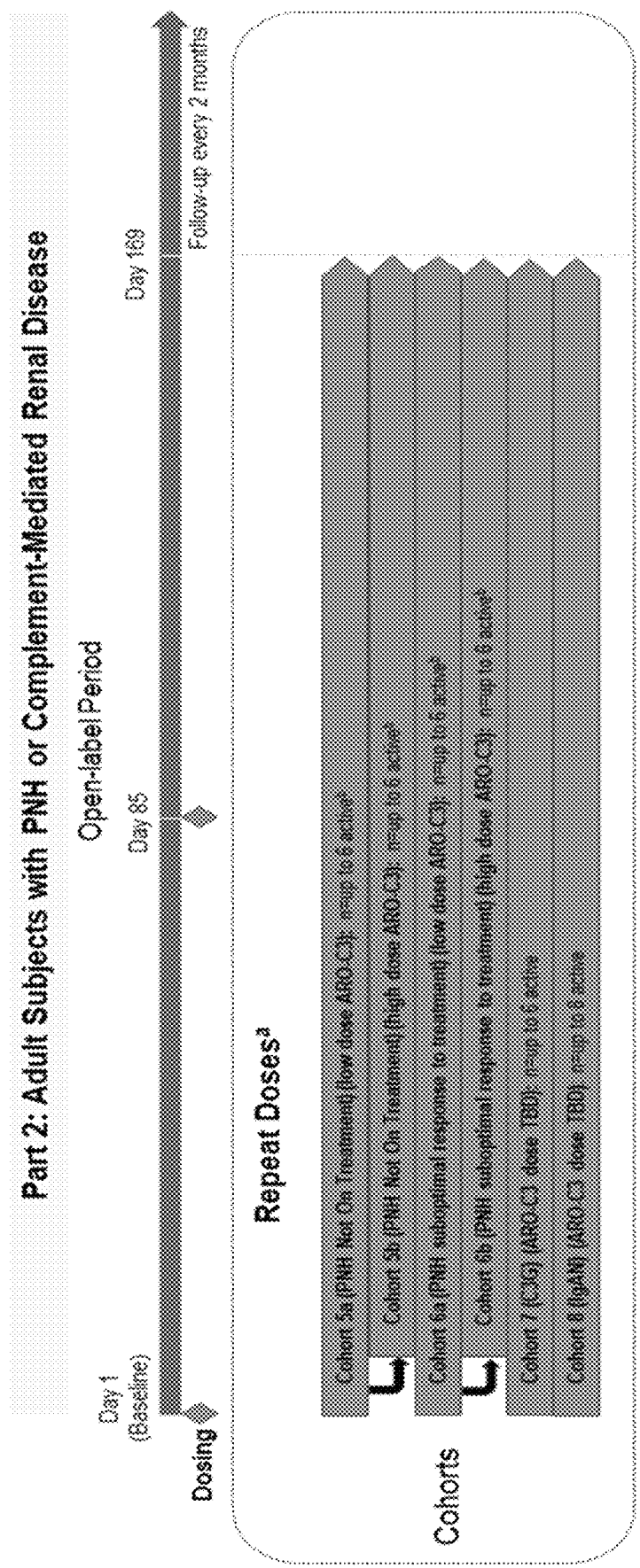
FIG. 4. Preliminary Clinical trial study design and dose escalation schedule for the Patient Cohorts (Part 2) of the Phase I/II clinical study described in Example 3. "ARO-C3" refers to the Formulated C3 RNAi Drug Substance.

A Phase 1/2a, single and multiple dose-escalating study to evaluate the safety, tolerability, pharmacokinetics and pharmacodynamic effects of C3 RNAi Drug Substance described in Table 8 formulated in sodium phosphate buffer in adult healthy volunteers as well as in subjects with IgA nephropathy (IgAN) and C3 glomerulopathy (C3G), was initiated. The C3 RNAi Drug Substance described in Table 8 was formulated at 200 mg/mL in an aqueous sodium phosphate buffer (0.5 mM sodium phosphate monobasic, 0.5 mM sodium phosphate dibasic) ("Formulated C3 RNAi Drug Substance"). FIG. 3 shows the preliminary clinical trial design for the adult healthy volunteer cohorts, and FIG. 4 shows the preliminary clinical trial design for adult subjects with C3G and IgAN. The clinical trial design was revised as shown in FIGS. 7, 8, 9 and 10. Prior to dosing any patients, it was determined to not include patients with paroxysmal nocturnal hemoglobinuria (PNH) at this time.

Five single-ascending-dose (SAD) cohorts each enrolled 6 normal healthy volunteer (NHV) subjects (randomized 2:1 drug:placebo) to receive Formulated C3 RNAi Drug Substance at a dose of 25 mg, 50 mg, 100 mg, 200 mg, or 400 mg, or placebo (i.e., 4 subjects received C3 RNAi Drug Substance and 2 subjects received placebo in each cohort). Two dose levels (200 mg and 400 mg) were further examined in multiple-ascending-dose (MAD) cohorts, enrolling 6 NHV subjects in each cohort (randomized 2:1 drug:placebo) to receive Formulated C3 RNAi Drug Substance or placebo on Day 1 and Day 29.

In NHVs, Formulated C3 RNAi Drug Substance was considered generally well-tolerated with no drug-related serious adverse events (SAEs), no study discontinuations due to adverse events (AEs), no clinically significant laboratory findings, and no patterns of adverse changes in any clinical laboratory parameters were reported.

Total C3 protein levels in serum samples were measured by nephelometry. A known quantity of anti-C3 antibody was included in the assay matrix, and C3 was then determined by using a Beckman Immage 800 Immunochemistry System to measure the rate of increase in light scattered from particles suspended in solution as a result of complexes formed during the antigen-antibody reaction.

The alternative complement pathway hemolytic activity (AH50) was also assessed by using a typical hemolytic assay based on lysis of rabbit red blood cells (RA) due to activation of complement on the cell's surface. The AH50 (50% complement hemolytic dose) was determined for each component by adding a limiting amount of the test sample. Serial dilutions of the test sample were mixed with equal volumes of the RA. The amount of hemoglobin that was released when the target cells were lysed by the action of complement was measured, and from this the percentage of the cells that had been lysed was calculated. With the cell concentration used in this Example, the most sensitive wavelength to use was 415 nm, the major peak of the hemoglobin spectrum. For each assay the run was verified with a five point standard and five points of characterized QC control.

Additionally, reductions in C3 can also be correlated with compromised alternative pathway of complement (AP) activity, and were measured by the Wieslab® AP assay. The Wieslab® AP assay is an ELISA-based assay that detects the complement membrane attack complex (MAC), which is a cytolytic effector of immunity at the final step of the complement cascade. As the plate is coated with specific activator of the alternative pathway, the commercially-available kit (COMPLAP330RUO, SVAR Life Sciences, Sweden) is alternative-pathway specific. The results described herein were calculated using negative and positive control samples per manufacturer's protocol.

Figure 11:
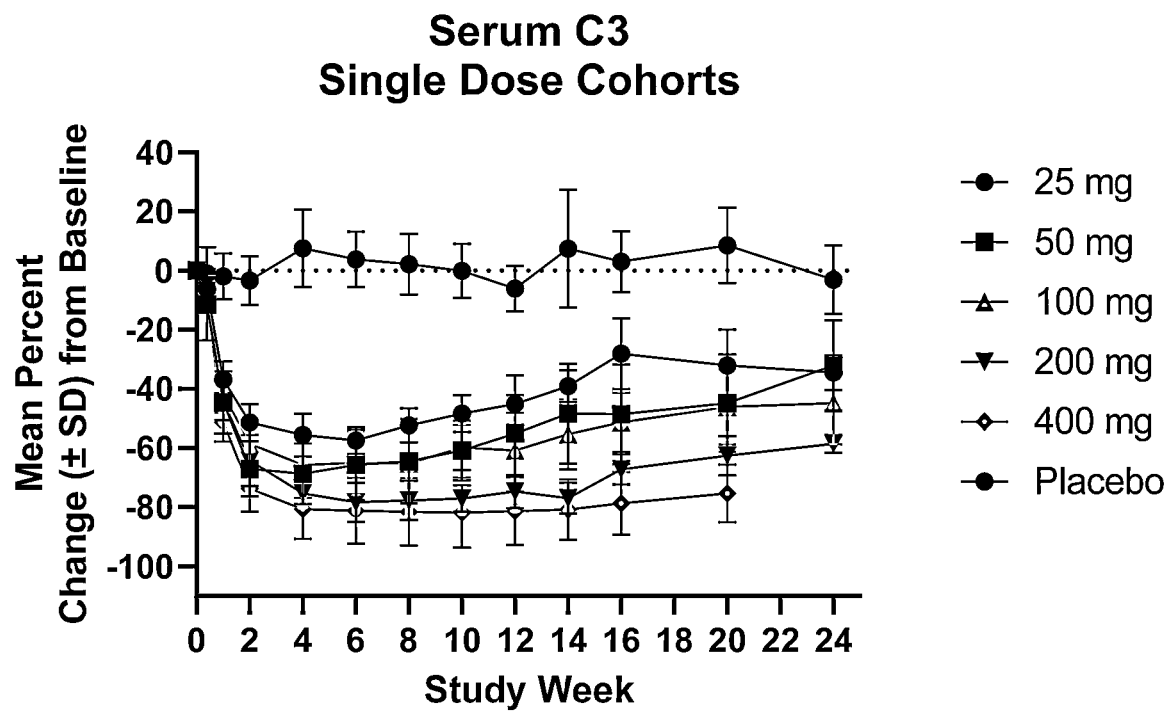
FIG. 11. Graph showing serum human C3 protein levels in subjects from the single ascending dose (SAD) portion of the Phase I/II clinical study described in Example 3, in normal human volunteers (NHVs).
Figure 13:
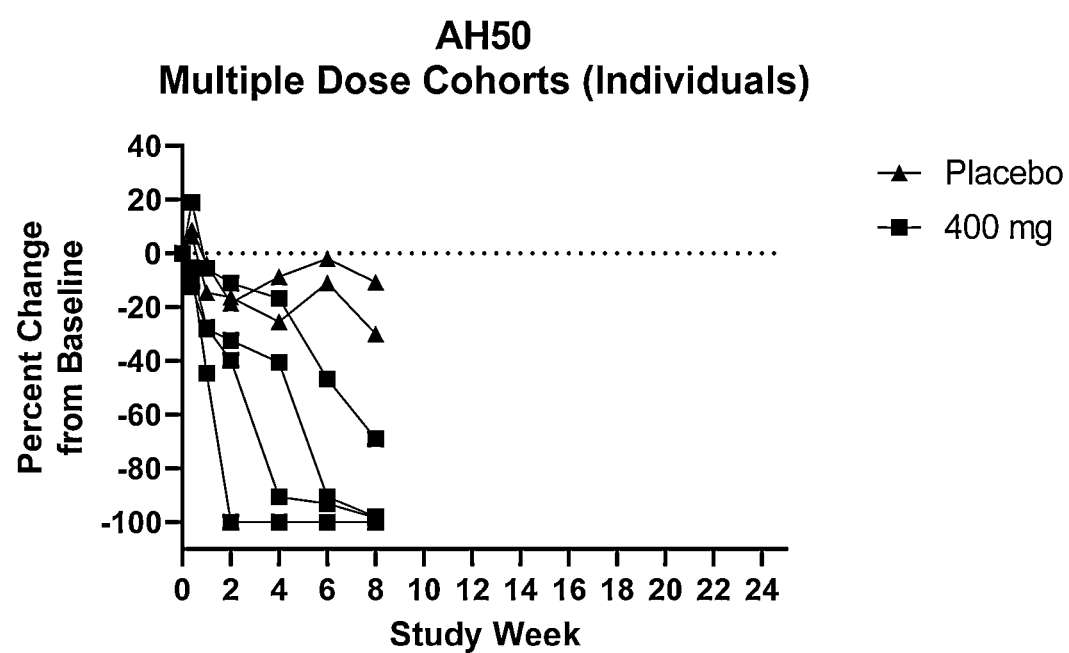
FIG. 13. Graph showing AH50 (U/mL) in individual subjects who received 400 mg Formulated C3 RNAi Drug Substance or placebo on Day 1 and Day 29 from the multiple ascending dose (MAD) portion of the Phase I/II clinical study described in Example 3, in normal human volunteers (NHVs).
Figure 14:
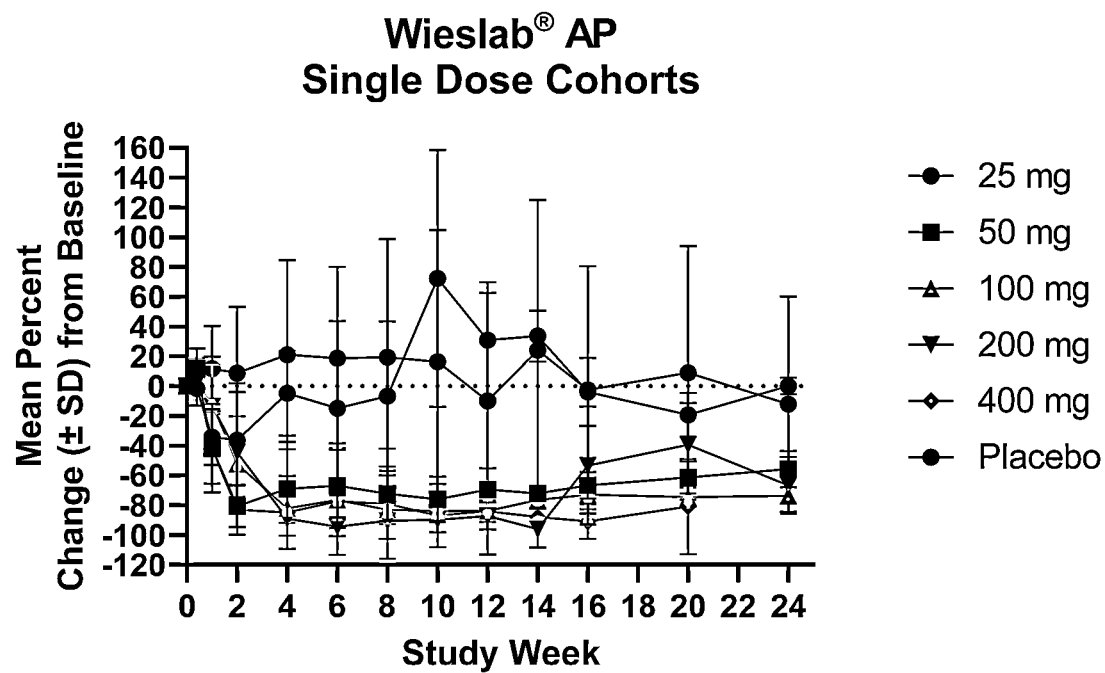
FIG. 14. Graph showing Wieslab® AP assay results from the single ascending dose (SAD) portion of the Phase I/II clinical study described in Example 3, in normal human volunteers (NHVs). The results were calculated using negative and positive control samples per manufacturer's protocol.
Figure 15:
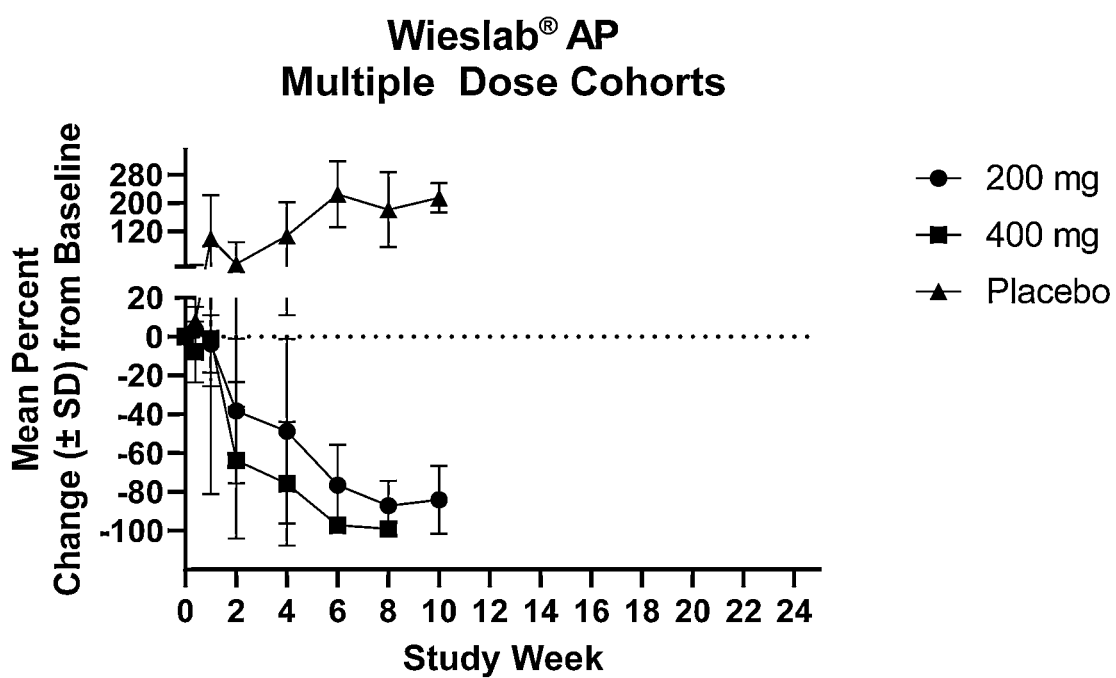
FIG. 15. Graph showing Wieslab® AP assay results from the multiple ascending dose (MAD) portion of the Phase I/II clinical study described in Example 3, in normal human volunteers (NHVs). The results were calculated using negative and positive control samples per manufacturer's protocol.
Figure 16A:
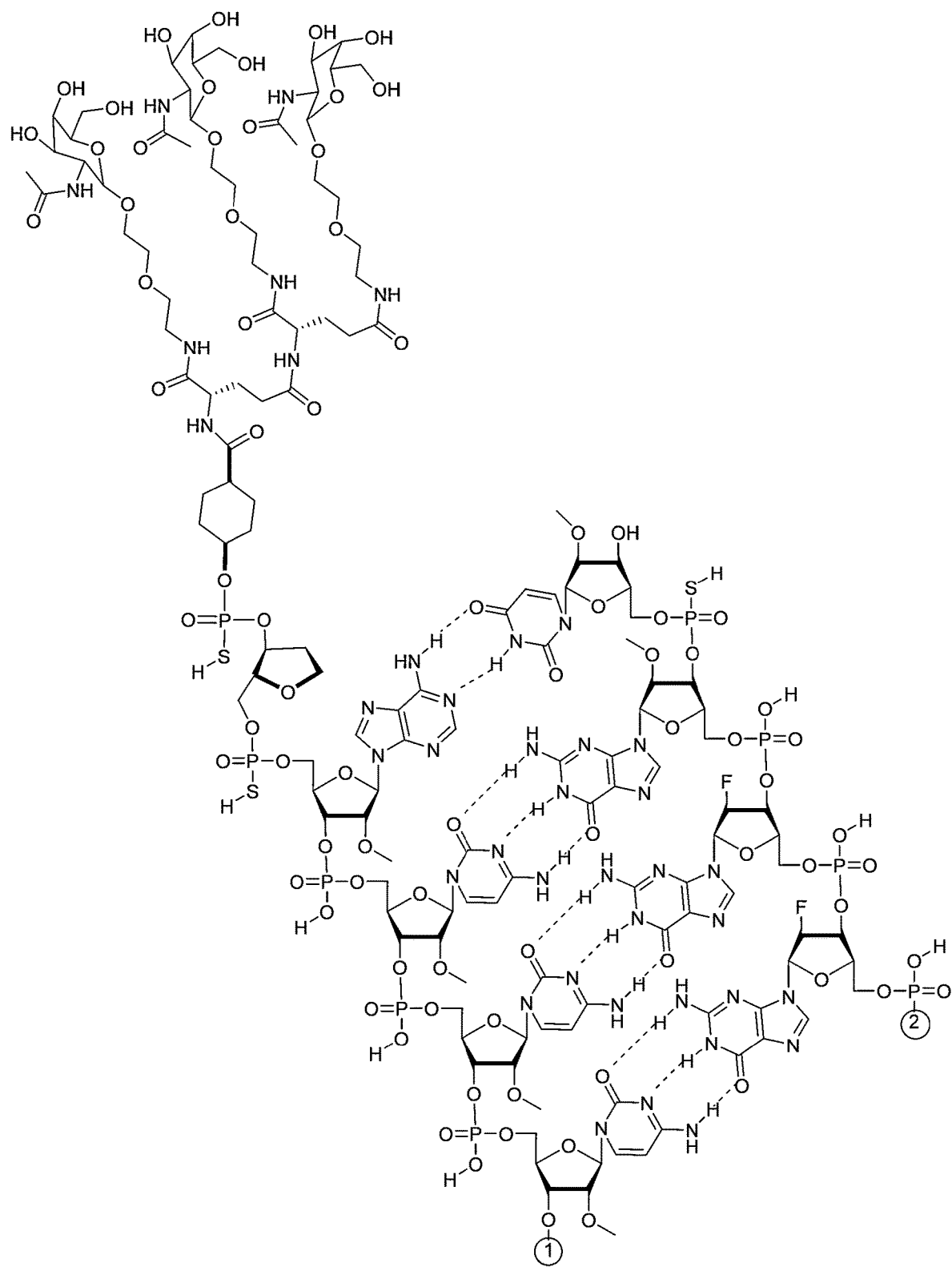
FIG. 16A through 16D. Chemical structure of the C3 RNAi Drug Substance shown in the free acid form (see, e.g., Table 8; RNAi agent AD09546 (SEQ ID NOS: 14/13)).
Figure 16B:
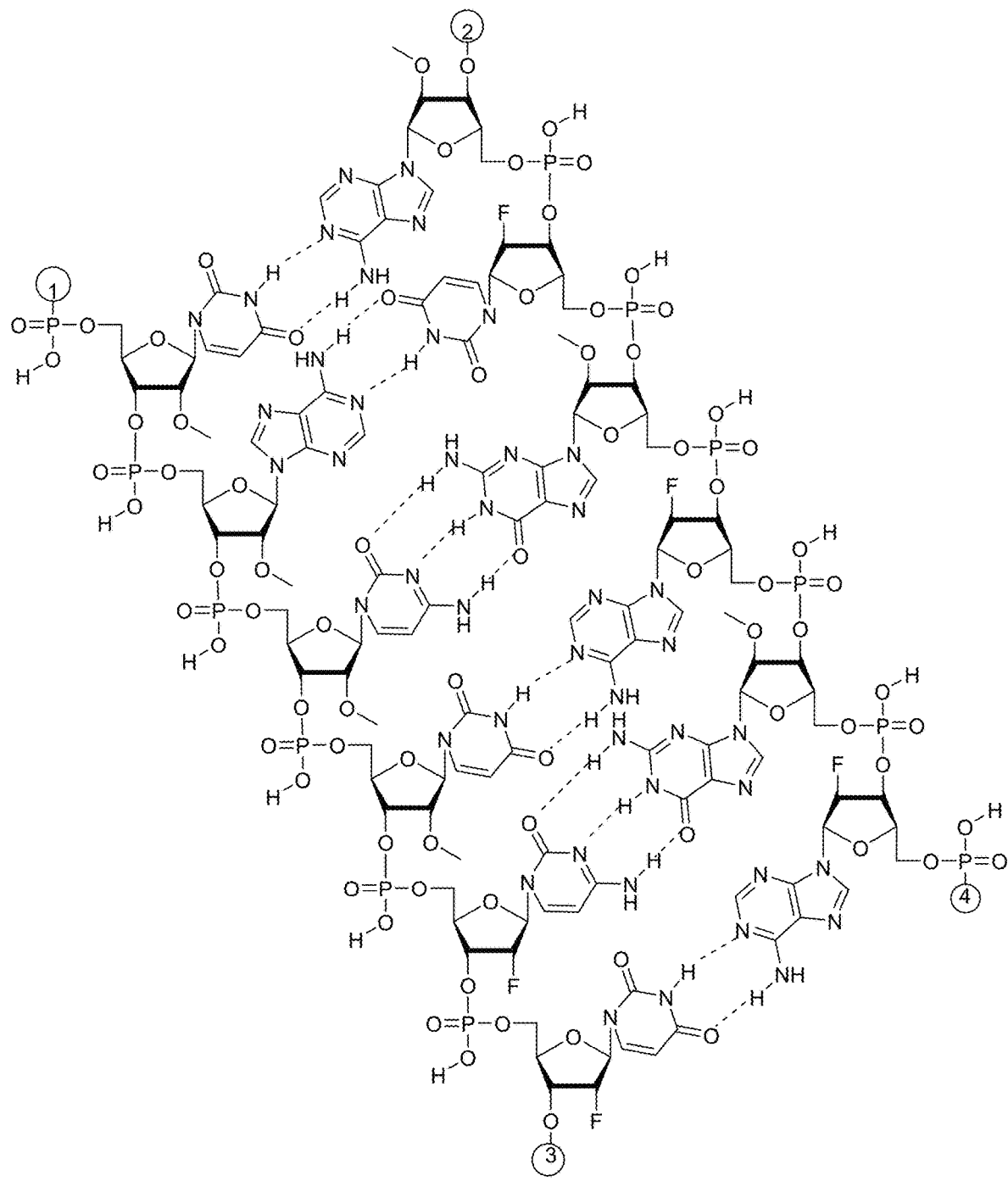
Figure 16C:
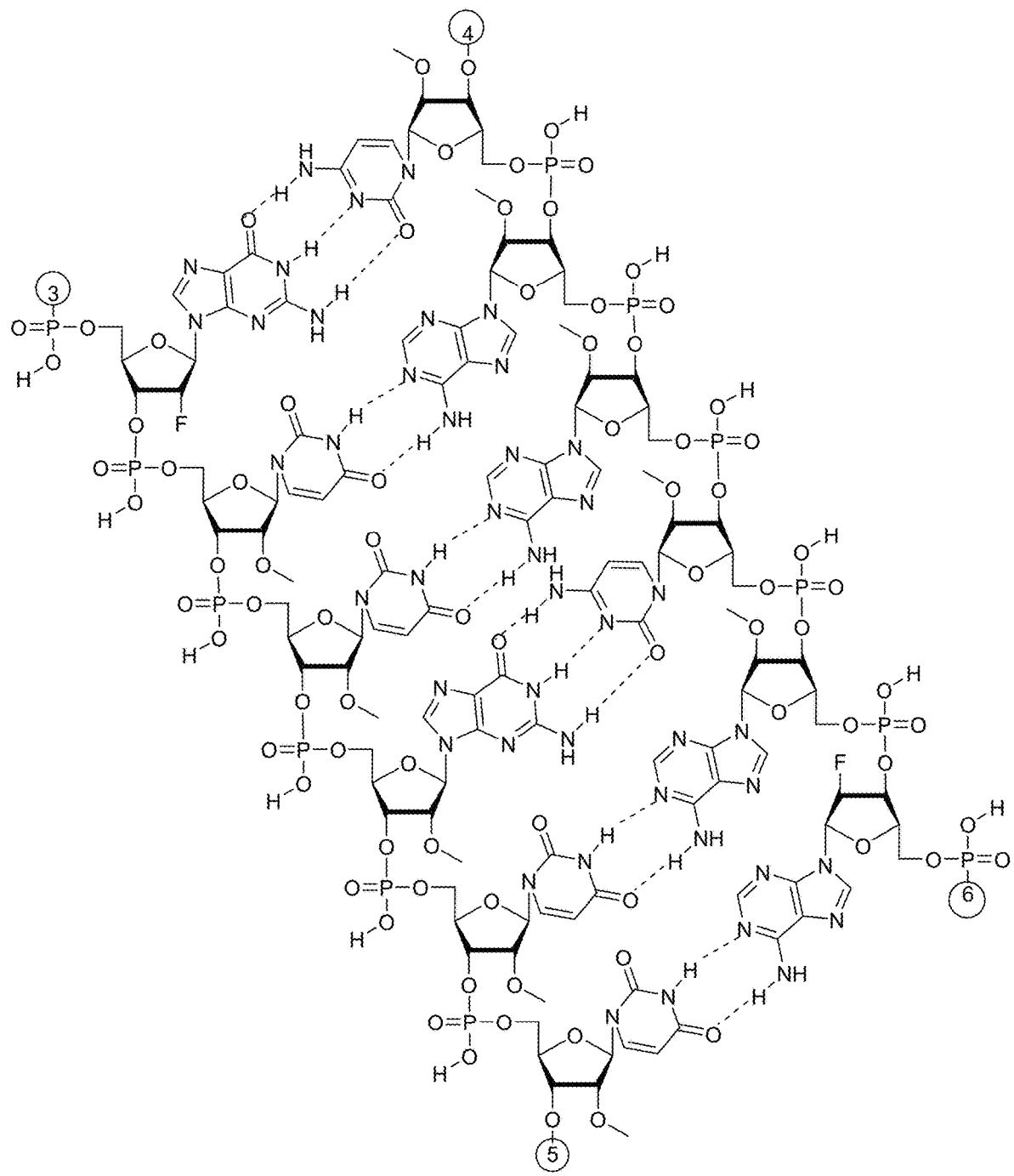
Figure 16D:
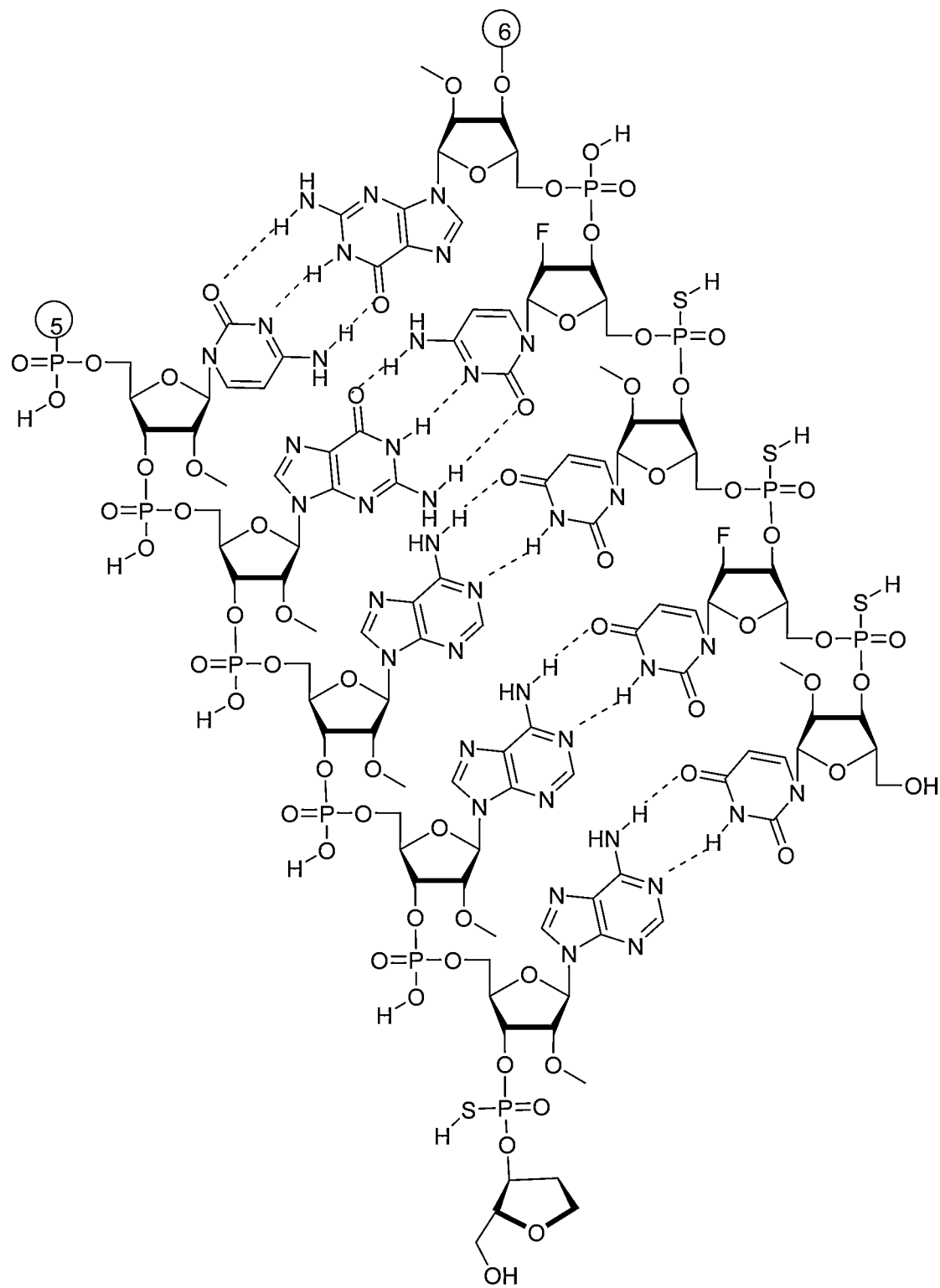
Figure 17A:
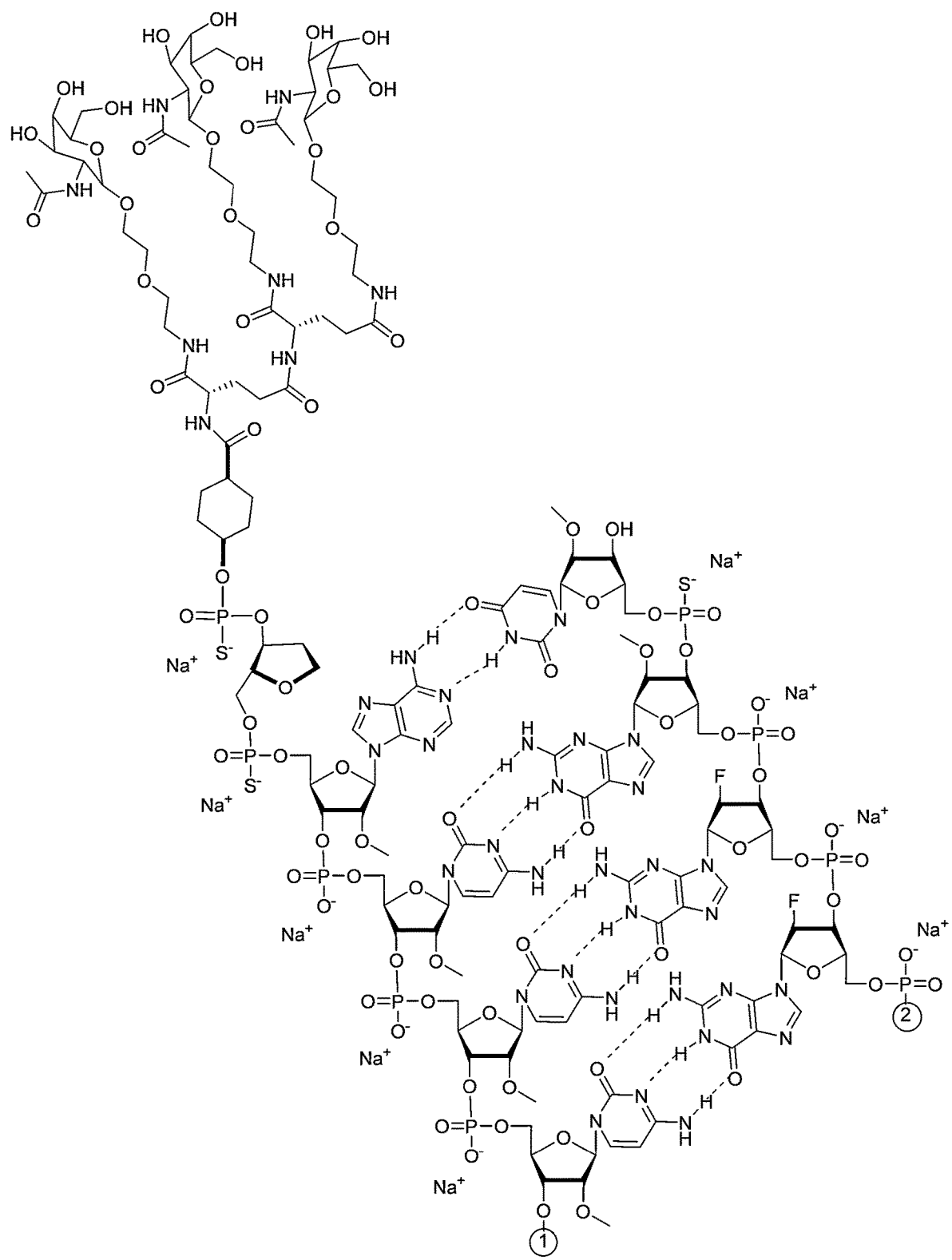
FIG. 17A through 17D. Chemical structure of the C3 RNAi Drug Substance shown in the sodium salt form (see, e.g., Table 8; RNAi agent AD09546 (SEQ ID NOS:14/13)).
Figure 17B:
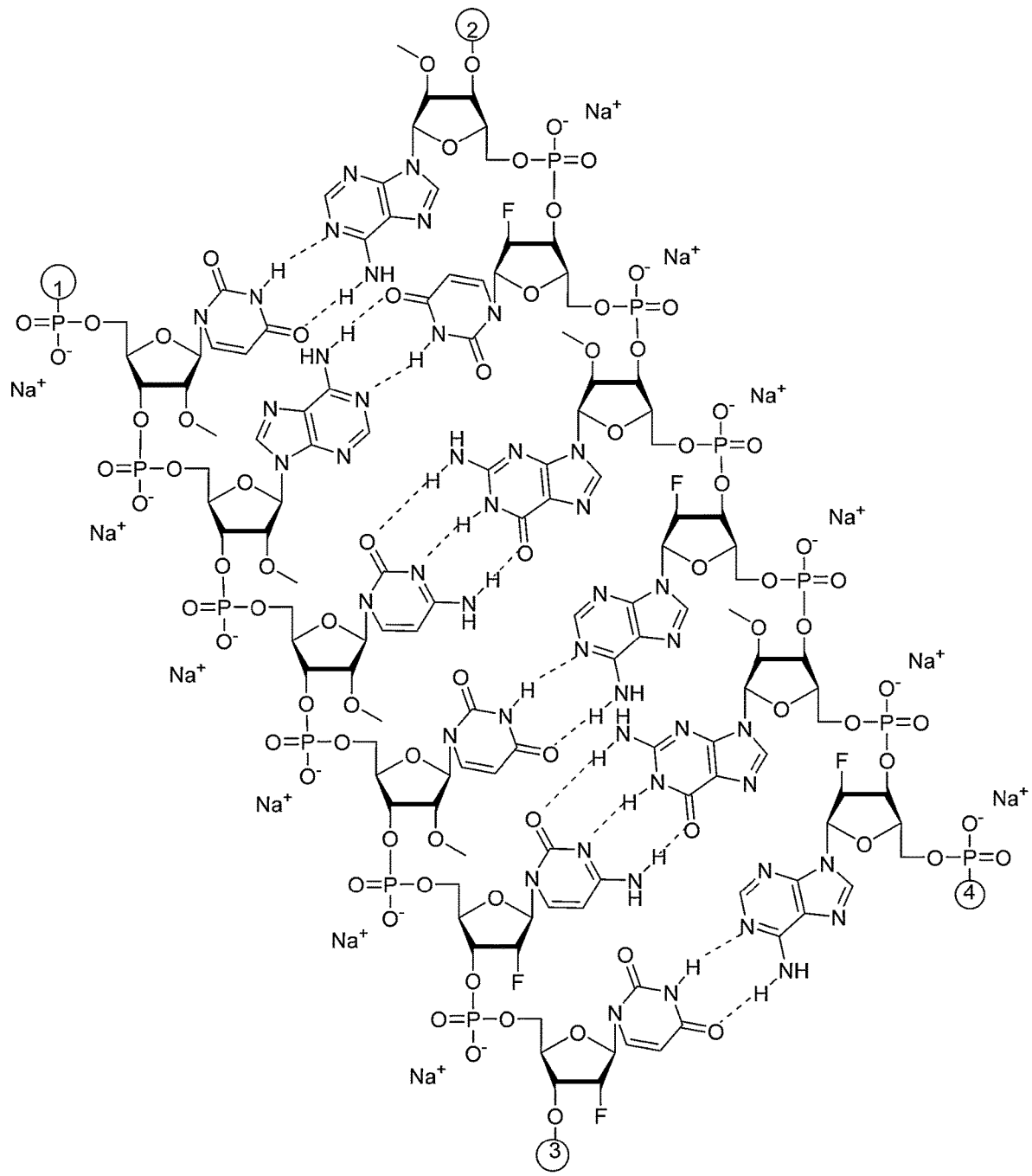
Figure 17C:
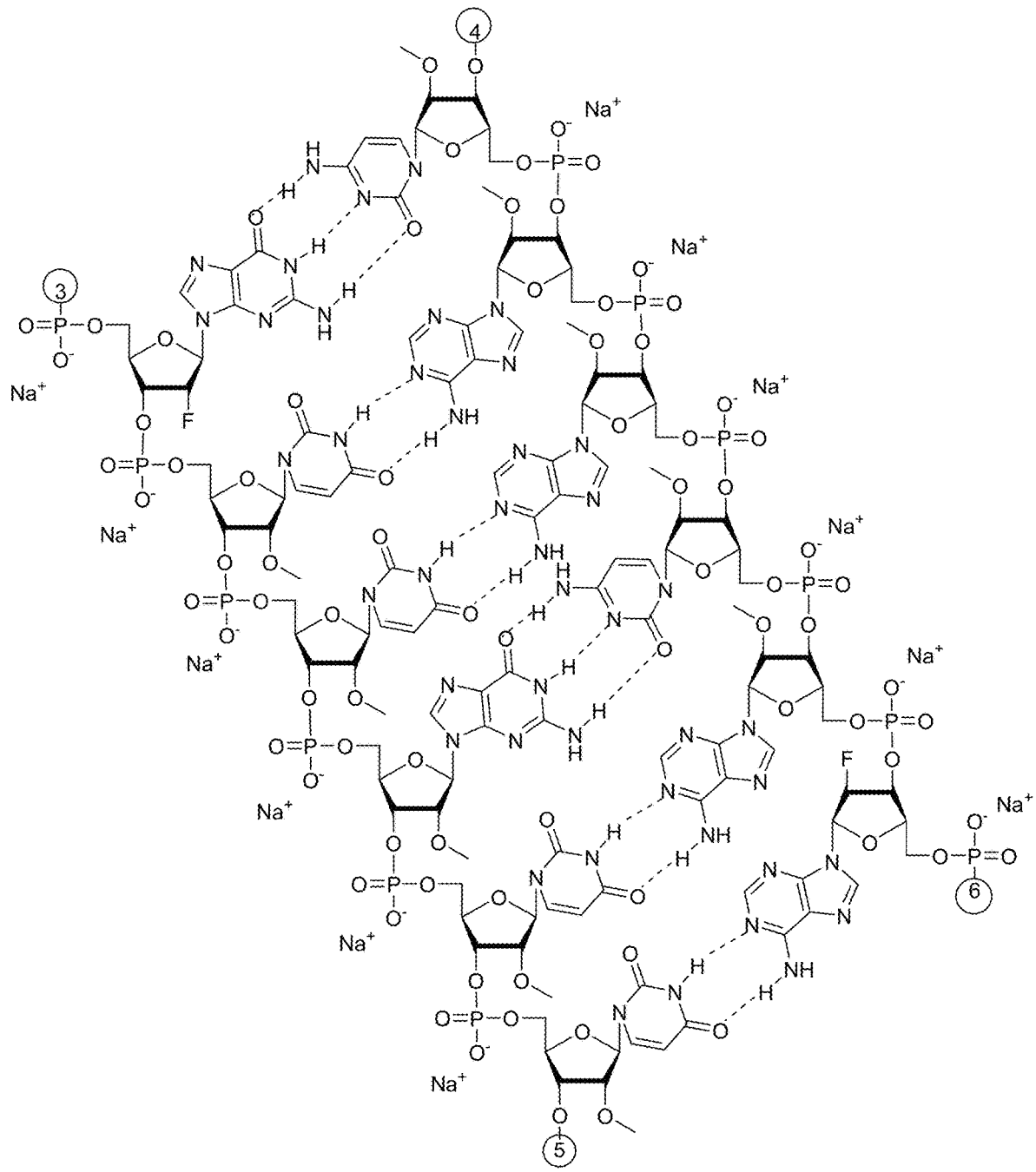
Figure 17D:
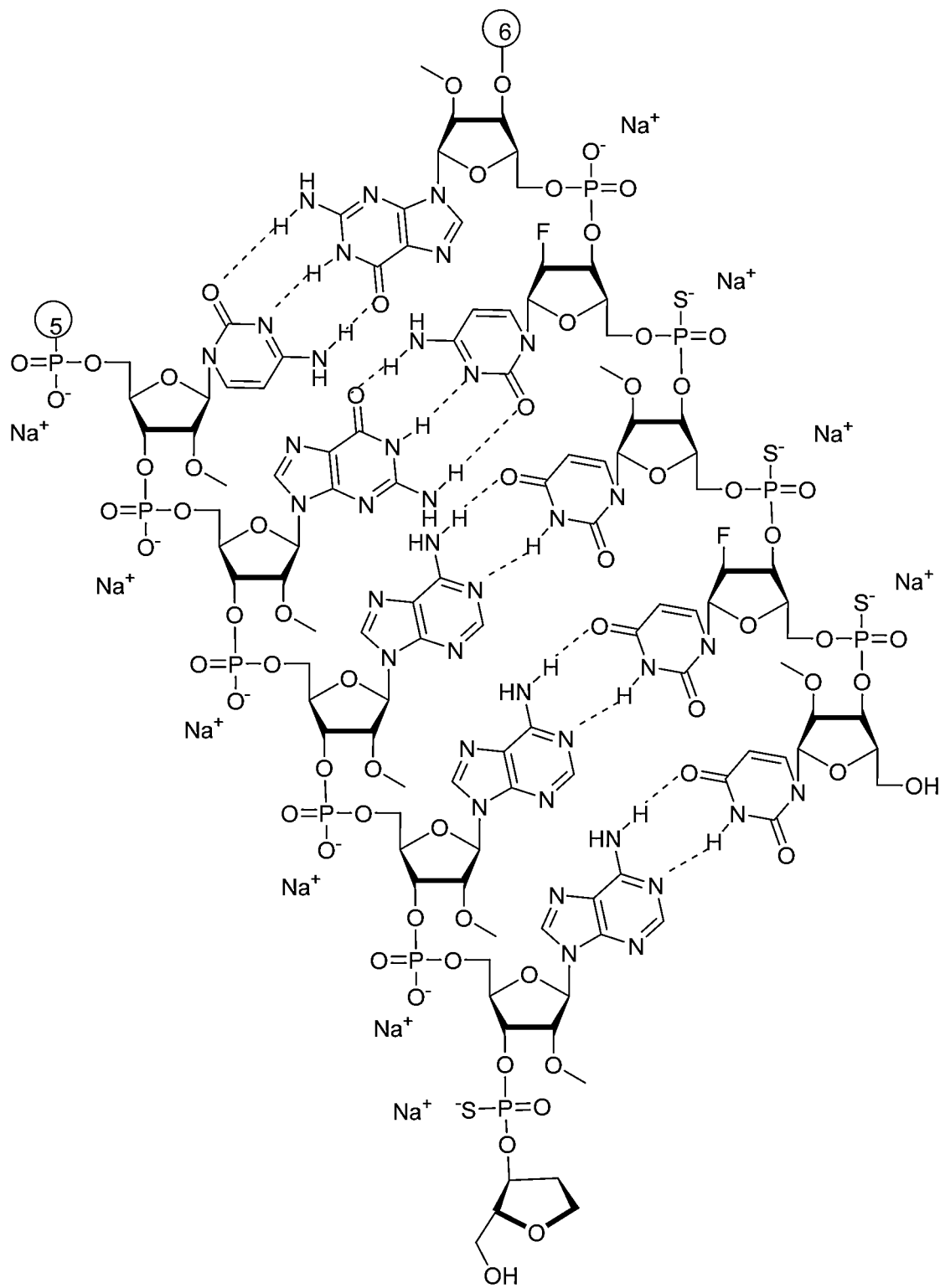

Preliminary data in NHVs showed consistent reductions in C3 serum protein levels across all SAD cohorts, with mean reduction of 80.7% achieved on Day 29 in the 400 mg cohort sustained through week 16 (see, e.g., FIG. 11). The AH50 was also assessed, which for the 400 mg cohort showed a mean reduction in AH50 of up to 68.8% (see FIG. 13). Wieslab® AP was also assessed, which showed for the 400 mg group mean reductions of approximately 85% to 90% that were sustained through week 16 (see FIG. 15).

Figure 12:
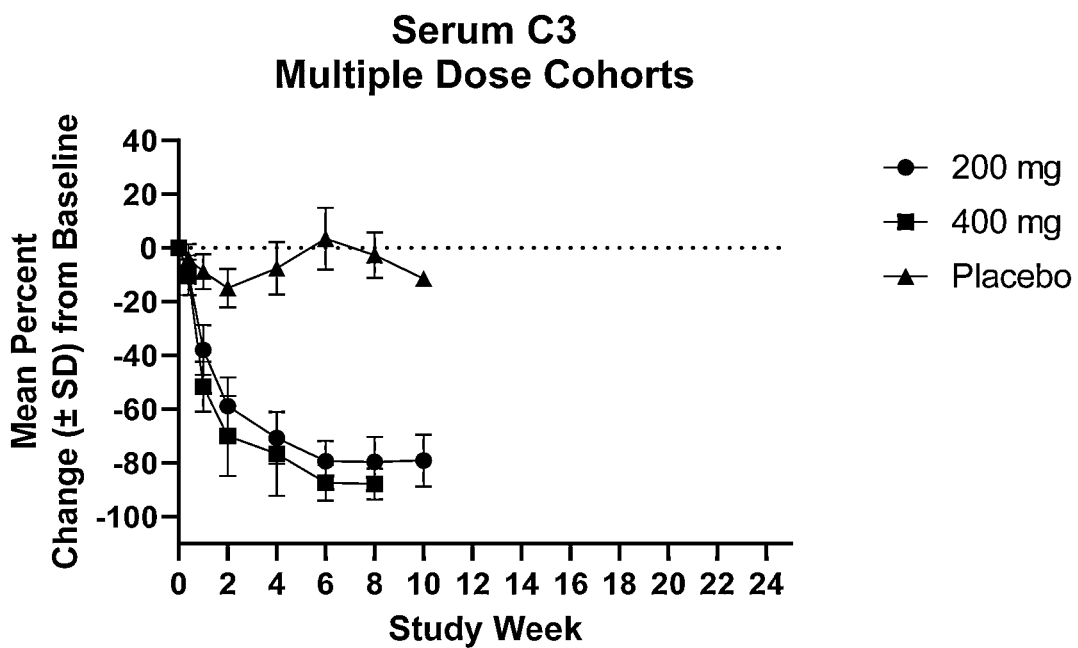
FIG. 12. Graph showing serum human C3 protein levels in subjects from the multiple ascending dose (MAD) portion of the Phase I/II clinical study described in Example 3, in normal human volunteers (NHVs).

In the NHV MAD cohorts, 4 weeks after the last dose, mean C3 reductions of 79.5% and 87.8% were achieved at 200 mg and 400 mg, respectively (see, e.g., FIG. 12). This was associated with mean reductions of 67% and 91.3% in AH50, and in 3 of the 4 subjects, more than 95% reduction in AH50 was observed in the 400 mg cohort. The maximum reduction of serum C3 protein levels in any single subject was an approximately 86% reduction in a subject in the 200 mg cohort and approximately 92% reduction in a subject in the 400 mg cohort. Wieslab® AP was also assessed in the MAD cohorts, and at week 8, the 200 mg cohort showed an approximately 87.2% mean reduction and the 400 mg cohort showed an approximately 99% mean reduction at week 8 (see FIG. 15). Given the extended duration of inhibitory effect observed, quarterly or possibly even less frequent dosing, particularly at the 400 mg dose, appears to be justified.

These data represent the first reported clinical data in human subjects with any inhibitor of C3 gene expression, and more specifically, are the first data ever reported in humans showing clinical inhibition of the alternative pathway by inhibition of C3 gene expression.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating IgA nephropathy (IgAN) or C3 glomerulopathy (C3G) in a human subject in need thereof, the method comprising administering to the human subject a pharmaceutical composition comprising a therapeutically effective amount of a RNAi agent for inhibiting expression of a C3 gene, wherein the RNAi agent comprises an antisense strand and a sense strand, wherein the antisense strand comprises the nucleotide sequence (5'→3') usUfsusCfgAfacaacAfgAfgUfaGfGfgsu (SEQ ID NO:13), and the sense strand comprises the nucleotide sequence (5'→3') (NAG37) s(invAb)sacccuacuCfUfGfuuguucgaaas(invAb) (SEQ ID NO:14), wherein a is 2'-O-methyl adenosine; c is 2'-O-methyl cytidine; g is 2'-O-methyl guanosine; u is 2'-O-methyl uridine, Af is 2'-fluoro adenosine, Cf is 2'-fluoro cytidine; Gf is 2'-fluoro guanosine; Uf is 2'-fluoro adenosine; s is a phosphorothioate linkage; (invAb) is an inverted abasic deoxyribose residue; and (NAG37)s comprises the following chemical structure:

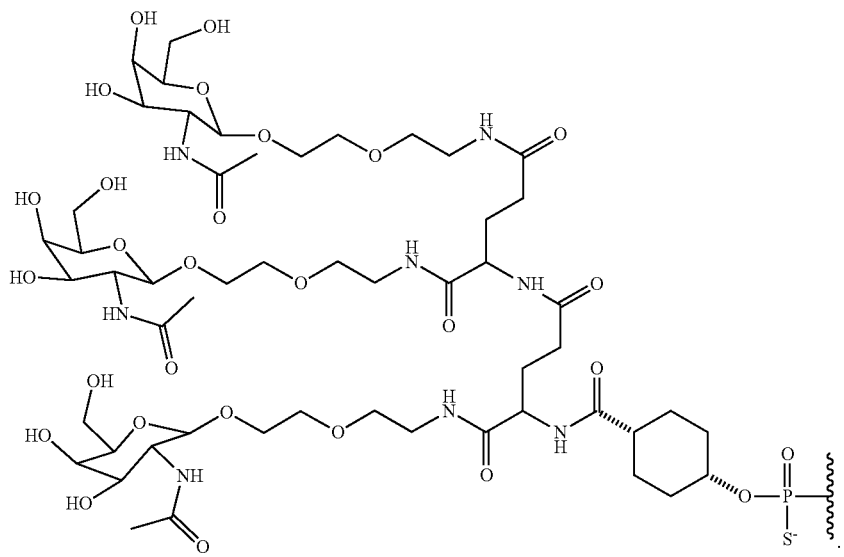

and wherein the RNAi agent is administered by subcutaneous injection at a dose of between about 25 mg and about 400 mg of RNAi agent.

2. The method of claim 1, wherein the RNAi agent is a pharmaceutically acceptable salt.

3. The method of claim 1, wherein the RNAi agent is a sodium salt.

4. The method of claim 1, wherein the pharmaceutical composition comprises a sodium phosphate buffer.

5. The method of claim 1, wherein the pharmaceutically composition comprises isotonic saline.

6. The method of claim 1, wherein the pharmaceutically composition comprises water for injection.

7. The method of claim 1, wherein the level of serum C3 protein is decreased in the subject.

8. The method of claim 1, wherein the alternative complement pathway hemolytic activity (AH50) is reduced in the subject by at least about 50%.

9. The method of claim 8, wherein the AH50 is reduced by approximately 90% or greater.

10. The method of claim 1, wherein the RNAi agent is formulated at 200 mg/mL in an aqueous sodium phosphate buffer, wherein the aqueous sodium phosphate buffer has a concentration of about 0.5 mM of sodium phosphate monobasic, and a concentration of 0.5 mM of sodium phosphate dibasic.

11. The method of claim 1, wherein the RNAi agent is administered to the human subject no more frequently than once every twelve weeks.

12. The method of claim 1, wherein the RNAi agent is administered to the human subject no more frequently than four times in a year.

13. The method of claim 1, wherein the method is for the treatment of IgA nephropathy (IgAN).

14. The method of claim 1, wherein the method is for the treatment of C3 glomerulopathy (C3G).

* * * * *

SEQUENCE LISTING

```
Sequence total quantity: 15
SEQ ID NO: 1            moltype = RNA   length = 5231
FEATURE                 Location/Qualifiers
source                  1..5231
                        mol_type = mRNA
                        organism = Homo sapiens
SEQUENCE: 1
actcctcccc atcctctccc tctgtccctc tgtccctctg accctgcact gtcccagcac   60
catgggaccc acctcaggtc ccagcctgct gctcctgcta ctaacccacc tccccctggc   120
tctggggagt cccatgtact ctatcatcac ccccaacatc ttgcggctgg agagcgagga   180
```

```
gaccatggtg ctggaggccc acgacgcgca aggggatgtt ccagtcactg ttactgtcca  240
cgacttccca ggcaaaaaac tagtgctgtc cagtgagaag actgtgctga ccctgccac  300
caaccacatg ggcaacgtca ccttcacgat cccagccaac agggagttca agtcagaaaa  360
ggggcgcaac aagttcgtga ccgtgcaggc caccttcggg acccaagtgg tggagaaggt  420
ggtgctggtc agcctgcaga gcgggtacct cttcatccag acagacaaga ccatctacac  480
ccctggctcc acagttctct atcggatctt caccgtcaac cacaagctgc tacccgtggg  540
ccggacggtc atggtcaaca ttgagaaccc ggaaggcatc ccggtcaagc aggactcctt  600
gtcttctcag aaccagcttg gcgtcttgcc cttgtcttgg acattccgg aactcgtcaa  660
catgggccag tggaagatcc gagcctacta tgaaaactca ccacagcagg tcttctccac  720
tgagtttgag gtgaaggagt acgtgctgcc cagtttcgag gtcatagtgg agcctacaga  780
gaaattctac tacatctata acgagaaggg cctggaggtc accatcaccg ccaggttcct  840
ctacgggaag aaagtggagg gaactgcctt tgtcatcttc gggatccagg atggcgaaca  900
gaggatttcc ctgcctgaat ccctcaagcg cattccgatt gaggatggct cggggaggt  960
tgtgctgagc cggaaggtac tgctggacgg ggtgcagaac cccgagcag aagacctggt  1020
ggggaagtct ttgtacgtgt ctgccaccgt catcttgcac tcaggcagtg acatggtgca  1080
ggcagagcgc agcgggatcc ccatcgtgac ctctccctac cagatccact tcaccaagac  1140
acccaagtac ttcaaaccag gaatgccctt tgacctcatg gtgttcgtga cgaacccctga  1200
tggctctcca gcctaccgag tccccgtggc agtccagggc gaggacactg tgcagtctct  1260
aacccaggga gatggcgtgg ccaaactcag catcaacaca caccccagcc agaagccctt  1320
gagcatcacg gtgcgcacga agaagcagga gctctcggag gcagagcagg ctaccaggac  1380
catgcaggct ctgccctaca gcaccgtggg caactccaac aattacctgc atctctcagt  1440
gctacgtaca gctcagac cggggagac cctcaacgtc aacttcctcc tgcgaatgta  1500
ccgcgcccac gaggccaaga tccgctacta cacctacctg atcatgaaca agggcaggct  1560
gttgaaggcg ggacgccagg tgcgagagcc cggccaggac ctggtggtgc tgcccctgtc  1620
catcaccacc gacttcatcc cttccttccg cctggtggcg tactacacgc tgatcggtgc  1680
cagcggccag agggaggtgg tggccgactc cgtgtgggta ggctcaagg actcctgcgt  1740
gggctcgctg gtggtaaaaa cggccagtc agaagaccgg cagctgtac ctgggcagca  1800
gatgaccctg aagatagagg gtgaccacgg ggcccgggtg gtactggtgg ccgtggacaa  1860
gggcgtgttc gtgctgaata agaagaacaa actgacgcag agtaagatct gggacgtggt  1920
ggagaaggca gacatcggct gcaccccggg cagtgggaag gattacgccg tgtcttctc  1980
cgacgcaggg ctgaccttca cgagcagcag tggccagcag accgcccaga gggcagaact  2040
tcagtgcccg cagccagccg cccgccgacg ccgttccgtg cagctcacgg agaagcgaat  2100
ggacaaagtc ggcaagtacc ccaaggagct gcgcaagtgc tgcgaggacg gcatgcggga  2160
gaacccatg aggttctcgt gccagcgccg gacccgtttc atctccctgg gcgaggcgtg  2220
caagaaggtc ttcctggact gctgcaacta catcacagag ctgcggcggc agcacgcgcg  2280
ggccagccac ctgggcctgg ccaggagtaa cctggatgag gacatcattg cagaagagaa  2340
catcgtttcc cgaagtgagt tcccagagag ctggctgtgg aacgttgagg acttgaaaga  2400
gccaccgaaa aatggaatct ctacgaagct catgaatata tttttgaaag actccatcac  2460
cacgtgggga attctggctg tgagcatgtc ggacaagaaa gggatctgtg tggcagaccc  2520
cttcgaggtc acagtaatgc aggacttctt catcgacctg cggctaccct actctgttgt  2580
tcgaaacgag caggtggaaa tccgagccgt tctctacaat taccggcaga accaagagct  2640
caaggtgagg gtggaactac tccacaatcc agccttctgc agcctggcca ccaccaagag  2700
gcgtcaccag cagaccgtaa ccatcccccc caagtcctgc ttgtccgttc catatgtcat  2760
cgtgccgcta aagaccggcc tgcaggaagt ggaagtcaag gctgctgtct accatcattt  2820
catcagtgac ggtgtcagga agtccctgaa ggtcgtgccg gaaggaatca gaatgaacaa  2880
aactgtggct gttcgcaccc tggatccaga acgcctgggc cgtgaaggag tgcagaaaga  2940
ggacatccca cctgcagacc tcagtgacca gtcccggacc accgagtctg agaccagaat  3000
tctcctgcaa gggaccccag tggcccagat gacagaggat gccgtcgacg cggaacggct  3060
gaagcacctc attgtgaccc cctcgggctg cggggaacag aacatgatcg gcatgacgcc  3120
cacggtcatc gctgtgcatt acctggatga aacggagcag tgggagaagt tcggcctaga  3180
gaagcggcag ggggccttgg agctcatcaa gaagggggtac accagcagc tggccttcag  3240
acaacccagc tctgccttg cggccttcgt gaaacgggca cccagcacct ggctgaccgc  3300
ctacgtggtc aagtcttct ctctggctgt caacctcatc gccatcgact cccaagtcct  3360
ctgcggggct gttaaatggc tgatcctgga gaagcagaag cccgacgggg tcttccagga  3420
ggatgcgccc gtgatacacc aagaaatgat tggtggatta cggaacaaca acagagaaaga  3480
catgcccctc acggccttg ttctcatctc gctgcaggag gctaaagata tttgcgagga  3540
gcaggtcaac agcctgccag gcagcatcac taaagcagga gacttccttg aagccaacta  3600
catgaaccta cagagatcct acactgtggc cattgctggc tatgctctgg cccagatggg  3660
caggctgaag gggcctcttc ttaacaaatt tctgaccaca gccaaagata agaaccgctg  3720
gggagaccct ggtaagcagc tctacaacgt ggaggccaca tcctatgccc tcttggccct  3780
actgcagcta aaagactttg actttgtgcc tccgtcgtg cgttggctca atgaacagag  3840
atactacggt ggtggctatg gctctaccca ggccaccttc atggtgttcc aagcttggc  3900
tcaataccaa aaggacgccc ctgaccacca ggaactgaac cttgatgtgt ccctccaact  3960
gcccagccgc agctccaaga tcacccaccg tatccactag gaatctgccg gcctcctgcg  4020
atcagaagag accaaggaaa atgagggttt cacagtcaca gctgaaggaa aaggccaagg  4080
cacccttgtcg gtggtgacaa tgtaccatgc taaggccaaa gatcaactca cctgtaataa  4140
attcgacctc aaggtcacca taaaaccagc accggaaaca gaaaagaggc tcaggatgc  4200
caagaacact atgatccttg agatctgtac caggtaccgg ggagaccagg atgccactat  4260
gtctatattg gacatatcca tgatgactgg ctttgtccca gacacagatg acctgaagca  4320
gctggccaat ggtgttgaca gatacatctc caagtatgag ctggacaaag ccttctccga  4380
taggaacacc ctcatcatct acctggacaa ggtctcacac tctgaggatg actgtctagc  4440
ttccaaagtt caccaatact ttaatgtaga gcttatccag cctggagcag tcaaggtcta  4500
cgcctattac aacctggagg aaagctgtac ccggttctca catccggaaa aggagggatg  4560
aaagctgaac aagtctgcc gtgatgaact gtgaggaga attgcttcat  4620
acaaaagtcg gatgacaagg tcaccctgga agaacggctg acaagggcct gtgagccagg  4680
agtggactat gtgtacaaga cccgactggt caaggttcag ctgtccaatg actttgacga  4740
gtacatcatg gccattgagc agaccatcaa gtcaggctcg gatgaggtgc aggttggaca  4800
gcagcgcacg ttcatcagcc ccatcaagtg cagagaagcc ctgaagctgg aggagaagaa  4860
acactacctc atgtggggtc tctcctccga tttctgggga gagaagccca acctcagcta  4920
```

```
catcatcggg aaggacactt gggtggagca ctggcccgag gaggacgaat gccaagacga    4980
agagaaccag aaacaatgcc aggacctcgg cgccttcacc gagagcatgg ttgtctttgg    5040
gtgcccccaac tgaccacacc cccattcccc cactccagat aaagcttcag ttatatctca   5100
cgtgtctgga gttctttgcc aagagggaga ggctgaaatc cccagccgcc tcacctcag     5160
ctcagctcca tcctacttga aacctcacct gttcccaccg cattttctcc tggcgttcgc    5220
ctgctagtgt g                                                        5231

SEQ ID NO: 2         moltype = RNA   length = 21
FEATURE              Location/Qualifiers
source               1..21
                     mol_type = other RNA
                     organism = synthetic construct
SEQUENCE: 2
accctactct gttgttcgaa a                                              21

SEQ ID NO: 3         moltype = RNA   length = 21
FEATURE              Location/Qualifiers
source               1..21
                     mol_type = other RNA
                     organism = synthetic construct
SEQUENCE: 3
tttcgaacaa cagagtaggg t                                              21

SEQ ID NO: 4         moltype = RNA   length = 21
FEATURE              Location/Qualifiers
source               1..21
                     mol_type = other RNA
                     organism = synthetic construct
SEQUENCE: 4
attcgaacaa cagagtaggg t                                              21

SEQ ID NO: 5         moltype = RNA   length = 21
FEATURE              Location/Qualifiers
source               1..21
                     mol_type = other RNA
                     organism = synthetic construct
SEQUENCE: 5
nttcgaacaa cagagtaggg t                                              21

SEQ ID NO: 6         moltype = RNA   length = 21
FEATURE              Location/Qualifiers
source               1..21
                     mol_type = other RNA
                     organism = synthetic construct
SEQUENCE: 6
tttcgaacaa cagagtaggg n                                              21

SEQ ID NO: 7         moltype = RNA   length = 21
FEATURE              Location/Qualifiers
source               1..21
                     mol_type = other RNA
                     organism = synthetic construct
SEQUENCE: 7
nttcgaacaa cagagtaggg n                                              21

SEQ ID NO: 8         moltype = RNA   length = 21
FEATURE              Location/Qualifiers
source               1..21
                     mol_type = other RNA
                     organism = synthetic construct
SEQUENCE: 8
accctactct gttgttcgaa a                                              21

SEQ ID NO: 9         moltype = RNA   length = 21
FEATURE              Location/Qualifiers
source               1..21
                     mol_type = other RNA
                     organism = synthetic construct
SEQUENCE: 9
accctactct gttgttcgaa t                                              21

SEQ ID NO: 10        moltype = RNA   length = 21
FEATURE              Location/Qualifiers
source               1..21
                     mol_type = other RNA
                     organism = synthetic construct
SEQUENCE: 10
accctactct gttgttcgaa n                                              21
```

```
SEQ ID NO: 11              moltype = RNA   length = 21
FEATURE                    Location/Qualifiers
source                     1..21
                           mol_type = other RNA
                           organism = synthetic construct
SEQUENCE: 11
nccctactct gttgttcgaa a                                                   21

SEQ ID NO: 12              moltype = RNA   length = 21
FEATURE                    Location/Qualifiers
source                     1..21
                           mol_type = other RNA
                           organism = synthetic construct
SEQUENCE: 12
nccctactct gttgttcgaa n                                                   21

SEQ ID NO: 13              moltype = RNA   length = 21
FEATURE                    Location/Qualifiers
modified_base              1
                           mod_base = um
modified_base              1^2
                           mod_base = OTHER
                           note = phosphorothioate linkage
modified_base              2
                           mod_base = OTHER
                           note = 2'-fluorouridine
modified_base              2^3
                           mod_base = OTHER
                           note = phosphorothioate linkage
modified_base              3
                           mod_base = um
modified_base              3^4
                           mod_base = OTHER
                           note = phosphorothioate linkage
modified_base              4
                           mod_base = OTHER
                           note = 2'-fluorocytidine
modified_base              5
                           mod_base = gm
modified_base              6
                           mod_base = OTHER
                           note = 2'-fluoroadenosine
modified_base              7
                           mod_base = OTHER
                           note = 2'-O-methyladenosine
modified_base              8
                           mod_base = cm
modified_base              9
                           mod_base = OTHER
                           note = 2'-O-methyladenosine
modified_base              10
                           mod_base = OTHER
                           note = 2'-O-methyladenosine
modified_base              11
                           mod_base = cm
modified_base              12
                           mod_base = OTHER
                           note = 2'-fluoroadenosine
modified_base              13
                           mod_base = gm
modified_base              14
                           mod_base = OTHER
                           note = 2'-fluoroadenosine
modified_base              15
                           mod_base = gm
modified_base              16
                           mod_base = OTHER
                           note = 2'-fluorouridine
modified_base              17
                           mod_base = OTHER
                           note = 2'-O-methyladenosine
modified_base              18
                           mod_base = OTHER
                           note = 2'-fluoroguanosine
modified_base              19
                           mod_base = OTHER
                           note = 2'-fluoroguanosine
modified_base              20
                           mod_base = gm
```

```
modified_base         20^21
                      mod_base = OTHER
                      note = phosphorothioate linkage
modified_base         21
                      mod_base = um
source                1..21
                      mol_type = other RNA
                      organism = synthetic construct
SEQUENCE: 13
tttcgaacaa cagagtaggg t                                              21

SEQ ID NO: 14         moltype = RNA  length = 21
FEATURE               Location/Qualifiers
modified_base         1
                      mod_base = OTHER
                      note = 2'-O-methyladenosine
modified_base         2
                      mod_base = cm
modified_base         3
                      mod_base = cm
modified_base         4
                      mod_base = cm
modified_base         5
                      mod_base = um
modified_base         6
                      mod_base = OTHER
                      note = 2'-O-methyladenosine
modified_base         7
                      mod_base = cm
modified_base         8
                      mod_base = um
modified_base         9
                      mod_base = OTHER
                      note = 2'-fluorocytidine
modified_base         10
                      mod_base = OTHER
                      note = 2'-fluorouridine
modified_base         11
                      mod_base = OTHER
                      note = 2'-fluoroguanosine
modified_base         12
                      mod_base = um
modified_base         13
                      mod_base = um
modified_base         14
                      mod_base = gm
modified_base         15
                      mod_base = um
modified_base         16
                      mod_base = um
modified_base         17
                      mod_base = cm
modified_base         18
                      mod_base = gm
modified_base         19
                      mod_base = OTHER
                      note = 2'-O-methyladenosine
modified_base         20
                      mod_base = OTHER
                      note = 2'-O-methyladenosine
modified_base         21
                      mod_base = OTHER
                      note = 2'-O-methyladenosine
source                1..21
                      mol_type = other RNA
                      organism = synthetic construct
```

```
SEQUENCE: 14
accctactct gttgttcgaa a                                      21

SEQ ID NO: 15            moltype = RNA  length = 21
FEATURE                  Location/Qualifiers
modified_base            1
                         mod_base = OTHER
                         note = 2'-O-methyladenosine
modified_base            2
                         mod_base = cm
modified_base            3
                         mod_base = cm
modified_base            4
                         mod_base = cm
modified_base            5
                         mod_base = um
modified_base            6
                         mod_base = OTHER
                         note = 2'-O-methyladenosine
modified_base            7
                         mod_base = cm
modified_base            8
                         mod_base = um
modified_base            9
                         mod_base = OTHER
                         note = 2'-fluorocytidine
modified_base            10
                         mod_base = OTHER
                         note = 2'-fluorouridine
modified_base            11
                         mod_base = OTHER
                         note = 2'-fluoroguanosine
modified_base            12
                         mod_base = um
modified_base            13
                         mod_base = um
modified_base            14
                         mod_base = gm
modified_base            15
                         mod_base = um
modified_base            16
                         mod_base = um
modified_base            17
                         mod_base = cm
modified_base            18
                         mod_base = gm
modified_base            19
                         mod_base = OTHER
                         note = 2'-O-methyladenosine
modified_base            20
                         mod_base = OTHER
                         note = 2'-O-methyladenosine
modified_base            21
                         mod_base = OTHER
                         note = 2'-O-methyladenosine
source                   1..21
                         mol_type = other RNA
                         organism = synthetic construct
SEQUENCE: 15
accctactct gttgttcgaa a                                      21
```